United States Patent
Kokish et al.

(10) Patent No.: US 11,278,703 B2
(45) Date of Patent: Mar. 22, 2022

(54) DEVICES, SYSTEMS, AND METHODS FOR CONTROLLING ACTIVE DRIVE SYSTEMS

(71) Applicant: Auris Health, Inc., Redwood City, CA (US)

(72) Inventors: Arkady Kokish, Los Gatos, CA (US); Sean P. Walker, Fremont, CA (US); Kamini Balaji, Sunnyvale, CA (US); Francis Macnamara, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 688 days.

(21) Appl. No.: 16/036,295

(22) Filed: Jul. 16, 2018

(65) Prior Publication Data

US 2018/0326181 A1 Nov. 15, 2018

Related U.S. Application Data

(63) Continuation of application No. 14/692,499, filed on Apr. 21, 2015, now Pat. No. 10,046,140.
(Continued)

(51) Int. Cl.
*A61M 25/01* (2006.01)
*A61B 34/30* (2016.01)
(Continued)

(52) U.S. Cl.
CPC ......... *A61M 25/0113* (2013.01); *A61B 34/30* (2016.02); *A61B 34/37* (2016.02);
(Continued)

(58) Field of Classification Search
CPC ......... A61B 34/30; A61B 34/37; A61B 34/71; A61B 46/10; A61B 2017/00477;
(Continued)

(56) References Cited

U.S. PATENT DOCUMENTS

| | | | | |
|---|---|---|---|---|
| 2,262,631 A | * | 11/1941 | Belluche | B65H 29/042 |
| | | | | 271/243 |
| 2,556,601 A | | 6/1951 | Schofield | |

(Continued)

FOREIGN PATENT DOCUMENTS

| | | |
|---|---|---|
| CA | 2285342 | 10/1998 |
| CN | 101161426 | 4/2008 |

(Continued)

OTHER PUBLICATIONS

Amendment and Response to Non-Final Office Action for related U.S. Appl. No. 11/678,016 filed Dec. 27, 2010 (21 pages).
(Continued)

*Primary Examiner* — Mahdi H Nejad
(74) *Attorney, Agent, or Firm* — Frost Brown Todd LLC

(57) ABSTRACT

The present application is related to devices, systems, and methods for controlling active drive systems. In one embodiment, the drive system may include a first surface and a second surface for engaging an elongate member. The first and second surfaces may be attached to a drive mechanism to move the elongate member. The first surface may be slidable relative to the drive mechanism and may have a clearance between the drive mechanism and an end of the first surface during movement of the elongate member in a non-slip condition. A sensor may be associated with the first surface and may be configured to detect movement of the first surface in a slip condition.

20 Claims, 46 Drawing Sheets

Related U.S. Application Data

(60) Provisional application No. 62/042,451, filed on Aug. 27, 2014, provisional application No. 62/031,925, filed on Aug. 1, 2014, provisional application No. 62/016,334, filed on Jun. 24, 2014, provisional application No. 61/984,354, filed on Apr. 25, 2014, provisional application No. 61/982,021, filed on Apr. 21, 2014.

(51) Int. Cl.
  *A61B 34/37* (2016.01)
  *A61B 34/00* (2016.01)
  *A61B 46/10* (2016.01)
  *A61B 17/00* (2006.01)
  *A61B 90/00* (2016.01)

(52) U.S. Cl.
  CPC .............. *A61B 34/71* (2016.02); *A61B 46/10* (2016.02); *A61B 2017/00477* (2013.01); *A61B 2034/301* (2016.02); *A61B 2090/064* (2016.02); *A61M 25/0147* (2013.01); *A61M 2205/332* (2013.01)

(58) Field of Classification Search
  CPC ....... A61B 2034/301; A61B 2090/064; A61M 25/0113; A61M 25/0147; A61M 2205/332
  USPC ....................................................... 606/130
  See application file for complete search history.

(56) References Cited

U.S. PATENT DOCUMENTS

| | | |
|---|---|---|
| 2,566,183 A | 8/1951 | Forss |
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,835,854 A * | 9/1974 | Jewett ................ A61M 25/0113 604/159 |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,305 A | 7/1990 | Blood |
| 4,945,790 A | 8/1990 | Golden |
| 5,078,714 A | 1/1992 | Katims |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,339,799 A | 8/1994 | Kami et al. |
| 5,341,807 A | 8/1994 | Nardella |
| 5,350,101 A | 9/1994 | Godlewski |
| 5,368,015 A | 11/1994 | Wilk |
| 5,394,875 A | 3/1995 | Lewis et al. |
| 5,397,443 A | 3/1995 | Michaels |
| 5,398,691 A | 3/1995 | Martin et al. |
| 5,408,409 A | 4/1995 | Glassman et al. |
| 5,426,687 A | 6/1995 | Goodall et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,507,725 A | 4/1996 | Savage et al. |
| 5,524,180 A | 6/1996 | Wang et al. |
| 5,559,294 A | 9/1996 | Holum et al. |
| 5,600,330 A | 2/1997 | Blood |
| 5,613,973 A | 3/1997 | Jackson et al. |
| 5,662,108 A | 9/1997 | Budd et al. |
| 5,673,704 A | 10/1997 | Marchlinski et al. |
| 5,697,377 A | 12/1997 | Wittkampf |
| 5,709,661 A | 1/1998 | Van Egmond |
| 5,713,946 A | 2/1998 | Ben-Haim |
| 5,722,959 A | 3/1998 | Bierman |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,767,840 A | 6/1998 | Selker |
| 5,779,623 A | 7/1998 | Bonnell |
| 5,784,542 A | 7/1998 | Ohm et al. |
| 5,792,135 A | 8/1998 | Madhani et al. |
| 5,797,900 A | 8/1998 | Madhani |
| 5,799,055 A | 8/1998 | Peshkin et al. |
| 5,825,982 A | 10/1998 | Wright et al. |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,842,390 A | 12/1998 | Bouligny |
| 5,843,076 A | 12/1998 | Webster, Jr. et al. |
| 5,845,646 A | 12/1998 | Lemelson |
| 5,855,583 A | 1/1999 | Wang et al. |
| 5,859,934 A | 1/1999 | Green |
| 5,876,325 A | 3/1999 | Mizuno et al. |
| 5,878,193 A | 3/1999 | Wang et al. |
| 5,891,095 A | 4/1999 | Eggers et al. |
| 5,921,968 A | 7/1999 | Lampropoulos et al. |
| 5,925,078 A | 7/1999 | Anderson |
| 5,935,079 A | 8/1999 | Swanson et al. |
| 5,950,629 A | 9/1999 | Taylor et al. |
| 5,951,475 A | 9/1999 | Gueziec et al. |
| 5,953,683 A | 9/1999 | Hansen et al. |
| 5,967,934 A | 10/1999 | Ishida et al. |
| 5,983,126 A | 11/1999 | Wittkampf |
| 6,004,271 A | 12/1999 | Moore |
| 6,061,587 A | 5/2000 | Kucharczyk et al. |
| 6,063,022 A | 5/2000 | Ben-Haim |
| 6,063,095 A | 5/2000 | Wang et al. |
| 6,077,219 A | 6/2000 | Viebach |
| 6,080,181 A | 6/2000 | Jensen et al. |
| 6,083,170 A | 7/2000 | Ben-Haim |
| 6,084,371 A | 7/2000 | Kress et al. |
| 6,096,004 A | 8/2000 | Meglan et al. |
| 6,106,511 A | 8/2000 | Jensen |
| 6,129,668 A | 10/2000 | Haynor et al. |
| 6,132,368 A | 10/2000 | Cooper |
| 6,154,000 A | 11/2000 | Rastegar et al. |
| 6,161,032 A | 12/2000 | Acker |
| 6,171,234 B1 | 1/2001 | White et al. |
| 6,172,499 B1 | 1/2001 | Ashe |
| 6,185,478 B1 | 2/2001 | Koakutsu et al. |
| 6,203,493 B1 | 3/2001 | Ben-Haim |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,504 B1 | 5/2001 | Das et al. |
| 6,246,200 B1 | 6/2001 | Blumenkranz et al. |
| 6,259,806 B1 | 7/2001 | Green |
| 6,266,551 B1 | 7/2001 | Osadchy et al. |
| 6,272,371 B1 | 8/2001 | Shlomo |
| 6,289,579 B1 | 9/2001 | Viza et al. |
| 6,301,496 B1 | 10/2001 | Reisfeld |

(56) References Cited

U.S. PATENT DOCUMENTS

| | | |
|---|---|---|
| 6,309,397 B1 | 10/2001 | Julian et al. |
| 6,310,828 B1 | 10/2001 | Mumm et al. |
| 6,312,435 B1 | 11/2001 | Wallace et al. |
| 6,331,181 B1 | 12/2001 | Tierney et al. |
| 6,363,279 B1 | 3/2002 | Ben-Haim et al. |
| 6,370,411 B1 | 4/2002 | Osadchy et al. |
| 6,371,952 B1 | 4/2002 | Madhani et al. |
| 6,375,471 B1 | 4/2002 | Wendiandt et al. |
| 6,380,732 B1 | 4/2002 | Gilboa |
| 6,381,483 B1 | 4/2002 | Hareyama et al. |
| 6,393,340 B2 | 5/2002 | Funda et al. |
| 6,394,998 B1 | 5/2002 | Wallace et al. |
| 6,398,731 B1 | 6/2002 | Mumm et al. |
| 6,400,979 B1 | 6/2002 | Stoianovici et al. |
| 6,401,572 B1 | 6/2002 | Provost |
| 6,415,171 B1 | 7/2002 | Gueziec et al. |
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,500,128 B2 | 12/2002 | Marino |
| 6,530,913 B1 | 3/2003 | Giba et al. |
| 6,544,230 B1 | 4/2003 | Flaherty |
| 6,565,554 B1 | 5/2003 | Niemeyer |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,665,554 B1 * | 12/2003 | Charles .............. A61B 90/36 600/427 |
| 6,669,709 B1 | 12/2003 | Cohn |
| 6,685,698 B2 | 2/2004 | Morley et al. |
| 6,695,818 B2 | 2/2004 | Wollschlager |
| 6,699,235 B2 | 3/2004 | Wallace et al. |
| 6,716,166 B2 | 4/2004 | Govari |
| 6,726,675 B1 | 4/2004 | Beyar |
| 6,741,883 B2 | 5/2004 | Gildenberg |
| 6,774,624 B2 | 8/2004 | Anderson et al. |
| 6,783,524 B2 | 8/2004 | Anderson et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,963,792 B1 | 11/2005 | Green |
| 7,021,173 B2 | 4/2006 | Stoianovici et al. |
| 7,044,936 B2 | 5/2006 | Harding |
| 7,074,179 B2 | 7/2006 | Wang et al. |
| 7,087,049 B2 | 8/2006 | Nowlin et al. |
| 7,155,315 B2 | 12/2006 | Niemeyer et al. |
| 7,169,141 B2 | 1/2007 | Brock et al. |
| 7,172,580 B2 | 2/2007 | Hruska et al. |
| 7,225,012 B1 | 5/2007 | Susil et al. |
| 7,276,044 B2 | 10/2007 | Ferry et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock |
| 7,404,824 B1 | 7/2008 | Webler et al. |
| 7,494,494 B2 | 2/2009 | Stoianovici et al. |
| 7,540,866 B2 | 6/2009 | Viswanathan et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,850,642 B2 | 12/2010 | Moll et al. |
| 7,938,809 B2 | 5/2011 | Lampropoulos et al. |
| 7,963,288 B2 | 6/2011 | Rosenberg et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,092,397 B2 | 1/2012 | Wallace et al. |
| 8,126,534 B2 | 2/2012 | Maschke |
| 8,157,308 B2 | 4/2012 | Pedersen |
| 8,182,415 B2 | 5/2012 | Larkin et al. |
| 8,190,238 B2 | 5/2012 | Moll et al. |
| 8,202,244 B2 | 6/2012 | Cohen et al. |
| 8,219,178 B2 | 7/2012 | Smith et al. |
| 8,235,942 B2 | 8/2012 | Frassica et al. |
| 8,244,327 B2 | 8/2012 | Fichtinger et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,430,398 B2 * | 4/2013 | Kamichi ............... B65H 3/44 271/171 |
| 8,498,691 B2 | 7/2013 | Moll et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,827,948 B2 | 9/2014 | Romo et al. |
| 8,870,815 B2 | 10/2014 | Bhat et al. |
| 8,894,610 B2 | 11/2014 | MacNamara et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,014,851 B2 | 4/2015 | Wong et al. |
| 9,023,068 B2 | 5/2015 | Viola |
| 9,057,600 B2 | 6/2015 | Walker et al. |
| 9,138,166 B2 | 9/2015 | Wong et al. |
| 9,173,713 B2 | 11/2015 | Hart et al. |
| 9,204,933 B2 | 12/2015 | Reis et al. |
| 9,254,123 B2 | 2/2016 | Alvarez et al. |
| 9,259,281 B2 | 2/2016 | Griffiths et al. |
| 9,271,663 B2 | 3/2016 | Walker et al. |
| 9,283,046 B2 | 3/2016 | Walker et al. |
| 9,289,578 B2 | 3/2016 | Walker et al. |
| 9,326,822 B2 | 5/2016 | Lewis et al. |
| 9,343,040 B2 | 5/2016 | Miller et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,291 B2 | 11/2016 | Balaji et al. |
| 9,498,601 B2 | 11/2016 | Tanner et al. |
| 9,504,604 B2 | 11/2016 | Alvarez |
| 9,532,840 B2 | 1/2017 | Wong et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,636,483 B2 | 5/2017 | Hart et al. |
| 9,668,814 B2 | 6/2017 | Kokish |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |

(56) References Cited

U.S. PATENT DOCUMENTS

| | | | |
|---|---|---|---|
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,143,360 B2 | 12/2018 | Roelle et al. |
| 10,145,747 B1 | 12/2018 | Lin et al. |
| 10,159,532 B1 | 12/2018 | Ummalaneni et al. |
| 10,258,285 B2 | 4/2019 | Hauck |
| 10,299,870 B2 | 5/2019 | Connolly et al. |
| 10,426,559 B2 | 10/2019 | Graetzel et al. |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,702,348 B2 | 7/2020 | Moll et al. |
| 10,716,461 B2 | 7/2020 | Jenkins |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 2001/0009976 A1 | 7/2001 | Panescu et al. |
| 2001/0029366 A1 | 10/2001 | Swanson et al. |
| 2001/0042643 A1 | 11/2001 | Krueger et al. |
| 2002/0045905 A1 | 4/2002 | Gerbi et al. |
| 2002/0087169 A1 | 7/2002 | Brock et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0138009 A1 | 9/2002 | Brockway et al. |
| 2002/0156369 A1 | 10/2002 | Chakeres |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0050649 A1 | 3/2003 | Brock et al. |
| 2003/0056561 A1 | 3/2003 | Butscher et al. |
| 2003/0073908 A1 | 4/2003 | Desai |
| 2003/0074011 A1 | 4/2003 | Gilboa et al. |
| 2003/0109780 A1 | 6/2003 | Coste-Maniere et al. |
| 2003/0135204 A1 | 7/2003 | Lee et al. |
| 2003/0167623 A1 | 9/2003 | Lorenz |
| 2003/0212308 A1 | 11/2003 | Bendall |
| 2004/0015053 A1 | 1/2004 | Bieger |
| 2004/0034282 A1 | 2/2004 | Quaid, III |
| 2004/0034365 A1 | 2/2004 | Lentz et al. |
| 2004/0152972 A1 | 8/2004 | Hunter |
| 2004/0171929 A1 | 9/2004 | Leitner et al. |
| 2004/0176751 A1 | 9/2004 | Weitzner et al. |
| 2004/0193146 A1 | 9/2004 | Lee et al. |
| 2004/0220588 A1 | 11/2004 | Kermode et al. |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0027397 A1 | 2/2005 | Niemeyer |
| 2005/0059960 A1 | 3/2005 | Simaan et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0177026 A1 | 8/2005 | Hoeg et al. |
| 2005/0182295 A1 | 8/2005 | Soper et al. |
| 2005/0182330 A1 | 8/2005 | Brockway et al. |
| 2005/0183532 A1 | 8/2005 | Najaf et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2006/0013523 A1 | 1/2006 | Childers et al. |
| 2006/0025676 A1 | 2/2006 | Viswanathan et al. |
| 2006/0025679 A1 | 2/2006 | Viswanathan et al. |
| 2006/0041245 A1 | 2/2006 | Ferry |
| 2006/0058647 A1 | 3/2006 | Strommer et al. |
| 2006/0111692 A1 | 5/2006 | Hlavka et al. |
| 2006/0146010 A1 | 7/2006 | Schneider |
| 2006/0178556 A1 | 8/2006 | Hasser et al. |
| 2006/0200049 A1 | 9/2006 | Leo et al. |
| 2006/0201688 A1 | 9/2006 | Jenner et al. |
| 2006/0229587 A1 | 10/2006 | Beyar et al. |
| 2006/0229641 A1 | 10/2006 | Gupta et al. |
| 2006/0237205 A1 | 10/2006 | Sia et al. |
| 2006/0271036 A1 | 11/2006 | Garabedian et al. |
| 2007/0000498 A1 | 1/2007 | Glynn et al. |
| 2007/0013336 A1 | 1/2007 | Nowlin et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0123851 A1 | 5/2007 | Alejandro et al. |
| 2007/0149946 A1 | 6/2007 | Viswanathan |
| 2007/0185485 A1 | 8/2007 | Hauck et al. |
| 2007/0185486 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0249901 A1 | 10/2007 | Ohline et al. |
| 2007/0287999 A1 | 12/2007 | Malecki et al. |
| 2007/0293724 A1 | 12/2007 | Saadat et al. |
| 2007/0299427 A1 | 12/2007 | Yeung et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0039255 A1 | 2/2008 | Jinno et al. |
| 2008/0046122 A1 | 2/2008 | Manzo et al. |
| 2008/0064920 A1 | 3/2008 | Bakos et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0183071 A1 | 7/2008 | Strommer et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2008/0319311 A1 | 12/2008 | Hamadeh |
| 2009/0005768 A1 | 1/2009 | Sharareh |
| 2009/0054884 A1 | 2/2009 | Farley et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0131872 A1 | 5/2009 | Popov |
| 2009/0163948 A1 | 6/2009 | Sunaoshi |
| 2009/0171371 A1 | 7/2009 | Nixon |
| 2009/0195628 A1* | 8/2009 | Innes ............... B26D 1/085 347/104 |
| 2009/0221908 A1 | 9/2009 | Glossop |
| 2009/0247944 A1 | 10/2009 | Kirschenman et al. |
| 2009/0248039 A1 | 10/2009 | Cooper et al. |
| 2009/0318797 A1 | 12/2009 | Hadani |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081920 A1 | 4/2010 | Whitmore, III et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0187740 A1 | 7/2010 | Orgeron |
| 2010/0204646 A1 | 8/2010 | Plicchi et al. |
| 2010/0210923 A1 | 8/2010 | Li et al. |

(56) References Cited

U.S. PATENT DOCUMENTS

| | | |
|---|---|---|
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2010/0280320 A1 | 11/2010 | Alvarez et al. |
| 2010/0280525 A1 | 11/2010 | Alvarez et al. |
| 2010/0332033 A1 | 12/2010 | Diolaiti |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Online et al. |
| 2012/0016346 A1 | 1/2012 | Steinmetz et al. |
| 2012/0046652 A1 | 2/2012 | Sokel |
| 2012/0316393 A1 | 2/2012 | Frassica et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0245595 A1 | 9/2012 | Kesavadas et al. |
| 2012/0277730 A1 | 11/2012 | Salahieh |
| 2012/0283747 A1 | 11/2012 | Popovic |
| 2012/0310112 A1 | 12/2012 | Fichtinger et al. |
| 2013/0012779 A1 | 1/2013 | Frassica et al. |
| 2013/0018400 A1 | 1/2013 | Milton et al. |
| 2013/0030363 A1 | 1/2013 | Wong et al. |
| 2013/0066335 A1 | 3/2013 | Barwinkel |
| 2013/0144116 A1 | 6/2013 | Cooper et al. |
| 2013/0231678 A1* | 9/2013 | Wenderow .......... A61B 34/37 606/130 |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0257334 A1 | 9/2014 | Wong et al. |
| 2014/0264081 A1 | 9/2014 | Walker et al. |
| 2014/0275988 A1 | 9/2014 | Walker et al. |
| 2014/0276233 A1 | 9/2014 | Murphy |
| 2014/0276389 A1 | 9/2014 | Walker |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276646 A1 | 9/2014 | Wong et al. |
| 2014/0276934 A1 | 9/2014 | Balaji et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0277333 A1 | 9/2014 | Lewis |
| 2014/0277334 A1 | 9/2014 | Yu et al. |
| 2014/0277747 A1 | 9/2014 | Walker et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2015/0012134 A1 | 1/2015 | Robinson |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133858 A1 | 5/2015 | Julian et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0223902 A1 | 8/2015 | Walker et al. |
| 2015/0231364 A1 | 8/2015 | Blanchard |
| 2015/0265807 A1 | 9/2015 | Park et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2015/0375399 A1 | 12/2015 | Chiu et al. |
| 2016/0000512 A1 | 1/2016 | Gombert et al. |
| 2016/0001038 A1 | 1/2016 | Romo et al. |
| 2016/0007881 A1 | 1/2016 | Wong et al. |
| 2016/0151122 A1 | 6/2016 | Alvarez et al. |
| 2016/0157945 A1 | 6/2016 | Madhani |
| 2016/0166234 A1 | 6/2016 | Zhang |
| 2016/0175059 A1 | 6/2016 | Walker et al. |
| 2016/0192860 A1 | 7/2016 | Allenby |
| 2016/0202053 A1 | 7/2016 | Walker et al. |
| 2016/0206389 A1 | 7/2016 | Miller |
| 2016/0213435 A1 | 7/2016 | Hourtash |
| 2016/0228032 A1 | 8/2016 | Walker et al. |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0065356 A1 | 3/2017 | Balaji et al. |
| 2017/0071684 A1 | 3/2017 | Kokish et al. |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0105804 A1 | 4/2017 | Yu |
| 2017/0113019 A1 | 4/2017 | Wong et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151027 A1 | 6/2017 | Walker et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0209672 A1 | 7/2017 | Hart et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0325932 A1 | 11/2017 | Hoelzle |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0055589 A1 | 3/2018 | Joseph et al. |

(56) References Cited

U.S. PATENT DOCUMENTS

| | | |
|---|---|---|
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0271616 A1 | 9/2018 | Schuh et al. |
| 2018/0279852 A1 | 10/2018 | Rafil-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0110839 A1 | 4/2019 | Rafii-Tari et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0231458 A1 | 8/2019 | DiMaio |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli et al. |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 101500470 | 8/2009 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103735313 | 4/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 97/44089 | 11/1997 |
| WO | WO 00/11495 | 3/2000 |
| WO | WO 00/45193 | 8/2000 |
| WO | WO 02/074178 | 9/2002 |
| WO | WO 03/077769 | 9/2003 |
| WO | WO 03/086190 | 10/2003 |
| WO | WO 03/091839 | 11/2003 |
| WO | WO 05/087128 | 9/2005 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 14/028699 | 2/2014 |
| WO | WO 14/028702 | 2/2014 |
| WO | WO 15/127231 | 8/2015 |
| WO | WO 17/059412 | 4/2017 |
| WO | WO 17/151993 | 9/2017 |

OTHER PUBLICATIONS

European Search Report for European Patent Application No. 14160078.3 dated Feb. 11, 2015. (6 pages).
Extended European Search Report dated Feb. 6, 2015 in patent application No. 14160068.4, 6 pp.
International Search Report for International Patent Application No. PCT/US2005/007108, dated Jun. 27, 2005 (4 pages).
Written Opinion of the International Searching Authority for International Patent Application No. PCT/US2005/007108, dated Jun. 27, 2005 (6 pages).
International Search Report for International Patent Application No. PCT/US2006/026218, dated Dec. 12, 2006 (4 pages).
Written Opinion of the International Searching Authority for International Patent Aprlication No. PCT/US2006/026218, dated Dec. 12, 2006 (7 pages).
International Preliminary Report on Patentability for International Patent Application No. PCT/US2007/062617, dated Aug. 26, 2008 (7 pages).
Non/Final Office Action for related U.S. Appl. No. 11/678,016, dated Aug. 31, 2010 (30 pages).

(56) References Cited

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

* cited by examiner

DEVICES, SYSTEMS, AND METHODS FOR CONTROLLING ACTIVE DRIVE SYSTEMS

CROSS-REFERENCE TO RELATED APPLICATIONS

This application is a continuation of U.S. patent application Ser. No. 14/692,499, filed on Apr. 21, 2015, issued as U.S. Pat. No. 10,046,140 on Aug. 14, 2018, which claims priority to U.S. provisional patent application Ser. No. 61/982,021, titled "Variable Stroke for Drive Devices", filed on Apr. 21, 2014; U.S. provisional patent application Ser. No. 61/984,354, titled "Slip Detection by Differential Pad Strain", filed Apr. 25, 2014; U.S. provisional patent application Ser. No. 62/016,334, titled "Multi-Durometer Pad System", filed on Jun. 24, 2014; U.S. provisional patent application Ser. No. 62/031,925, titled "Slip Detection by Passive Pad Movement", filed Aug. 1, 2014; U.S. provisional patent application Ser. No. 62/042,451, titled "Control Mechanisms for Active Drive with a Slip Detection Capability", filed Aug. 27, 2014, all of which are herein incorporated by reference in their entirety.

This application is related to U.S. provisional patent application Ser. No. 61/922,984, titled "Catheter Assembly for Slip and Buckling Detection", filed Jan. 2, 2014; U.S. provisional patent application Ser. No. 61/925,746, titled "A method to use electrical current profiles to synchronize and align motors", filed on Jan. 10, 2014, all of which are herein incorporated by reference in their entirety.

This application is related to U.S. patent application Ser. No. 13/838,777, titled "Active Drive Mechanism with Finite Range of Motion", filed on Mar. 15, 2013, issued as U.S. Pat. No. 9,408,669 on Aug. 9, 2016; U.S. patent application Ser. No. 13/835,136, titled "Active Drive Mechanism for Simultaneous Rotation and Translation", filed Mar. 15, 2013, now abandoned; U.S. patent application Ser. No. 13/803,535, titled "Active Drives for Robotic Catheter Manipulators", filed Mar. 14, 2015, issued as U.S. Pat. No. 9,326,822 on May 3, 2016, all of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the robotic medical devices field, and more specifically to new and useful devices, systems, and methods for controlling active drive systems.

BACKGROUND

For medical procedures, minimally invasive procedures are preferred over conventional techniques wherein the patient's body cavity is open to permit the surgeon's hands access to internal organs. Thus, there is a need for a highly controllable yet minimally sized system to facilitate imaging, diagnosis, and treatment of tissues which may lie deep within a patient, and which may be accessed via naturally-occurring pathways, such as blood vessels, other lumens, via surgically-created wounds of minimized size, or combinations thereof.

Currently known minimally invasive procedures for the treatment of cardiac, vascular, and other disease conditions use manually or robotically actuated instruments, which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc. Manually and robotically-navigated interventional systems and devices, such as steerable catheters, are well suited for performing a variety of minimally invasive procedures. Manually-navigated catheters generally have one or more handles extending from their proximal end with which the operator may steer the pertinent instrument. Robotically-navigated catheters may have a proximal interface configured to interface with a catheter driver comprising, for example, one or more motors configured to induce navigation of the catheter in response to computer-based automation commands input by the operator at a master input device in the form of a work station.

In the field of electrophysiology, robotic catheter navigation systems, such as the Sensei® Robotic Catheter System (manufactured by Hansen Medical, Inc.), have helped clinicians gain more catheter control that accurately translates the clinician's hand motions at the workstation to the catheter inside the patient's heart, reduce overall procedures (which can last up to four hours), and reduce radiation exposure due to fluoroscopic imaging necessary to observe the catheter relative to the patient anatomy, and in the case of electrophysiology, within the relevant chamber in the heart. The Sensei® Robotic Catheter System employs a steerable outer catheter and a steerable inner electrophysiology (EP) catheter, which can be manually introduced into the patient's heart in a conventional manner. The outer and inner catheters are arranged in an "over the wire" telescoping arrangement that work together to advance through the tortuous anatomy of the patient. The outer catheter, often referred to as a guiding sheath, provides a steerable pathway for the inner catheter. Proximal adapters on the outer guide sheath and inner EP catheter can then be connected to the catheter driver, after which the distal ends of the outer sheath and inner EP catheter can be robotically manipulated in the heart chamber within six degrees of freedom (axial, roll, and pitch for each) via operation of the Sensei® Robotic Catheter System.

While the Sensei® Robotic Catheter System is quite useful in performing robotic manipulations at the operational site of the patient, it is desirable to employ robotic catheter systems capable of allowing a physician to access various target sites within the human vascular system. In contrast to the Sensei® Robotic Catheter System, which may be used in conjunction with sheaths and catheters that are both axially and laterally rigid, robotic catheter systems designed to facilitate access to the desired target sites in the human vascular system require simultaneous articulation of the distal tip with continued insertion or retraction of an outer guide sheath and an inner catheter. As such, the outer guide sheath and inner catheter should be laterally flexible, but axially rigid to resist the high axial loads being applied to articulate the outer guide sheath or inner catheter, in order to track through the tortuous anatomy of the patient. In this scenario, the inner catheter, sometimes called the leader catheter extends beyond the outer sheath and is used to control and bend a guidewire that runs all the way through the leader catheter in an over-the-wire configuration. The inner catheter also works in conjunction with the outer guide sheath and guidewire in a telescoping motion to inchworm the catheter system through the tortuous anatomy. Once the guidewire has been positioned beyond the target anatomical location, the leader catheter is usually removed so that a therapeutic device can be passed through the steerable sheath and manually operated.

As shown in FIG. 1, robotic catheter systems typically employ a robotic instrument driver 1 to provide robotic insertion and refraction actuation, as well as robotic steering actuation, to a telescoping assembly of elongate flexible instruments. The instrument driver 1 comprises a housing 2 that contains motors (not shown) for providing the robotic actuators to the telescoping assembly, which may include an outer steerable guide sheath 3, an inner steerable leader catheter 4 disposed within the sheath catheter, and a conventional guidewire 5 disposed within the leader catheter 4.

The robotic instrument driver 1 may robotically insert/retract the leader catheter 4 relative to the sheath catheter 3. To this end, the proximal ends of the guide sheath 3 and leader catheter 4 are mechanically interfaced to the instrument driver 1 in such a manner that they may be axially translated relative to each other via operation of the motors, thereby effecting insertion or retraction movements of the respective guide sheath 3 and leader catheter 4. In the illustrated embodiment, the guide sheath 3 and leader catheter 4 respectively include proximal steering adapters 6, 7 ("splayers") mounted to associated mounting plates 8, 9 on a top portion of the instrument driver 1. In the illustrated embodiment, each of the proximal adapters 6, 7 can be actuated via motors (not shown) within the housing 2 of the instrument driver 1 to deflect or articulate the distal ends of the respective guide sheath 3 and leader catheter 4 in any direction.

Unlike the steerable guide sheath 3 and leader catheter 4, the distal ends of which can be robotically articulated via the instrument driver 1, the guidewire 5 is conventional, and thus, its distal end is not capable of being robotically articulated. Instead, as with most conventional guidewires, the guidewire 5 may be manipulated by inserting, retracting, or rolling or by simultaneously rolling while axially displacing the guidewire. In a non-robotic environment, such manipulations can be accomplished by pinching the proximal end of the guidewire between the forefinger and thumb of the physician and moving the forefinger relative to the thumb while axially displacing the guidewire.

In order to navigate the guide sheath 3 and leader catheter 4 through the tortuous anatomy of a patient, it is desirable that these components be laterally flexible. However, the flexibility of the leader catheter 4 may create issues when performing the robotic insertion actuation. In particular, due to the flexibility of the leader catheter 4 and the relatively long distance between the mounting plate 9 and the point at which the leader catheter 4 is contained within the guide sheath 3, the leader catheter 4 may buckle, thereby preventing it, or at least hindering it, from axially translating within the guide sheath 3. Although "passive" anti-buckling devices may be used to add lateral support to the leader catheter 4, thereby preventing the leader catheter 4 from buckling, these anti-buckling devices have length limitations and may be too cumbersome and time-consuming for medical personnel to install.

Furthermore, emulating a manual guidewire manipulation in a robotic catheter system is not a straightforward procedure. For example, although the instrument driver 1 illustrated in FIG. 1 can be designed to robotically insert/retract the guidewire 5 relative to the leader catheter 4 in the same manner in which the instrument 1 robotically inserts/retracts the leader catheter 4 relative to the guide sheath 3, such an arrangement may be impractical. In particular, the incorporation of an additional carriage within the housing 2 will disadvantageously increase the length of the instrument driver 1, which must accommodate the telescoping assembly when assuming a maximum retraction between the leader catheter 4 and guide sheath 3 and between the guidewire 5 and leader catheter 4. The increased size of the instrument driver 1 may be impractical and too big and heavy to be mounted on a table in a catheter lab environment. Thus, it is preferable that any drive device that inserts/retracts the guidewire 5 relative to the leader catheter 4 be immobile relative to the proximal end of the leader catheter 4, e.g., by locating it on the same mounting plate 9 that is associated with the leader catheter 4. This drive device must also be capable of rolling the guidewire 5.

Furthermore, the use of an additional carriage for the guidewire 5 would also require the installation of an additional "passive" anti-buckling device. Because medical personnel often exchange out guidewires that are as long as 300 cm in length, the use of a "passive" anti-buckling device not only may be tedious for medical personnel to install, the extended length of the anti-buckling device due to the length of the guidewire may render the anti-buckling device functionally impractical.

Additional complexities in emulating a manual guidewire manipulation in a robotic catheter system are slipping/buckling of the guidewire during manipulation and controlling or varying guidewire insertion/retraction speeds depending on the procedure or task. Guidewires may also exist in varying conditions, for example a guidewire may be wet with saline, or contaminated with blood or other bodily fluids. Many guidewires have hydrophilic coatings whose properties change with how dry or wet it is. In manual procedures, the doctor may adjust the grip on the wire to shorten it for higher force insertions to reduce risk of buckling. Alternatively, the doctor can lengthen the insertion strokes in times of low insertion force where increased speed is desirable. The doctor may also use a wet cloth or dry cloth to wet or dry the wire, respectively, to alter the coefficient of friction on the wire to help with insertion or retraction There, thus, remains a need to provide an improved instrument driver for a robotic catheter system that prevents a guidewire from buckling and improves the control of guidewire manipulation.

SUMMARY

One exemplary embodiment of controlling an active drive system includes a drive assembly having a first surface and a second surface for engaging an elongate member. The first and second surfaces may be attached to a drive mechanism to move the elongate member. The first surface may be slidable relative to the drive mechanism and may have a clearance between the drive mechanism and an end of the first surface during movement of the elongate member in a non-slip condition. A sensor may be associated with the first surface and may be configured to detect movement of the first surface in a slip condition.

In another exemplary embodiment, a drive system for an elongate member includes an active drive device and a computing device. The active drive device may include a first surface and a second surface arranged on an active drive mechanism for engaging the elongate member. The first surface may be axially slidable relative to the drive mechanism. A first sensor may be associated with the first surface, and a second sensor may be associated with the second surface, the sensors being configured to measure a force. The computing device may be in communication with the force sensors. The computing device may be configured to compare the first sensor measured force with the second sensor measured force to detect a slip occurrence in one direction when the second sensor measured force is not within a predetermined tolerance of the first sensor measured force.

In a further exemplary embodiment, a slip detection system on a drive system includes a first surface, a second surface, and a computing device. The first surface may be configured to drive an elongate member in an axial direction, and may include a first sensor configured to detect a force. The second surface may be axially movable relative to the drive system, and may have a second sensor configured to detect a force. The computing device may be configured to associate a threshold force with the second sensor, monitor the measured force on the second sensor, and compare the measured force of the second sensor with the threshold force to detect an initial slip occurrence between the active surface and the elongate member in response to exceeding a predetermined tolerance of the threshold force.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure. One of skill in the art will understand that each of the various aspects and features of the disclosure may advantageously be used separately in some instances, or in combination with other aspects and features of the disclosure in other instances.

DETAILED DESCRIPTION

The following description of the preferred embodiments of the invention is not intended to limit the disclosure to these preferred embodiments, but rather to enable any person skilled in the art to make and use the various embodiments described herein. Disclosed herein are devices, systems, and methods for implementing and controlling active drive systems, as well as managing and preventing slip of the guide wire.

Described herein are devices, systems and methods for controlling active drive systems and predicting and/or managing slip in active drive systems. In general, active drive systems for gripping and manipulating elongate members may include pad systems or roller systems. The pads or roller may have various diameters, widths, materials, or any other physical parameters. The elongate member may include a guidewire, a sheath, a leader, a catheter, an endoscope, or any type of flexible elongate medical instrument or tool. The terms guide wire and elongate member are used interchangeably herein and are meant to cover the various types of wires, sheaths, leaders, catheters, endoscopes or the like.

Active Drive Systems

Described below are four embodiments of active drive systems. In some embodiments, an active drive system may simultaneously insert/retract and roll an elongate member. Alternatively, an active drive system may insert/retract an elongate member independently of rolling the elongate member. An active drive system may include two or more rollers and/or two or more gripping pads for inserting, retracting, and rolling an elongate member.

Figure 1:
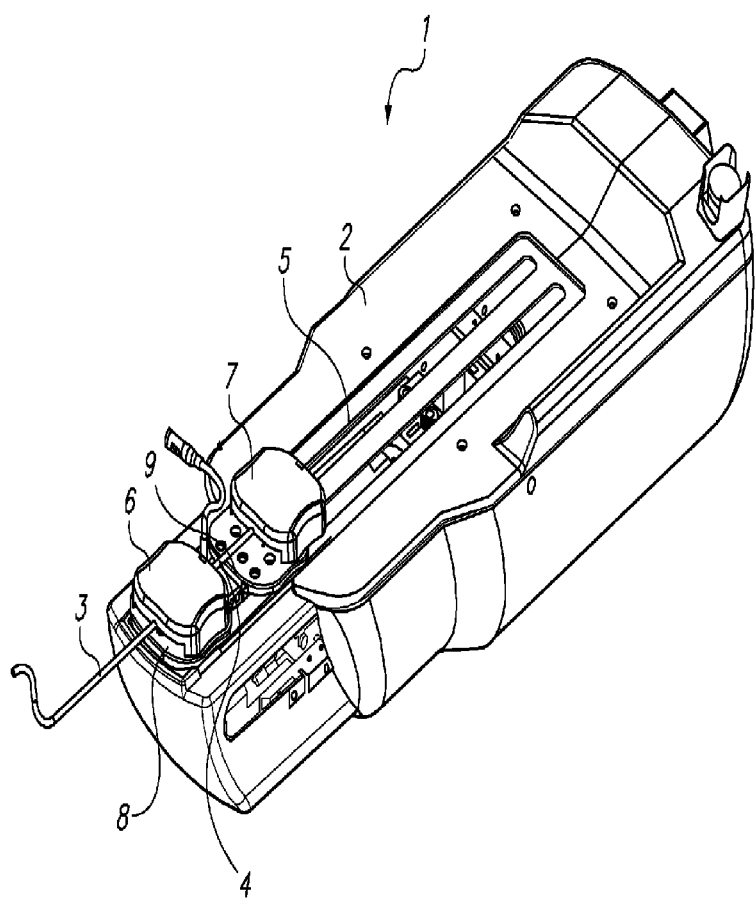
FIG. 1 illustrates a robotic catheter system in accordance with a preferred embodiment.

In some embodiments, an active drive system may be mounted to an instrument driver 1, as shown in FIG. 1. Alternatively, an active drive system may be mounted to a separate arm, revolute joint, housing, or apparatus for manipulation and/or maneuverability of the active drive system.

Active Drive Systems with Rollers

FIGS. 2A-6 illustrate a first embodiment of an active drive apparatus, as described in pending U.S. patent application Ser. No. 13/835,136, filed Mar. 13, 2013, now abandoned, which is herein incorporated by reference in its entirety. The drive apparatus 100 may function to provide continuous insertion/retraction and rotation to an elongate member. In some embodiments, the active drive apparatus may include a roller assembly and a roller support. In some embodiments, the roller assembly includes a first continuous surface, a second continuous surface, an open configuration for receiving an elongate member, and a closed configuration for securing the elongate member in the roller assembly. The roller assembly is configured to impart axial motion to the elongate member along the first continuous surface. In some embodiments, the first continuous surface maintains contact with the elongate member during the axial motion. In some embodiments, the roller support is configured to rotate the roller assembly about the second continuous surface, thereby imparting rotational motion to the elongate member. The second continuous surface maintains contact with the roller support during the rotational motion. As will be described in further detail below, the roller assembly imparts the axial motion and the roller support imparts the rotational motion independently of one another, such that a first one of the roller assembly and the roller support imparts its associated motion regardless of a degree of motion imparted by the other of the roller assembly and the roller support.

Figure 2A:
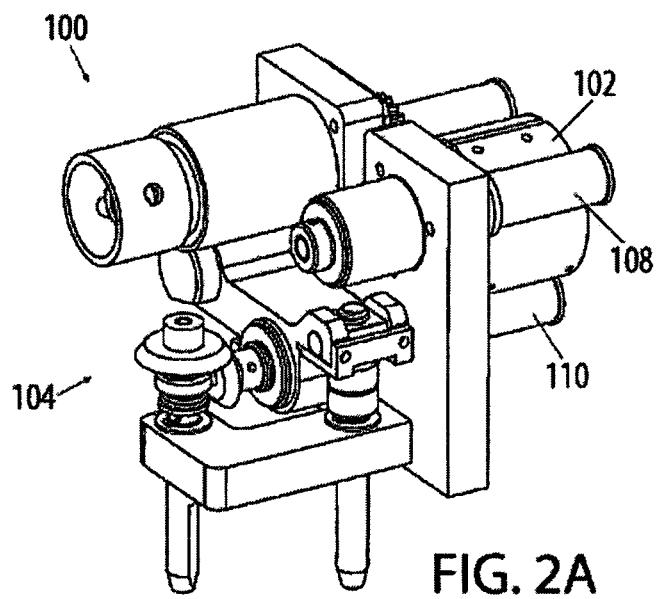
FIGS. 2A-6 illustrate perspective views of an active drive apparatus in accordance with a preferred embodiment.
Figure 2B:
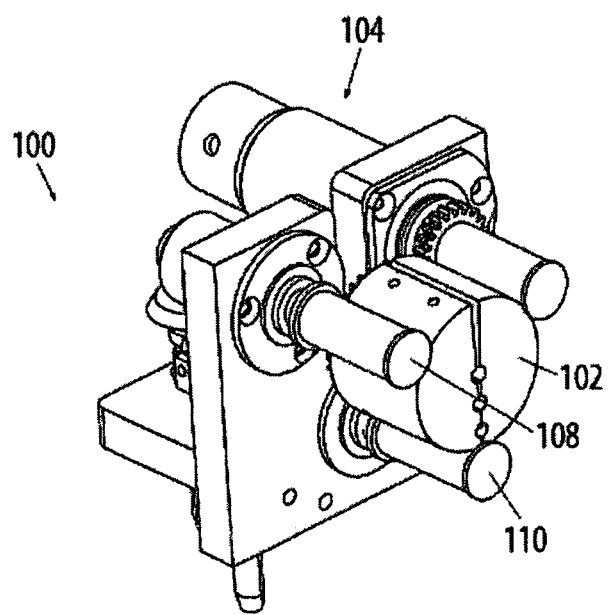
Figure 2C:
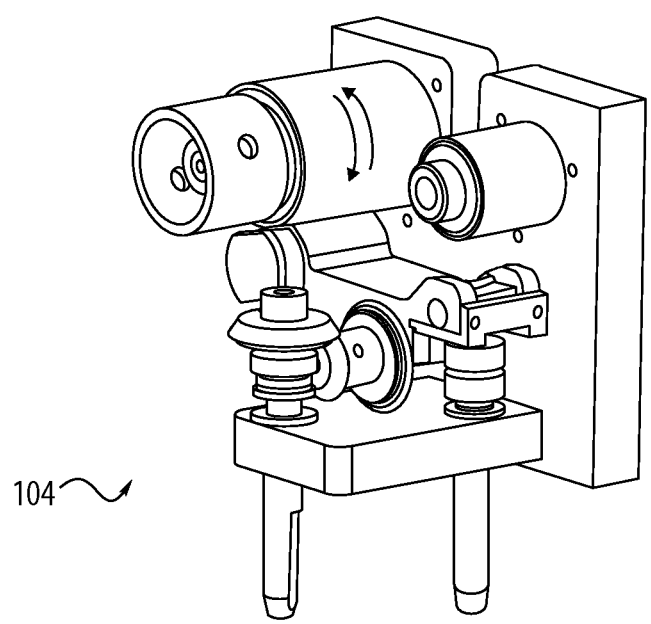
Figure 3:
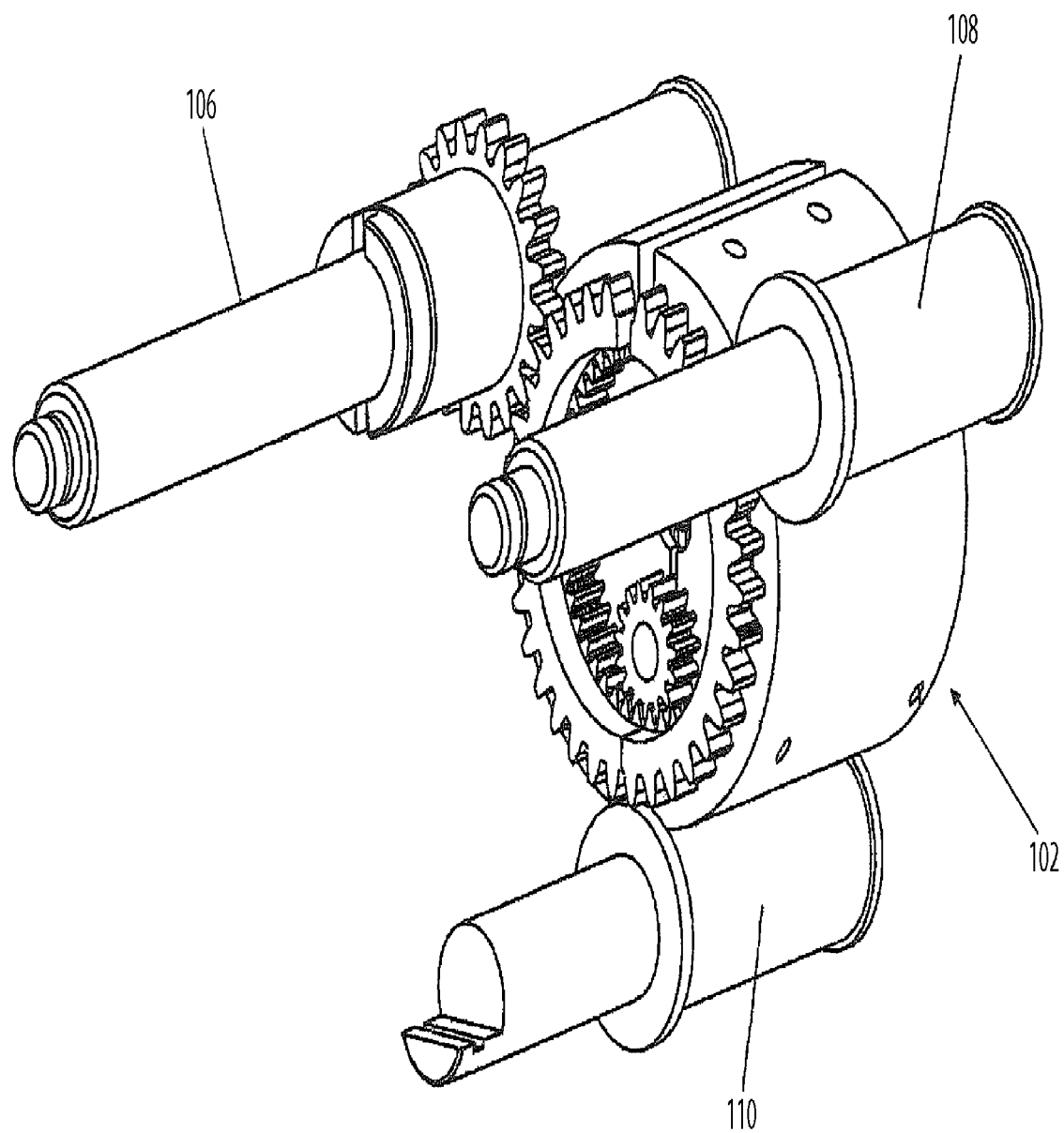

In some embodiments, as shown in FIGS. 2A and 2B, the drive apparatus 100 may further include a disposable mechanism 102 for contacting and driving an elongate member, such that the disposable mechanism includes the roller assembly. An associated drive mechanism 104 may generally be configured to be kept separate from the disposable mechanism 102, at least to an extent allowing the drive mechanism 104 to be kept out of a sterile environment associated with the elongate member and surgical procedure. As shown in FIGS. 2A-3, the disposable mechanism 102 may be supported between the roller support comprising two idle rollers 106, 108, and a driving roller 110 which is configured to rotate the disposable mechanism 102 about the second continuous surface to impart rotational motion to the elongate member.

Figure 4:
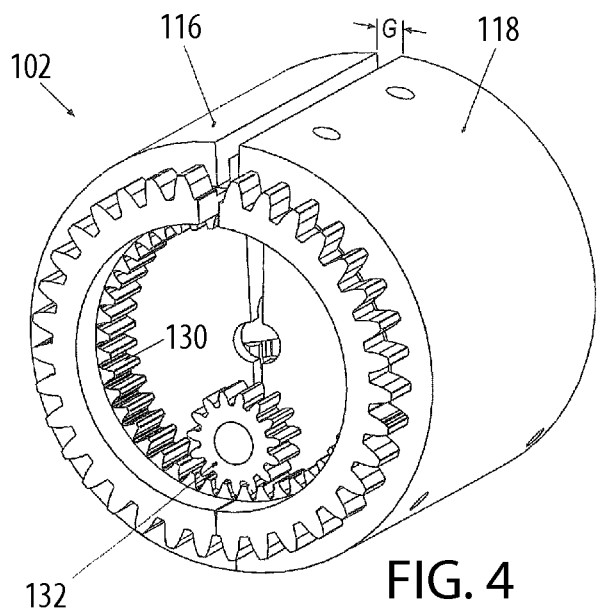
Figure 5:
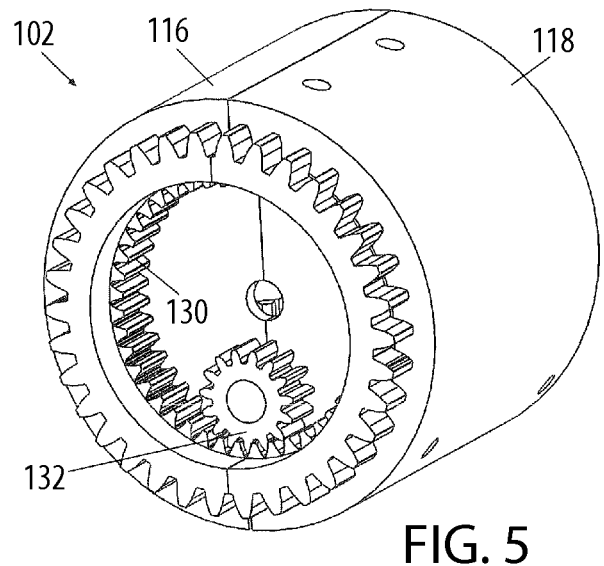
Figure 6:
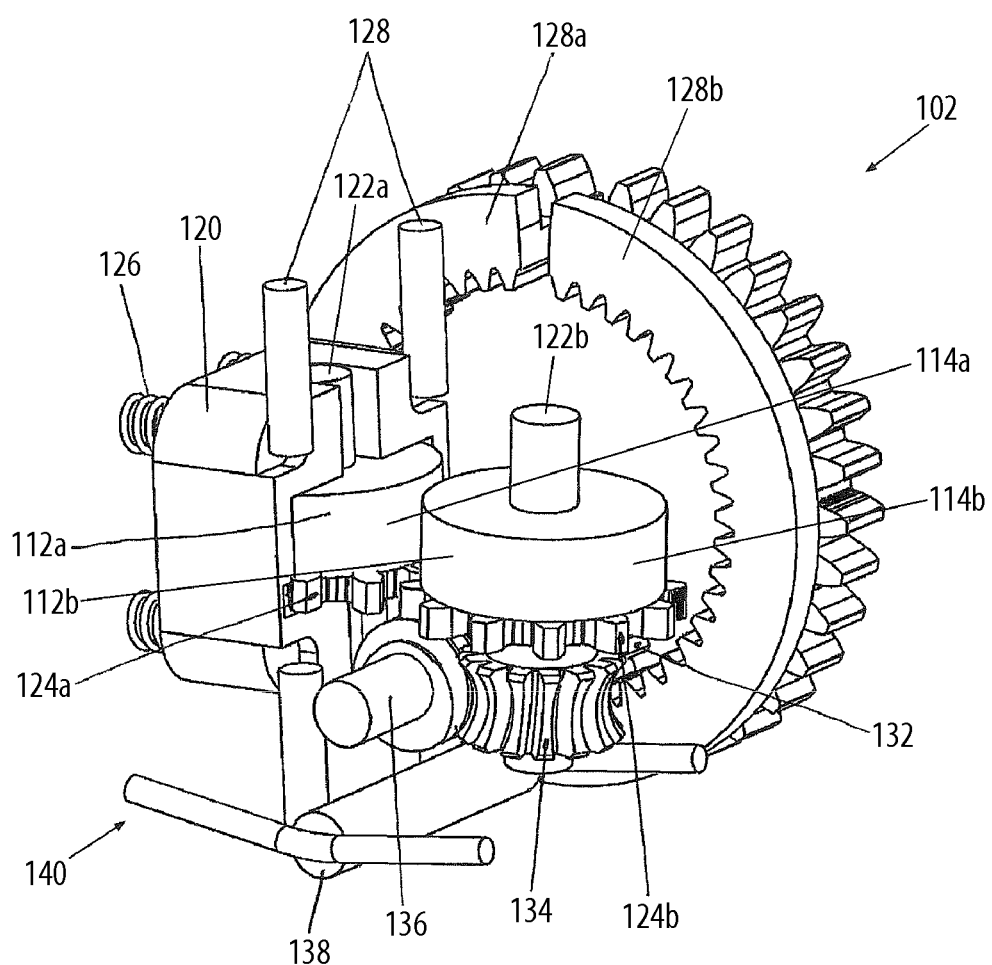

As shown in FIG. 6, the roller assembly includes one or more rollers 112 that are configured to impart axial motion to the elongate member along a first continuous surface. For example, as shown in FIG. 6, a first roller 112a and a second roller 112b each define generally cylindrical surfaces 114a, 114b that are configured to maintain contact with the elongate member during axial motion caused by rotation of the rollers 112. The drive apparatus 100 may further include a roller support configured to rotate the roller assembly to impart rotational motion to the elongate member. For example, as shown in FIGS. 4 and 5, the rollers 112 may generally be supported within the clamps 116, 118 of the disposable portion, for example via a saddle 120, as shown in FIG. 6, or by the clamps 116, 118 themselves, such that the rollers 112 may be rotated about an axis defined by the elongate member. It should be noted that while one set of rollers 112 is shown, multiple sets of rollers could be incorporated, for example in series, to provide additional traction on the elongate member for axial and rotational movement thereof. The clamps 116, 118 may be configured to receive an elongate member into gap G in the open configuration, as shown in FIG. 4, and to clamp or secure the elongate member in the closed configuration, as shown in FIG. 5.

Referring now to FIG. 6, the disposable mechanism 102 is illustrated with the left and right clamps 116, 118 removed. The disposable drive mechanism 102 includes a roller assembly including one or more rollers 112a, 112b for imparting axial motion to the elongate member. As shown in FIG. 6, two rollers 112a, 112b may be configured to receive an elongate member therebetween. More specifically, the rollers 112 may each rotate about corresponding spindles 122a, 122b. Moreover, as will be described further below, the rollers 112a, 112b may each have a plurality of geared teeth 124a, 124b which are meshingly engaged such that the rotation of the rollers 112a, 112b is generally coordinated. The rollers 112a, 112b may each be generally round, thereby defining respective continuous surfaces 114a, 114b about the generally cylindrical rollers 112 for engaging the elongate member. More specifically, an axial movement of any distance may be applied by the rollers 112a, 112b, since the rollers 112a, 112b may continuously turn about the spindles 122 without limitation. Accordingly, axial motion of the elongate member is not limited by any range of motion of any component of the drive apparatus 100, allowing the drive apparatus 100 to provide an axial movement in either direction of any magnitude while maintaining constant contact with the elongate member by way of the generally looped or continuous surfaces 114a, 114b of the rollers 112a, 112b.

The roller assembly may be supported in a roller support configured to rotate the rollers about an axis perpendicular to the spindles 122 of the rollers 112. For example, the spindle 122a of the roller 112a may be supported in a saddle 120 that is engaged with an interior surface of one of the clamps 116, 118 (not shown in FIG. 6) by way of a plurality of springs 126. Radially inward movement of the saddle 120 away from the interior surface may be limited by stop pins 128, which may engage an interior side of the saddle 120 to generally limit radially inward movement of the saddle 120 and the roller 112a, thereby limiting force applied by the roller 112a to the elongate member when the elongate member is positioned between the rollers 112a, 112b. The spindle 122b of the other roller 12b may be supported in the corresponding one of the clamps 116, 118 (not shown in FIG. 6). Accordingly, the spindle 122b may be generally fixed within the clamps 116, 118 while the spindle 122a may be movable by way of the springs 126 to provide a clamping force upon the elongate member.

The disposable device 102 may further comprise gear halves 128a, 128b which define an inner toothed surface 130 engaging a drive pinion 132, as shown in FIGS. 4 and 5. The drive pinion 132 may be engaged with a worm gear 134 by way of worm 136, wherein the worm 136 is fixed for rotation with the drive pinion 132. A location shaft 138 may be provided to assist with locating the above components within the clamps 116, 118, as will be described further below. Additionally, a compliant element 140 may be provided which generally provides a spring force urging the clamps 116, 118 toward an open position, as shown in FIG. 4.

Active Drive Systems with Pads/Grippers

FIGS. 7-10 illustrate a second alternative embodiment of an active drive mechanism, for example an active catheter feeder 200, as described in pending U.S. patent application Ser. No. 13/803,535, filed Mar. 14, 2013, which is herein incorporated by reference in its entirety. The catheter feeder 200 is designed to mimic the manual finger feed method that physicians may use to advance/retract the leader catheter within the guide sheath, and in particular, the grip, push, release, retracting, and repeating movements performed by the fingers of the physician to incrementally advance the leader catheter, and the grip, pull, release, advancing, and repeating movements performed by the fingers of the physician to incrementally retract the leader catheter.

Figure 7:
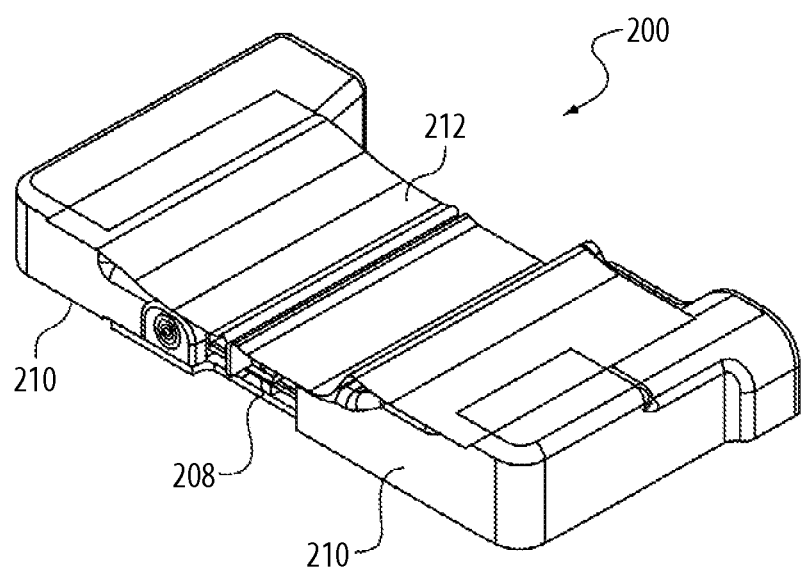
FIGS. 7-10 illustrate perspective and elevation views of an active drive apparatus in accordance with an alternative preferred embodiment.
Figure 8:
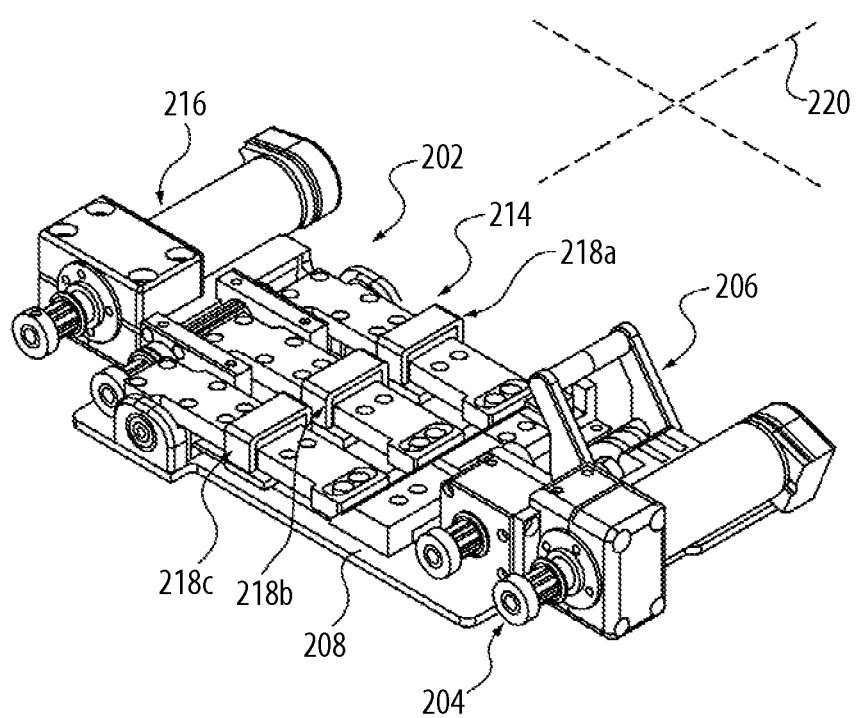

As shown in FIGS. 7-8, the catheter feeder 200 generally comprises a feeder assembly 202 configured for advancing/retracting the leader catheter within the guide sheath, a grip adjustment assembly 204 configured for adjusting the grip of the feeder assembly 202, a loading/unloading assembly 206 configured for allowing the leader catheter to be top-loaded and unloaded from the active catheter feeder 200, a base plate 208 on which the feeder assembly 202 and grip adjustment assembly 204 are mounted, a housing 210 mounted to the base plate 208 over the feeder assembly 202 and grip adjustment assembly 204, and a drape 212 configured for isolating the disposable components of the catheter feeder 200 from the sterile field. The feeder assembly 202 generally comprises a grip assembly arrangement 214 configured for performing advancing/retracting movements of the leader catheter, and a driver assembly 216 configured for actuating the grip assembly arrangement 214 to perform these movements.

Referring further to FIG. 8, the grip assembly arrangement 214 includes three grip assemblies 218a, 218b, 218c configured for being independently translated relative to the base plate 208 parallel to a longitudinal axis 220 in a reciprocal manner. To this end, the grip assemblies 218 are slidably engaged with each other in a nested arrangement. In order to guide independent translation of the grip assemblies 218 along the longitudinal axis 220, the grip assembly arrangement 214 further includes a parallel pair of rails mounted to the base plate 208 along the longitudinal axis 220.

Figure 9:
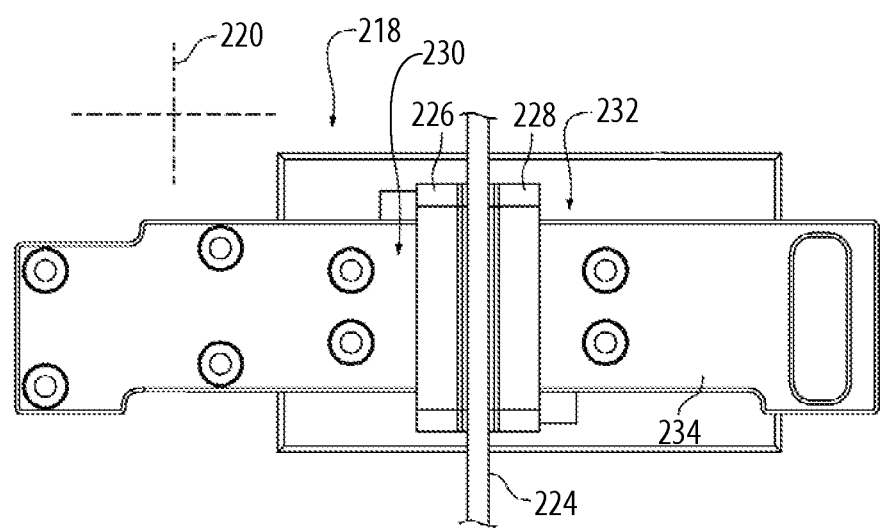
Figure 10:
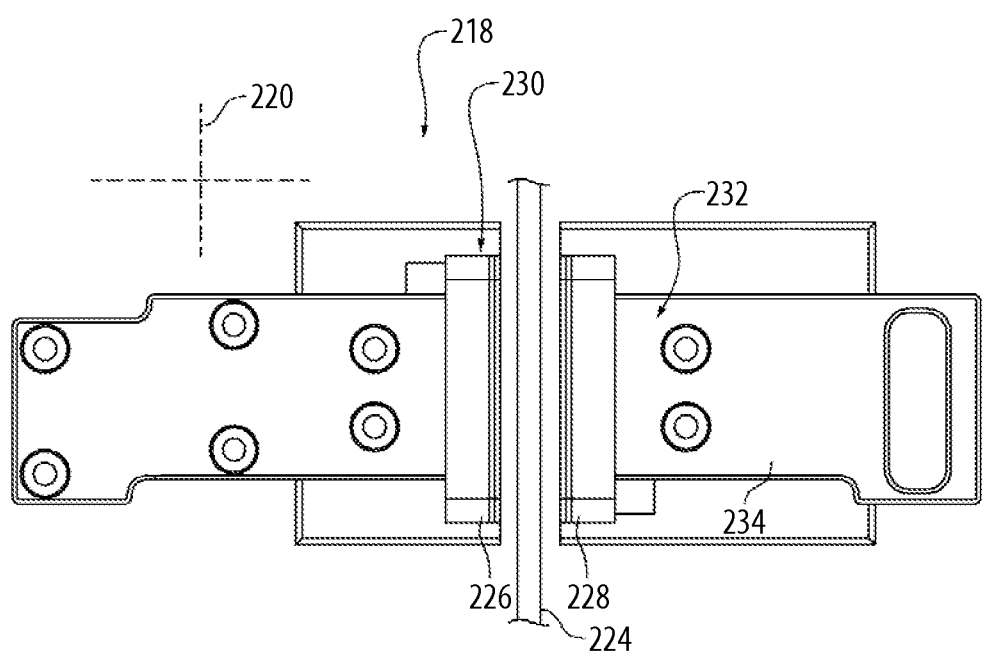

As shown in FIGS. 9 and 10, the grip assembly 218 is configured for being alternately closed (FIG. 9) to grip the catheter body 224 between the respective gripping pads 226, 228 of the first and second grippers 230, 232, and opened (FIG. 10) to release the catheter body 224 from between the respective gripping pads 226, 228 of the first and second grippers 230, 232. For the purposes of this specification, a grip assembly is closed at the point where the gripping pads 226, 228 are closest to each other, and is open at the point where the gripping pads 226, 228 are furthest from each other (after the second grippers 232 are adjusted to a fixed position by the grip adjustment assembly 204 using grip actuator 234). The grip assembly 218 is designed in a manner that the catheter body 224 is only gripped when the grip assembly 218 is in the closed position, and the catheter body 224 is released when the grip assembly 218 is in the opened position or transitioning between the closed position and the opened position. Furthermore, the grip adjustment assembly 204, as shown in FIG. 8, can be operated to adjust the strength that the grip assembly 218 grips the catheter body 224 between the gripping pads 226, 228.

In the third and fourth alternative embodiments described below, axial and rotational motion of the elongate member may be governed by independent drive systems associated with the drive apparatus. For example, a dynamic gripper may have separate motors or mechanisms controlling axial motion on the one hand and rotational motion on the other. Accordingly, insertion and rotation of the elongate member may be accomplished completely independently of the other. More specifically, the elongate member may be inserted axially while it is being rotated, or the elongate member may be inserted without any rotation. Moreover, the elongate member may be rotated without requiring any insertion motion at the same time.

FIGS. 11-16 illustrate a third alternative embodiment of an active drive device 300, as described in pending U.S. patent application Ser. No. 13/838,777, filed Mar. 15, 2013, issued as U.S. Pat. No. 9,408,669 on Aug. 9, 2016, herein incorporated by reference in its entirety. In the illustrated example, the drive apparatus includes a static gripper 302, and a dynamic gripper 304. In some embodiments, the static gripper 302 may be generally fixed with respect to a support surface 306. Each of the grippers 302, 304 may comprise a clamp 308, 310 having a pair of opposing pads 312a, 312b and 314a, 314b, respectively. Accordingly, the grippers 302, 304 may each selectively clamp an elongate member, e.g., a guidewire or catheter, between their respective opposing pads 312a, 312b and 314a, 314b. The dynamic gripper 304 may have a range of motion to which it is confined. For example, the dynamic gripper 304 may be capable of axial movement in a direction A along a distance D. Additionally, the dynamic gripper 304 may be capable of limited rotational movement about an axis parallel to the direction of axial movement, for example to a range of plus or minus a predetermined angle with respect to a normal or center position. The dynamic gripper 304 may move an elongate member across a predetermined movement, for example an axial or rotational movement that may be provided by a user that is greater than the axial or rotational range of motion.

Figure 11:
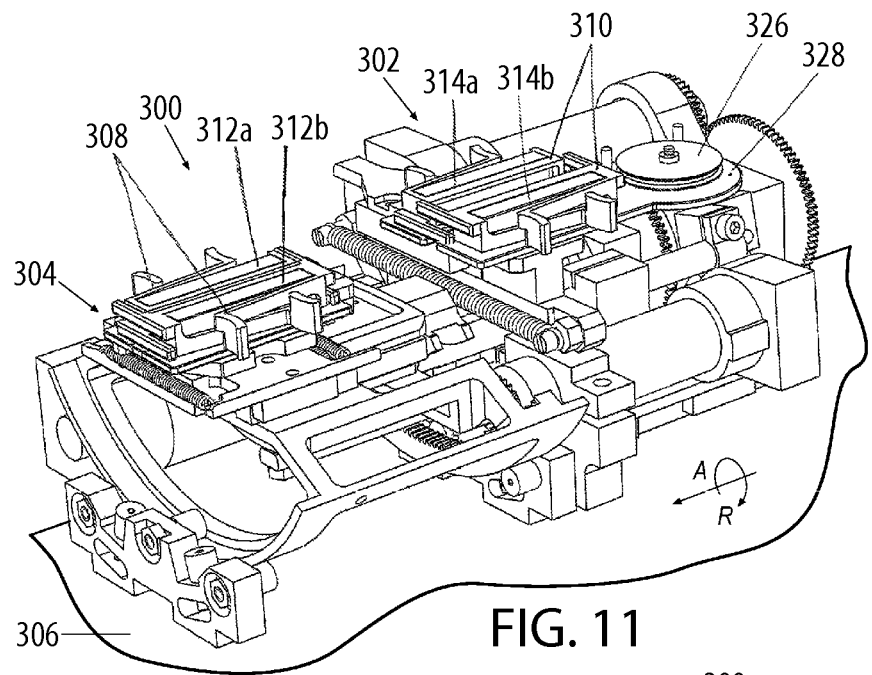
FIGS. 11-16 illustrate perspective, plan, and cross sectional views of an active drive apparatus in accordance with an alternative preferred embodiment.
Figure 12:
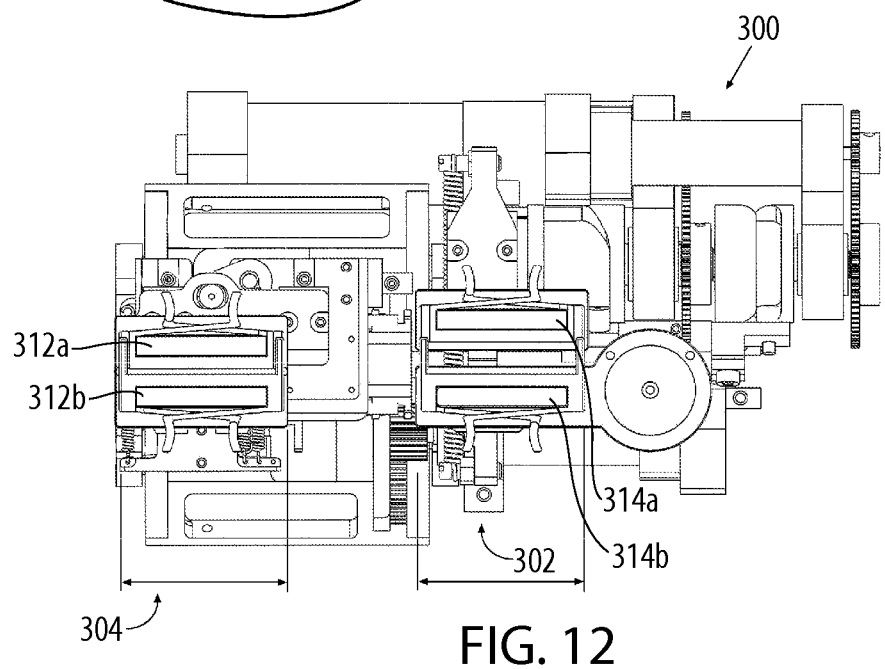

As shown in FIG. 11, the grippers may each be mounted to the support structure 306, for example a top surface or support structure associated with the instrument driver. The dynamic gripper 304 is configured to generally move axially and rotationally with respect to the support structure 306 to effect a corresponding axial and rotational movement of the elongate member. By contrast, the static gripper 302 is generally not movable axially or rotationally with respect to the support structure 306. The static gripper 302 selectively closes and opens to grip and release the elongate member. In some embodiments, the static gripper 302 cooperates with the dynamic gripper 304 to effect axial movement (i.e., for insertion) along a direction A as illustrated in FIG. 1, and rotational movement R about the direction A of the elongate member. The grippers 302, 304 may generally work in sequence such that at least one of the grippers 302, 304 is gripping the elongate member at any given time. More specifically, during any movement of the guidewire, for example insertion, retraction, or rotational movement in either direction, the dynamic grippers 304 are closed, and static grippers 302 are open.

Figure 13:
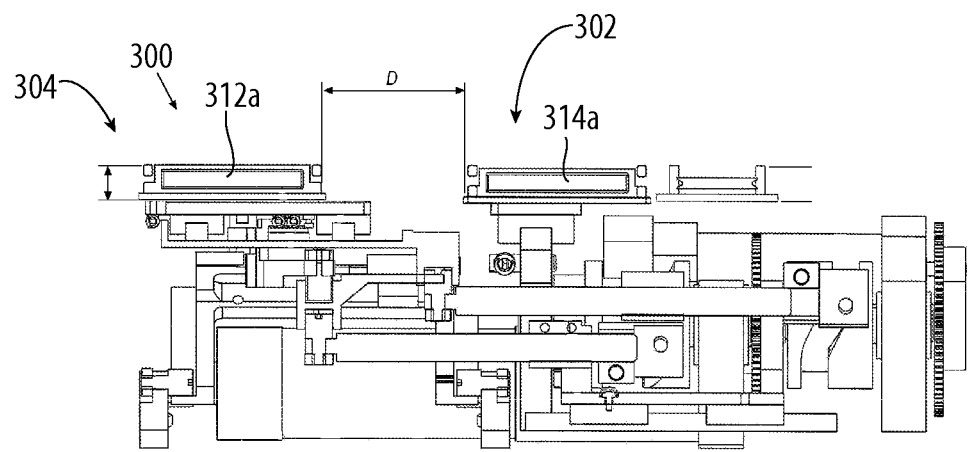
Figure 14:
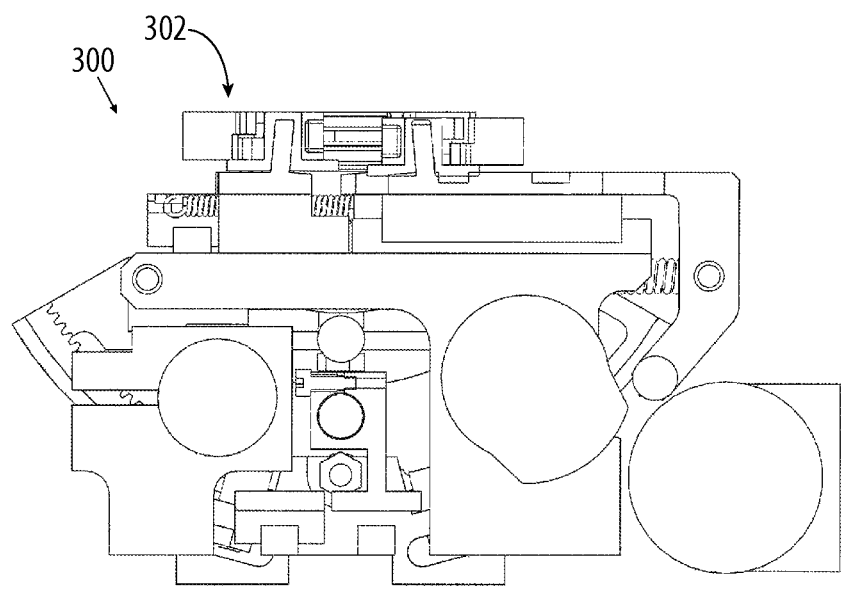

A range of axial motion associated with the dynamic grippers 304 may be finite, and in particular be limited to a predetermined axial distance D, as shown in FIG. 13. Accordingly, upon reaching a limit to the range of motion, for example at an axially furthest position in one direction, the dynamic grippers 304 generally release the elongate member, move back in an opposite direction, and re-grip the elongate member for continued axial movement. While the dynamic grippers 304 are not gripping the elongate member, the static grippers 302 may hold the elongate member in place to prevent movement or loss of position. Further, the static and dynamic grippers 302, 304 may each be configured to open to allow loading of an elongate member.

Figure 15:
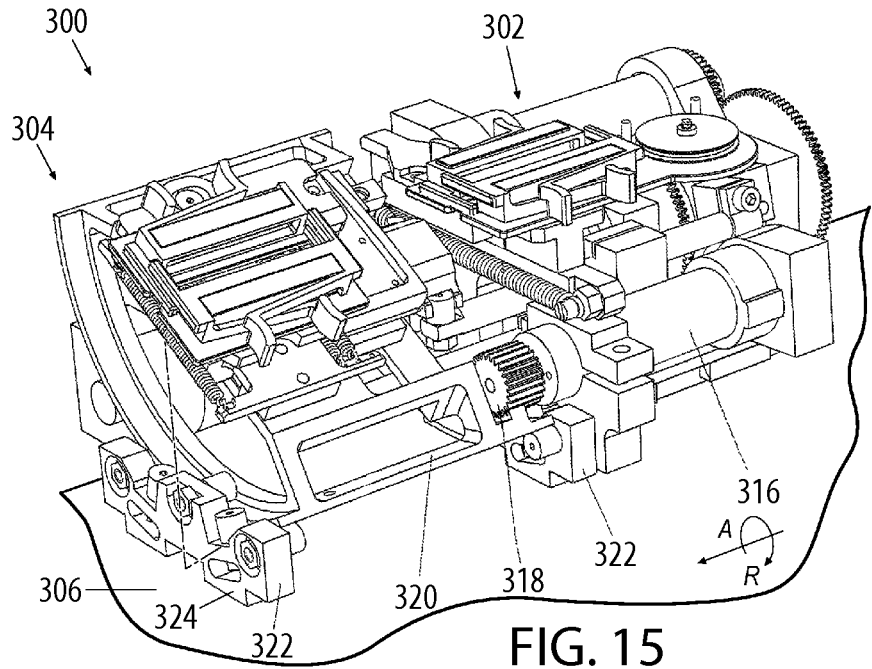
Figure 16:
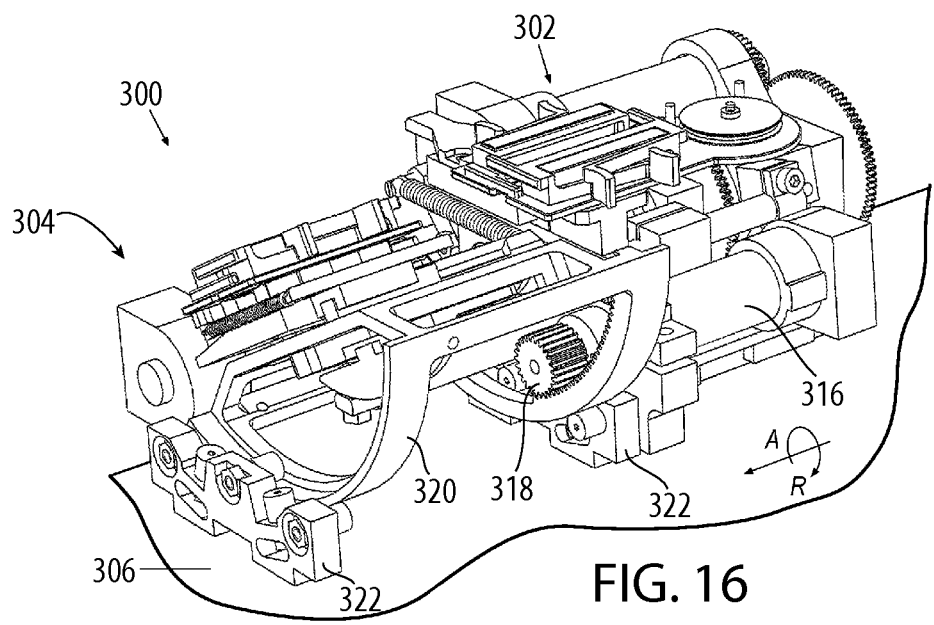

Turning now to FIGS. 15 and 16, rotational motion of the dynamic grippers 304 is described and shown in further detail. A rotation drive motor 316, as best seen in FIG. 15, may rotate a gear 318 engaging a carriage or swing platform 320 configured to rotate about an axis of rotation, for example in a rotational motion R about the direction of insertion A. The carriage 320 may be located by a pair of rolling posts 322 supported by a base structure 324. The base structure 324 may in turn be secured to the support structure 306. The carriage or swing platform 320 may be capable of rolling from a nominal or center position to any degree that is convenient.

FIGS. 17-21 illustrate a fourth alternative embodiment of an active drive apparatus 400, as described in pending U.S. patent application Ser. No. 13/838,777, filed Mar. 15, 2013, issued as U.S. Pat. No. 9,408,669 on Aug. 9, 2016, herein incorporated by reference in its entirety. The drive apparatus 400 may generally include a dynamic gripper 404 and two static grippers 402a, 402b. The dynamic gripper 404 may comprise a pair of opposing pads 406, 408. Similarly, the first static gripper 402a may comprise a pair of opposing pads 410a, 412a, and the second static gripper 402b may also comprise a pair of opposing pads 410b, 412b. Accordingly, the grippers 404, 402a, and 402b may each selectively grip an elongate member between their respective opposing pads 406/408, 410a/412a, and 410b/412b. The pads 406/408, 410a/412a, and 410b/412b may each be relatively soft with respect to the particular elongate member being employed, in order to more securely grip the elongate member and minimize potential damage to the elongate member, for example by spreading grip load across an increased surface area of the elongate member.

Figure 17:
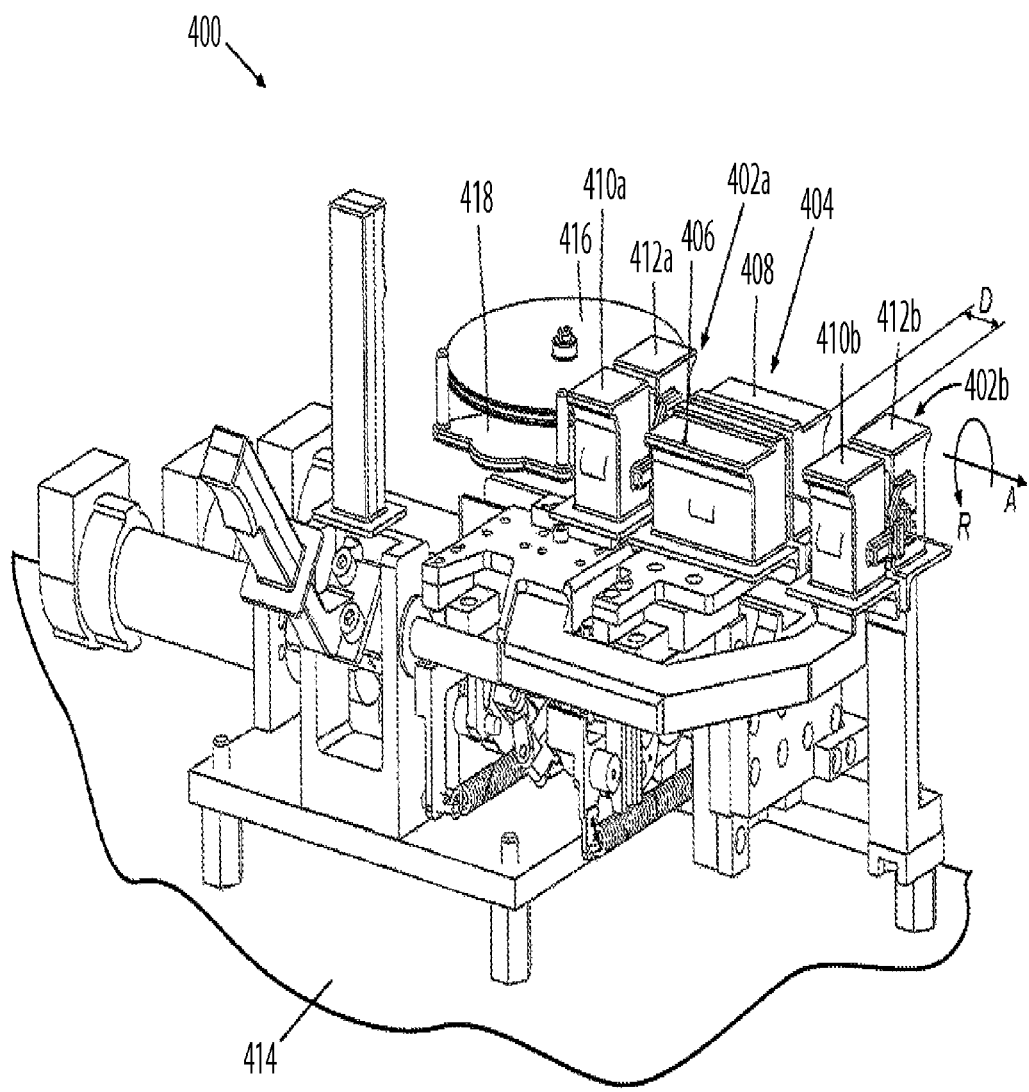
FIGS. 17-21 illustrate perspective and cross sectional views of an active drive apparatus in accordance with an alternative preferred embodiment.
Figure 18:
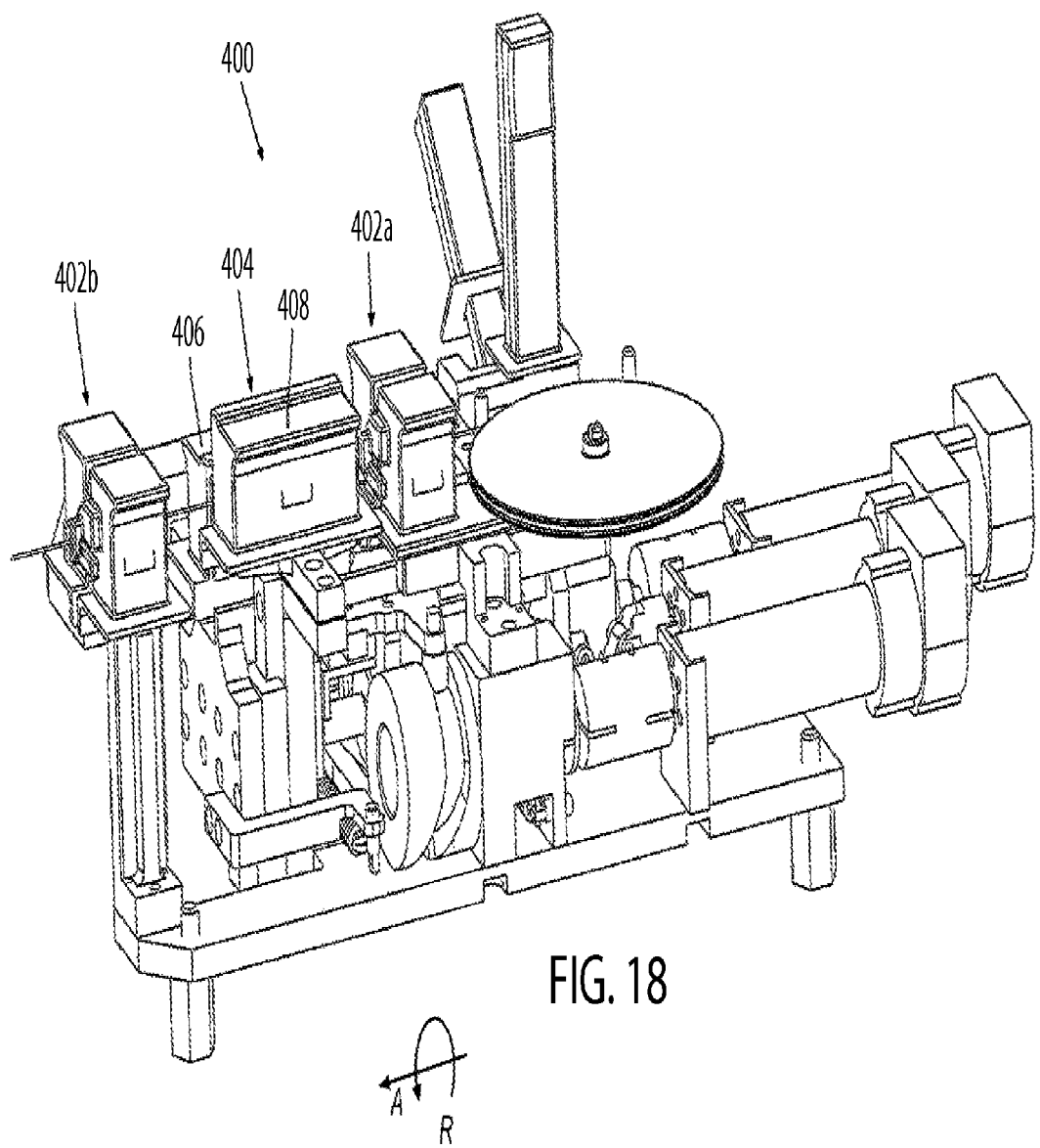
Figure 19:
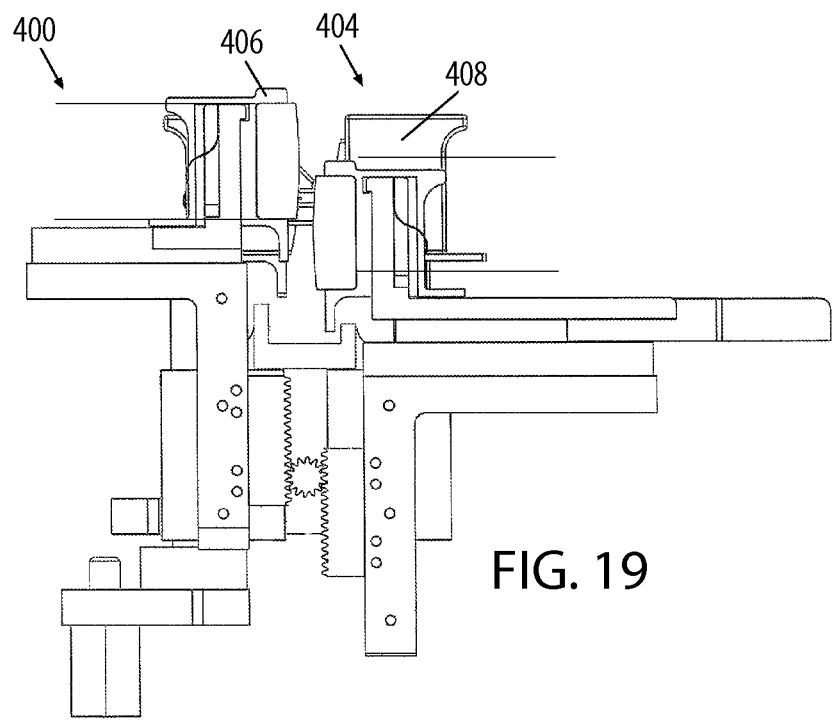
Figure 20:
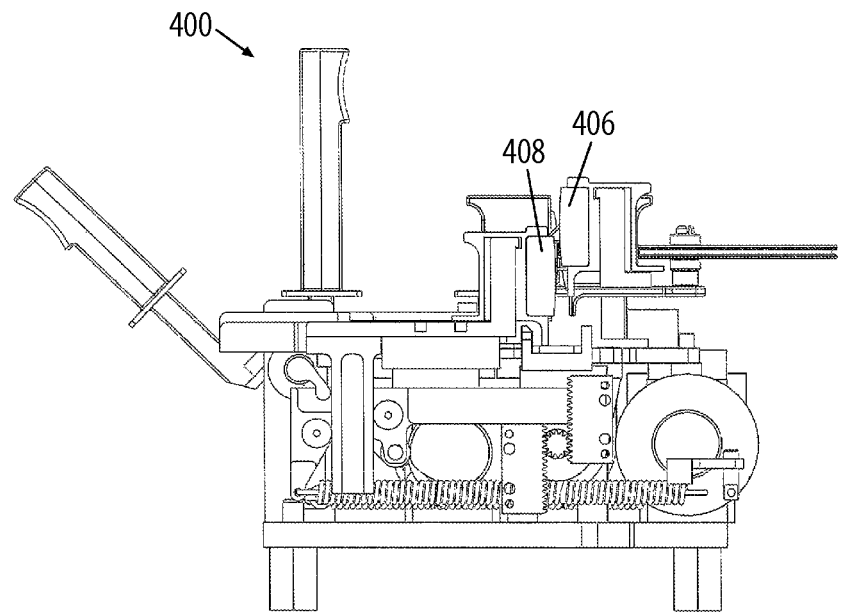
Figure 21:
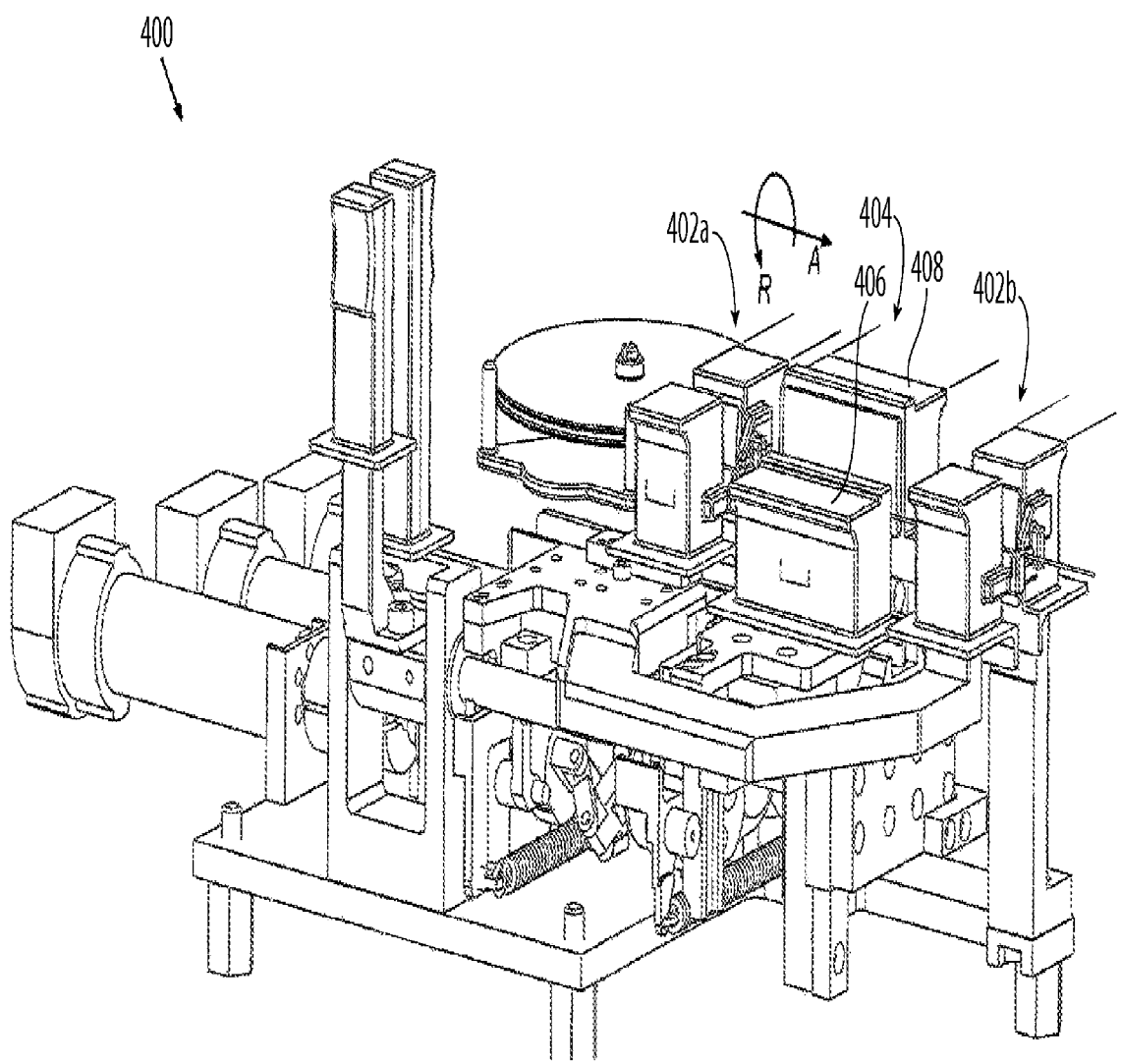

As shown in FIG. 17, the static grippers 402a, 402b and dynamic gripper 404 may each be mounted to a support structure 414, for example a top surface or support structure associated with the instrument driver. The dynamic gripper 404 is configured to generally move axially with respect to the support structure 414 to effect a corresponding axial movement of the elongate member. The pads 406, 408 of the dynamic gripper 404 are also configured to translate in a vertical direction across a fixed range of motion to impart rotational motion to the elongate member with respect to the support structure 414. By contrast, the static grippers 402a and 402b are generally not movable axially or rotationally with respect to the support structure 414. The static grippers 402a and 402b selectively close and open to grip and release the elongate member.

Generally, similar to the drive apparatus 300 described above, the static grippers 402a and 402b of the drive apparatus 400 each cooperate with the dynamic gripper 404 to effect axial movement (i.e., for insertion or retraction) along a direction A, as illustrated in FIG. 17, and rotational movement R about the direction A of the elongate member. The static grippers 402a, 402b may generally work in sequence with the dynamic grippers 404 such that at least one of the grippers 404, 402a, and 402b is gripping the elongate member at any given time. More specifically, during any movement of the guidewire, e.g., insertion, retraction, or rotational movement in either direction, the dynamic grippers 404 are closed, and the static grippers 402a and 402b are open. Moreover, the static grippers 402a, 402b may generally work in concert, such that the static grippers 402a. 402b are either both open or closed.

A range of axial motion associated with the dynamic grippers 404 may be finite, and in particular be limited to a predetermined axial distance $D_2$, as seen in FIG. 17. In the illustrated example having two static grippers 402a, 402b, a range of motion of the dynamic gripper 404 may be limited by the static gripper 402a on one end and the other static gripper 402b on the other end. However, as noted above, in other embodiments, only one static gripper 402 may be present, and thus the axial motion of the dynamic gripper 404 may be limited by other factors. Nevertheless, the dynamic gripper 404 may have some predetermined range of axial motion. Accordingly, upon reaching a limit to the range of motion at an axially furthest position in one direction, the dynamic grippers 404 generally release the elongate member, move back in an opposite direction, and re-grip the elongate member for continued axial movement. While the dynamic grippers 404 are not gripping the elongate member, the static grippers 402a and/or 402b may hold the elongate member in place to prevent movement of the elongate member or loss of position. This synchronization of the movement of the dynamic and static grippers is described in further detail below in the section "Synchronizing and Aligning Active Drive Motors."

Pads 406 and 408 may be designed to optimize the gripping and rolling performance of the elongate member. For example, in one embodiment, a high durometer material that does not engulf the elongate member is used, which may generally prevent pads 406 and 408 from contacting each other. This ensures that the spring force closing the grippers is substantially entirely applied to the elongate member and is not transferred from one gripper to the other, ensuring reliable grip on the elongate member. In another embodiment, the contact surface of the pads 406 and 408 is beveled in a convex shape such that there is less chance that the pads will contact each other due to any misalignment or non-parallelism in the gripper mechanism. Different pad materials and configurations will be described in further detail below in the section "Active Drive System Enhancements."

During axial movement of the elongate member and also during rotational movement, the dynamic pads 406 and 408 are generally closed, thereby trapping the elongate member there between as a result of a grip imparted to the elongate member. Additionally, during axial or rotational motion of the elongate member, the pads 410a, 412a of the first static gripper 402a and the pads 410b, 412b of the second static gripper 402b remain open, thereby generally freely allowing relative movement of the elongate member with respect to the static grippers 402a, 402b. Upon reaching a limit of rotational or axial motion, the pads 410a, 412a of the first static gripper 402a and the pads 410b, 412b of the second static gripper 402b may be closed. The pads 406 and 408 of the dynamic gripper 404 may then be opened, and moved within its range of motion (i.e., along distance D) to allow regripping of the elongate member, while the static grippers 402a, 402b maintain the axial and rotational position of the elongate member. The cycle may then be repeated to allow further axial and/or rotational movement of the elongate member.

In some embodiments of active drive devices described above, an elongate member may be wrapped at least partially about a slip detection wheel 326, as shown in FIG. 11, or 416, as shown in FIG. 17, that passively rotates in response to a length of the guidewire being moved by the dynamic grippers 304,404, respectively. The slip detection wheel 326/416 may be mounted on a rotatable member 328/418. Moreover, as will be described further below, the wheel 326/416 may include optical marks allowing for tracking of the wheel 326/416 rotation, thereby allowing measurement of movement and/or slippage of the elongate member.

Active Drive Systems Enhancements

Figure 22:
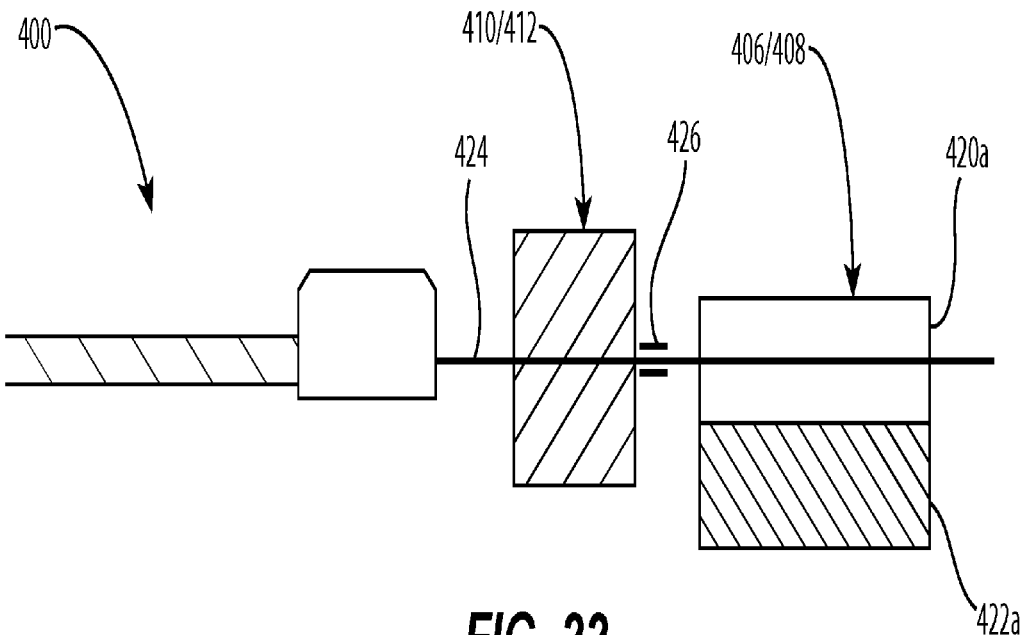
FIGS. 22 and 23 illustrate pad surfaces of a dynamic gripper of an active drive apparatus in accordance with a preferred embodiment.
Figure 23:
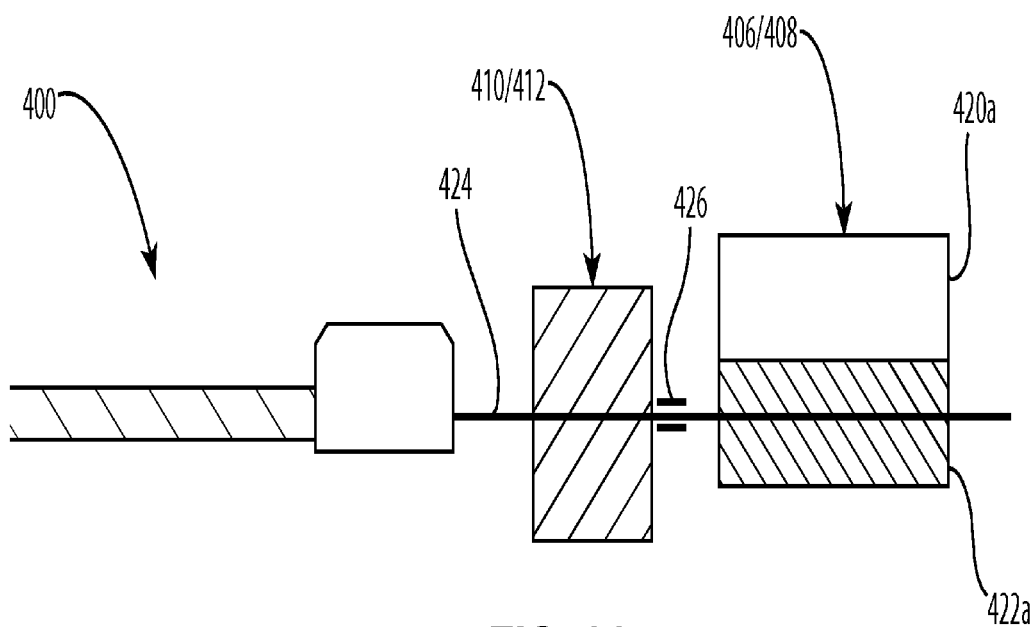

In some embodiments described above, the active drive system may include pads coupled to grippers configured for manipulating elongate members of various sizes, diameters, or configurations. For example, as shown in FIGS. 22-23, the pads of an active drive system 400 may include multi-durometer pad sections 420, 422 configured to manipulate smaller and larger elongate members 424, respectively. The multi-durometer pad sections may manipulate elongate members including a diameter between 0.250 inches and 0.010 inches or any subrange therebetween, For example, an elongate member diameter may include 0.150 inches, 0.035 inches, 0.025 inches, 0.020 inches, 0.018 inches, 0.014 inches, less than 0.014 inches, or any diameter suitable to the application. To accommodate for various sizes, the drive apparatus may further be configured to receive a user input allowing selection of a size of the elongate member 424 or may automatically detect a size of the elongate member 424 using one or more sensors, for example optical sensors.

As shown in FIGS. 22-23, pad 406/408 may include pad section 420a (e.g., shown as an upper section) made of a harder durometer material and pad section 422a (e.g., shown as a lower section) made of a softer durometer material. Depending on the size of the elongate member 424 to be manipulated, pad 406/408 may be oriented in a first configuration, as shown in FIG. 22, with a central portion of the selected pad section 420a aligned with an eyelet 426 of a central portion of pad 410/412, for example providing a harder durometer pad surface for smaller wires or catheters. For another size elongate member 424, pad 406/408 may be oriented in a second configuration, as shown in FIG. 23, with a central portion of pad section 422a aligned with eyelet 426, for example providing a softer durometer pad surface for larger wires or catheters. Thus, depending on the determined size of the elongate member 424, the drive apparatus 400 may align either pad section 420a or 422a with eyelet 426 for receipt of elongate member 424.

Figure 24:
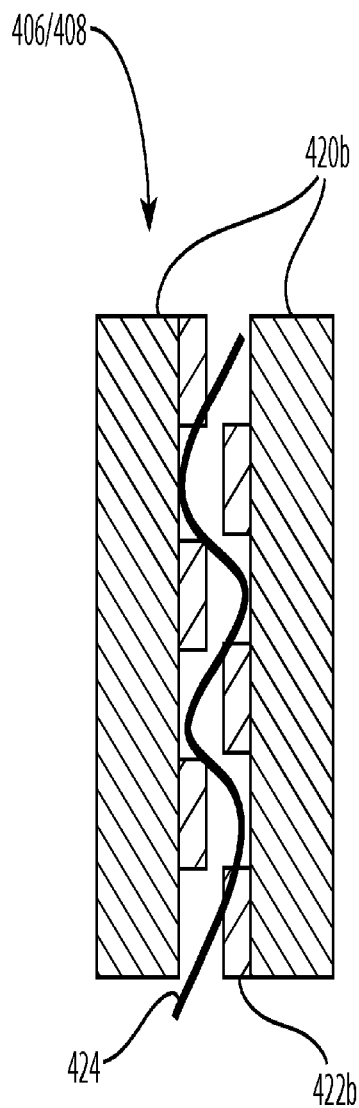
FIGS. 24 and 25 illustrate pad surfaces of a dynamic gripper of an active drive apparatus in accordance with an alternative preferred embodiment.
Figure 25:
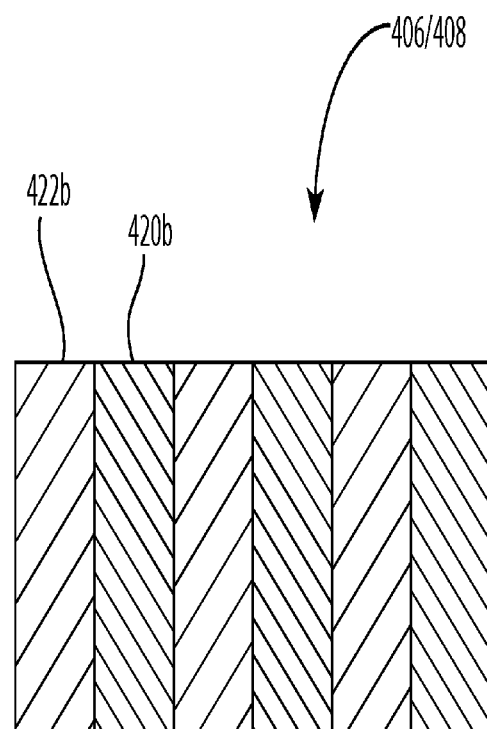

As shown in FIGS. 24-25, pad 406/408 may be patterned with strips of interlocking and alternating pad sections 420b and 422b, for example where pad sections 422b are raised (e.g., configured as teeth). In an engaged configuration as shown in FIG. 24, pads 406/408 may create a mechanical lock on elongate member 424 to increase grip during insertion or retraction of elongate member 424. The strips may be configured as teeth that are dimensioned and spaced such that a smaller (e.g., 0.014 inch diameter) elongate member 424 contacts pad sections 420b and 422b (e.g., harder and softer durometer sections) while a larger (e.g., 0.035 inch diameter) elongate member 424 will primarily contact pad sections 422b (e.g., softer durometer). The strips may further be dimensioned and spaced to reduce kinking of elongate member 424. Thus, this may allow for rolling of smaller wires without encapsulation while maintaining grip for insertion of larger elongate members 424.

Figures 26, 27:
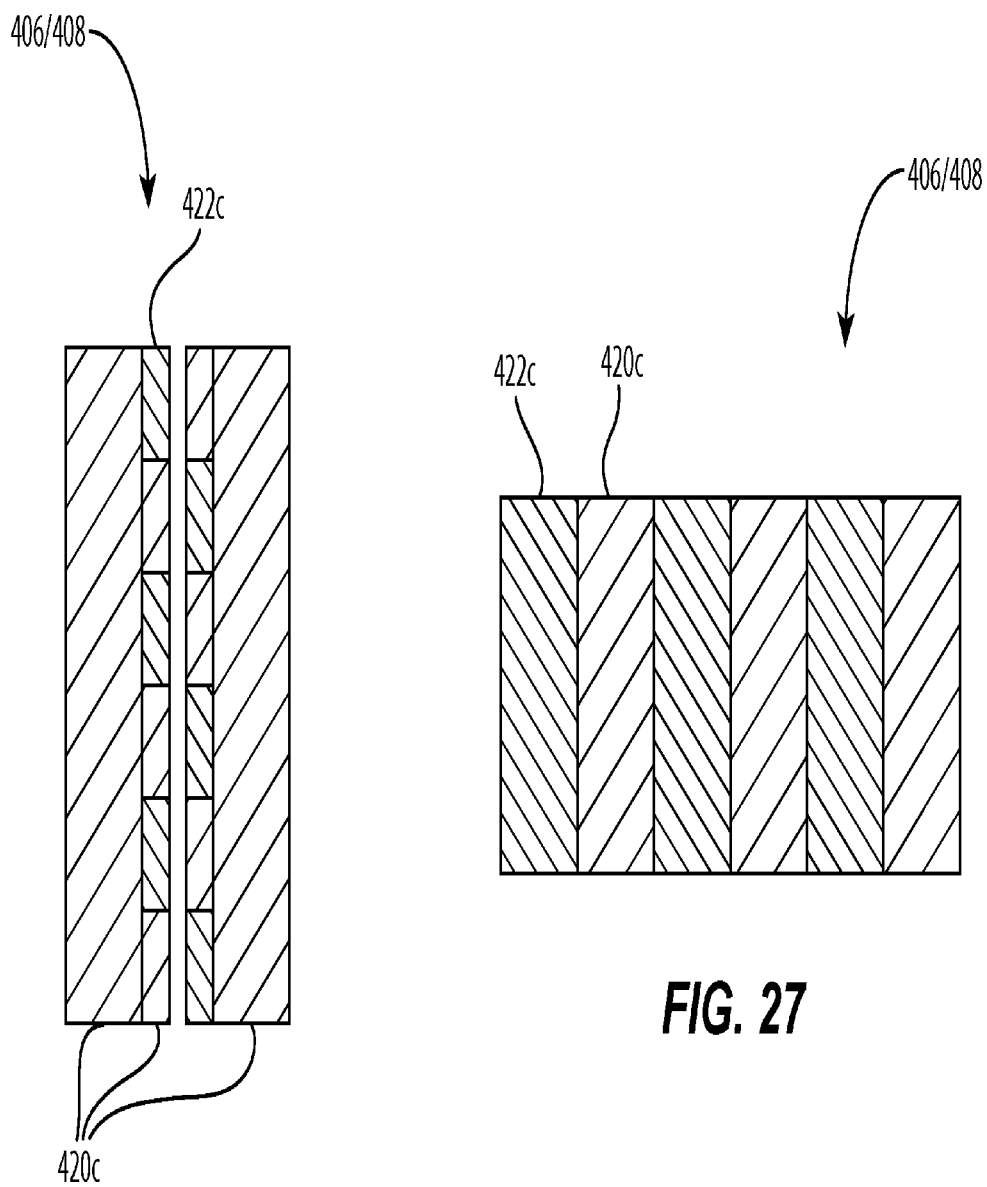
FIGS. 26 and 27 illustrate pad surfaces of a dynamic gripper of an active drive apparatus in accordance with an alternative preferred embodiment.

As shown in FIGS. 26-27, a pad surface of the dynamic gripper alternates between harder and softer (e.g., higher and lower durometers) sections 420c, 422c. For example, the alternation of low and high durometers on the surface of and between pads 406/408 may prevent pads 406/408 from binding against each other, e.g., with lower durometer materials on contacting pad sections 422c. During insertion/retraction, pad sections 422c (e.g., softer durometer) will slightly deform around elongate member 424 thereby increasing grip. When rolling elongate member 424 on an active drive design described in U.S. Nonprovisional patent application Ser. No. 13/838,777, issued as U.S. Pat. No. 9,408,669 on Aug. 9, 2016, which is herein incorporated by reference, and described in paragraph 0040, the pads translate with respect to each other. Therefore, section 420c (e.g., harder durometer) will have to exert enough sheer force on elongate member 424 to break the friction forces between the pad sections 422c (e.g., softer durometer) and elongate member 424. However, after the friction forces are met or exceeded, elongate member 424 may roll with pad sections 422c in a deformed condition.

Figures 28, 29:
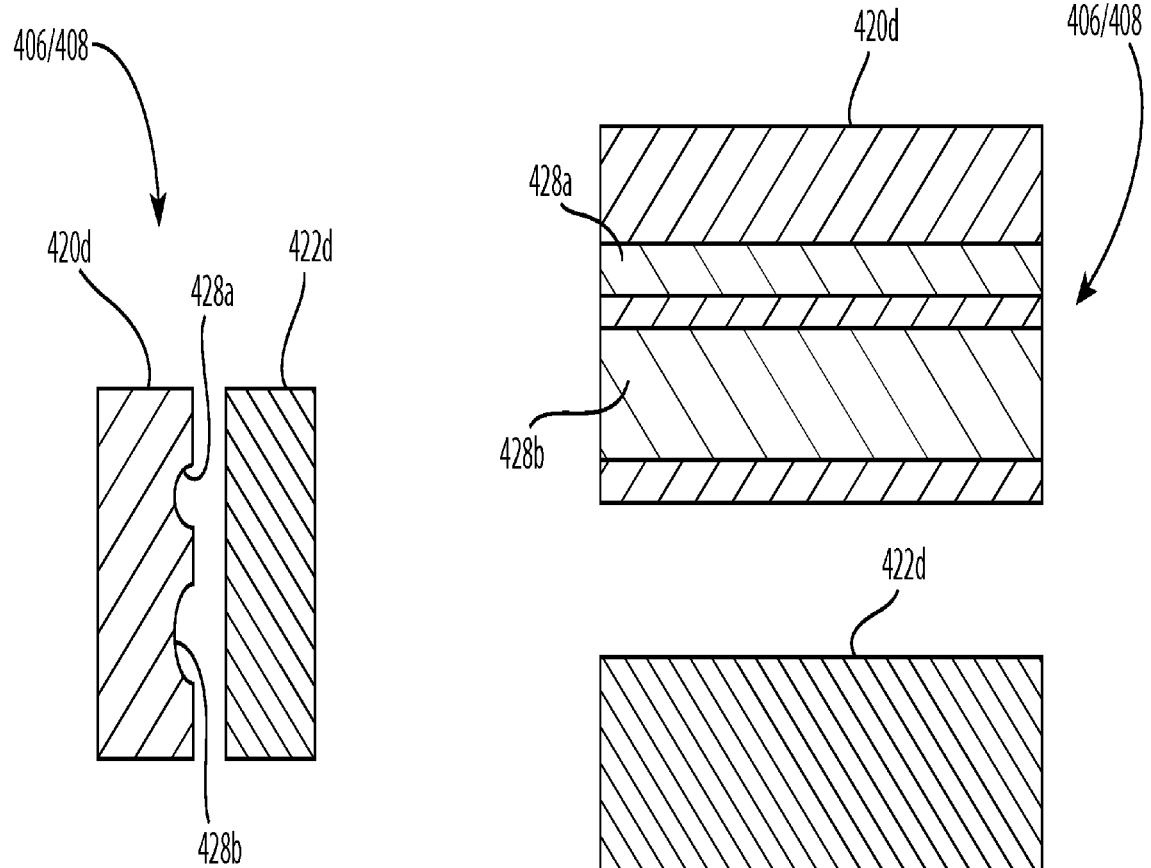
FIGS. 28 and 29 illustrate pad surfaces of a dynamic gripper of an active drive apparatus in accordance with an alternative preferred embodiment.

Referring to FIGS. 28-29, pad section 420d (e.g., harder durometer) may have one, two (shown), or more insets 428, which may be on opposite sides of a central portion of pad section 420d. Inset 428a may have a smaller radius (e.g., 0.01 inches for 0.014 and 0.018 inch diameter guide wires) and inset 428b may have a larger radius (e.g., 0.018 inches for 0.035 inch diameter guide wires). Insets 428a, 428b may be near a central portion of pad section 420d, for example, so elongate members 424 may pass through eyelets 426 of pads 410/412 without repositioning pad sections 420d, 422d to the first and second configurations, discussed above with respect to FIGS. 22-23. Pad section 422d (e.g., softer durometer) may provide grip for insertion and retraction of elongate member 424.

Alternative embodiments may have any number of other or additional features. For example, pads 406/408 may be made of a single durometer material including surface features (e.g., patterns, treads, or grooves) to optimize grip for elongate members 424 of all sizes. Further, pads 406/408 may include micro fibers or any other material with a high coefficient of friction, an ability to wick liquids, or an elasticity or lack of deformation under pressure. Moreover, pads 406/408 may include concave or convex surfaces, for example, to concentrate the forces to a desired line of contact between elongate member 424 and pads 406/408.

In some embodiments, an active drive system may include a guide wire or catheter drying or cleaning mechanism. Many guidewires have a wettable low friction hydrophilic coating. This coating absorbs moisture from the environment and produces a hydrogel which gives a low friction surface to the guidewire to help the physician advance the guidewire through the anatomy with low force. The guidewire drying mechanism absorbs the moisture from the hydrogel thereby removing the lubricous surface and increasing the friction. The guide wire drying mechanism thereby helps to reduce or eliminate guide wire slippage due to blood, plasma, saline, water, thrombus, and/or other materials and fluids. The drying or cleaning mechanism also removes debris and other unwanted materials, to ensure a better grip for the drive mechanism during roll, retraction, and/or insertion of the guide wire into the patient. The drying mechanism may include a debris-cleaning member and a holder for holding the debris-cleaning member against the guide wire and optionally clamping the debris-cleaning member against the guide wire.

In one embodiment, the debris-cleaning member includes one or more absorbent pads, such as gauze, foam, cotton, or the like, that act to absorb fluids and debris from the guide wire. The absorbent pads are typically positioned distal of (i.e. closer to the patient) the dynamic grippers or drive mechanism, so that the guide wire is cleaned and/or dried prior to reaching the drive/gripper components. For example, the absorbent pads may be connected to a separate component positioned between the drive component and the exit of the guide wire/catheter from the patient. In another example, the absorbent pads are integrated with the drive component, but positioned distal of the dynamic grippers.

In another embodiment, the debris-cleaning member may include a wiper or wicking element that wicks fluid and debris from the guide wire. The wiper can be used with or without the absorbent pads. For example, the wiper may be positioned in front of the absorbent pad to reduce the fluids reaching the absorbent pad and extend the useful life of the pad. As another example, the wiper may be positioned prior to the guide wire entering a drive component and may optionally include a vacuum or suction mechanism positioned adjacent to the guide wire (e.g., above or below the guide wire) that pulls the debris falling off the guide wire due to the wipers.

In yet another embodiment, the debris cleaning mechanism may include a suction or drying element. For example, a suctioning or vacuum component may be positioned at a location so as to reach the guide wire before it enters the drive mechanism. The suctioning or vacuuming component acts to pull debris (via a vacuum force) off of the wire. As another example, a heating element can be used to evaporate or dry the fluid so that the frictional coefficient of the gripping wire is increased.

By using the debris cleaning or drying mechanisms described herein, guide wires and catheters used for catheter procedures and other therapies may be less prone to slippage, reducing risks and injuries that can result from slippage, especially with hydrophillically coated devices that become very slippery when wet, which can increase the slip risk as the guide wire may not be held securely by either the static grippers or dynamic grippers when wet. Additionally, the debris cleaning mechanisms disclosed herein are automated or otherwise do not require user intervention or manipulation to operate. On the contrary, in conventional products, the physician may manually dry or clean the guide wire during retraction, which not only can complicate the procedure and/or workflow, but also increases the procedure time. Further, because of the drawbacks to manual cleaning by a physician or other worker, cleaning is typically only done after slippage has already occurred, which means that the guide wire has already lost position during a catheter exchange, therapy delivery, or the like, i.e., a potential injury or error may have already occurred before cleaning is completed. As the drying mechanism does not require a doctor or other user's attention or activation, the drying mechanism can be used during all stages of a procedure, helping to prevent slippage before it occurs, reducing the risks associated with slippage, and helping to reduce procedure time and complexity.

Figure 30:
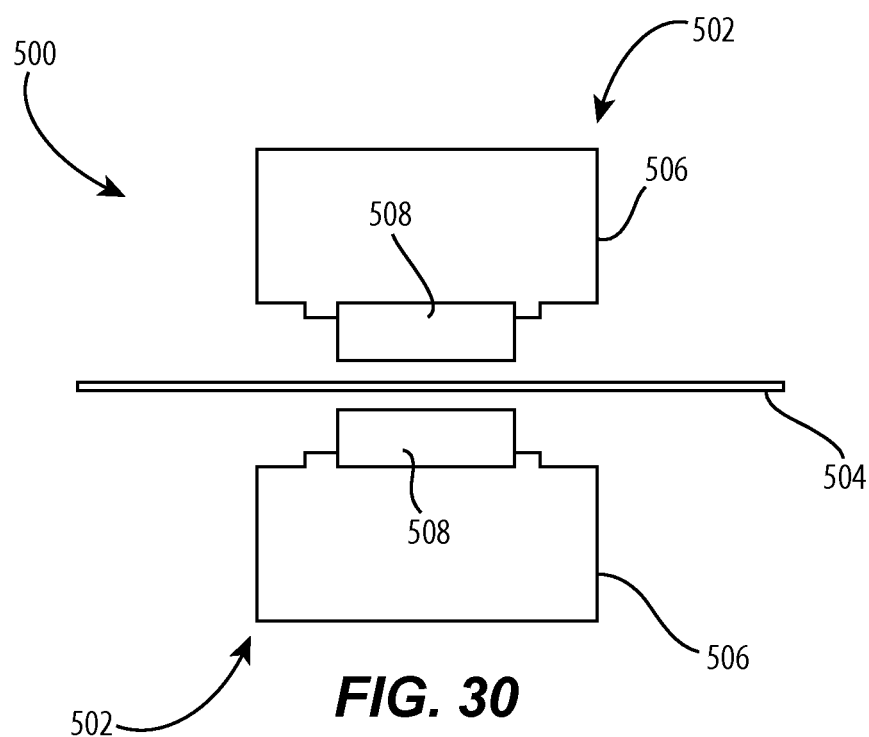
FIGS. 30 and 31 illustrate top plan views of a debris cleaning/drying mechanism in accordance with a preferred embodiment.
Figure 31:
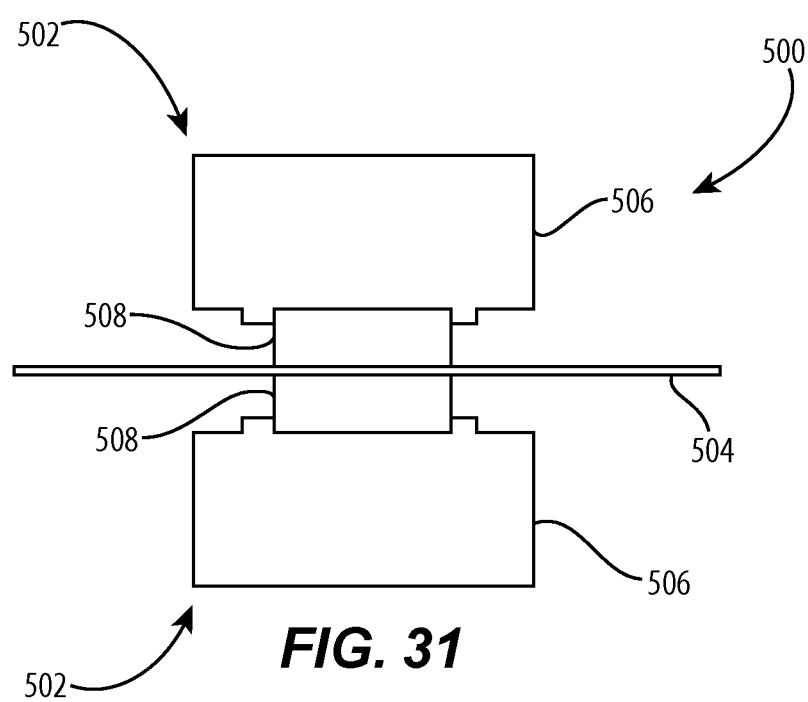

Turning back now to the figures, various examples of the debris cleaning or drying mechanism will now be discussed in more detail. FIG. 30 is a top plan view of the debris cleaning/drying mechanism 500 in the open positon. FIG. 31 is a top plan view of the debris cleaning mechanism 500 in the closed or clamped position. With reference to FIGS. 30 and 31, the debris cleaning mechanism 500 in this example includes two opposing cleaning clamps 502 positioned on opposite sides of a guide wire 504. The cleaning/drying clamps 502 may be positioned adjacent to a drive mechanism, such as the active drive mechanisms shown in FIGS. 2A-21, other active drive mechanisms, and/or passive drive mechanisms. Depending on whether cleaning is desired during retraction or insertion, the cleaning clamps 502 may be positioned on either the distal or proximal side of the drive mechanism relative to the insertion point within the patient. That said, in many embodiments, the cleaning/drying clamps 502 will be positioned between the insertion point within the patient and the drive mechanism to clean/dry the guide wire 504 after it exits the patient during retraction and prior to entering the drive mechanism.

With continued reference to FIGS. 30 and 31, the two cleaning/drying clamps 502 may be substantially the same as one another and each may include a pad holder 506 and one or more absorbent pads 508. The pad holder 506 holds the absorbent pads 508 and may optionally be configured to selectively clamp and unclamp the absorbent pads 508 against the guide wire 504. For example, the pad holders 506 may be connected to an active drive mechanism or may otherwise include a motorized power source that can move the pad holder 506 from a first or open position to a second or closed position. The pad holders 506 may also include brackets or other securing elements for securing the absorbent pads 508. Depending on the configuration of the brackets or securing elements, the absorbent pads 508 may be permanently attached to brackets or may be selectively removable from the pad holders 506.

The absorbent pads 508 are substantially any type of material that can absorb fluids and preferably is any type of absorbent material that does not shed fibers. For example, the absorbent pads 508 may be formed of gauze, microfiber, cotton, polyester, foam, synthetic fabric, porous rubber, or the like. The shape and configuration of the absorbent pads 508 may be varied as desired, which may depend on the type of procedure being performed, the diameter of the guide wire or catheter, the type of guide wire or catheter, the type of valve on the catheter, the type of drive system, or the like.

In some embodiments, the absorbent pads 508 include a barrier or drying surface. The barrier is a separate material from the absorbent pads, such as a coating, film, or the like, that acts to filter the fluids and debris absorbed into the absorbent pads 508 and/or help prevent the absorbent pads 508 from sticking to the guide wire 504, while still allowing fluids to pass therethrough to be absorbed by the pad. For example, the drying surface may be a porous-polymer coating, mesh, or the like.

Operation of the debris cleaning/drying mechanism 500 of FIGS. 30 and 31 will now be discussed in more detail. With reference to FIG. 30, the debris cleaning mechanism 500 is in the open position and the cleaning clamps 502 are spaced apart from the guide wire 504. In this position, the guide wire 504 can easily pass between the cleaning clamps 502 as the absorbent pads 508 do not touch or are in light to no contact with the guide wire 504. This allows the guide wire 504 to be more easily repositioned by the drive mechanism as the cleaning clamps 502 do not exert any friction on the guide wire 504 in this configuration. With reference to FIG. 31, after the guide wire 504 has been repositioned to a desired location, the cleaning clamps 502 may be moved to the closed position, so that the absorbent pads 508 are in full contact with the guide wire 504. In this position, fluids from the guide wire 504 are absorbed into the absorbent pad 508 and where the barrier is included, travel through pores into the barrier and into the pad 508. As fluids and other debris are absorbed into the pads 508, they are removed from the guide wire 504, increasing the coefficient of friction of the guide wire 504 by cleaning/drying the guide wire 504 to help prevent slippage when the guide wire 504 is received into the drive mechanism.

In the embodiment shown in FIGS. 30 and 31, the selective positioning of the cleaning clamps 502 relative to the guide wire 504 is used to reduce the potential of the absorbent pads 508 from interfering with movement of the guide wire 504 by the drive mechanism. However, depending on the type of material used for the absorbent pads 508 and/or barrier, the cleaning clamps 502 may be arranged to be engaged with the guide wire 504 during repositioning of the guide wire 504, i.e., in a permanently clamped position. For example, the barrier may have a sufficiently low coefficient friction such that the guide wire 504 can move along the barrier surface unobstructed when moved by the drive mechanism even when the absorbent pads 508 are clamped together. In this orientation, the cleaning clamps 502 may only be opened during the initial threading or insertion of the guide wire 504.

Figure 32:
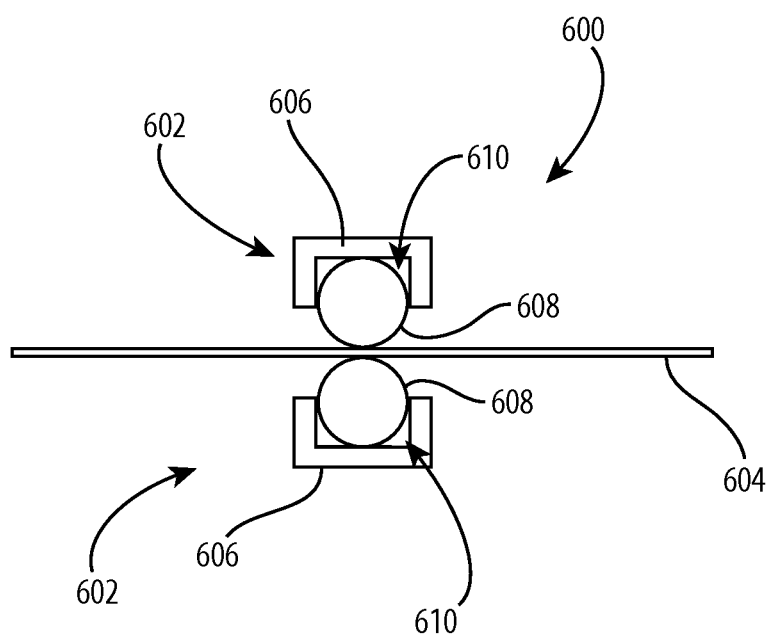
FIG. 32 illustrates a top plan view of a debris cleaning/drying mechanism in accordance with an alternative preferred embodiment.

In some instances the absorbent pads 508 may be removable and replaceable from the cleaning clamps 502. FIG. 32 illustrates another example of the debris cleaning mechanism. With reference to FIG. 32, in this embodiment, the pad holders may form brackets defining a pad cavity 610 or recess and the absorbent pads 608 may be positioned in the pad cavity 610 and constrained from movement by the edges of the pad holders 606. In this example, the top and/or bottom ends of the pad holders 606 may be open to allow the absorbent pads 608 to be slid into and out of the pad cavity 610. The absorbent pads AA may be modified to match the shape of the pad holders or alternatively the pad holders may be modified to match the shape of the absorbent materials. As one example, a gauze roll may be used as the absorbent pad and the cylindrical roll may be inserted into the pad holder 606 and easily removed when saturated without substantially disrupting the guide wire 604 or the drive assembly. In the example shown in FIG. 32, the absorbent pads may be static and may be positioned sufficiently close to the guide wire 604 so that the guide wire 604 engages with at least one and preferably both absorbent pads 608 as it is moved by the drive assembly. Alternatively, the cleaning clamps 602 may be configured as in FIGS. 30 and 31 so that the pad holders 606 are selectively moved closer together and farther apart to clamp and unclamp around the guide wire/catheter.

Figure 33:
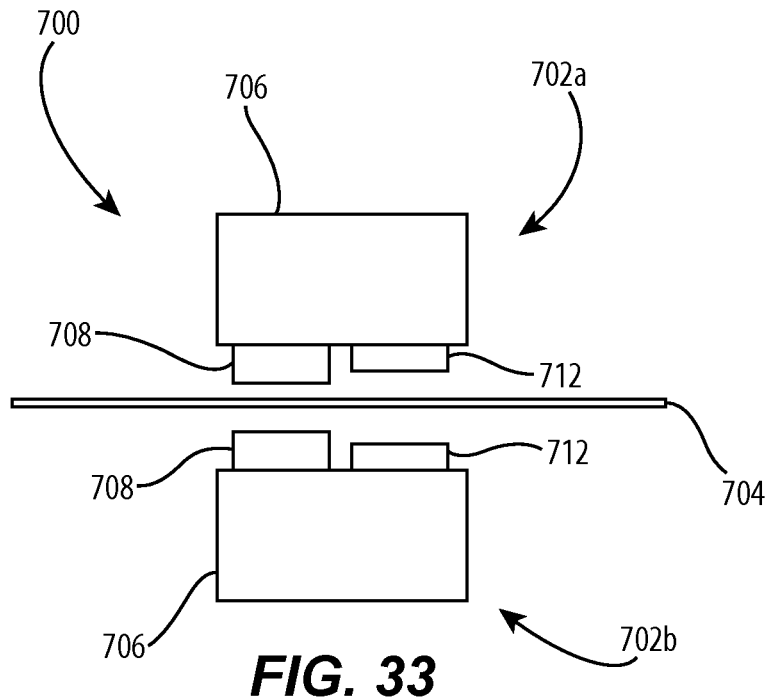
FIGS. 33 and 34 illustrate top plan views of a debris cleaning/drying mechanism in accordance with an alternative preferred embodiment.
Figure 34:
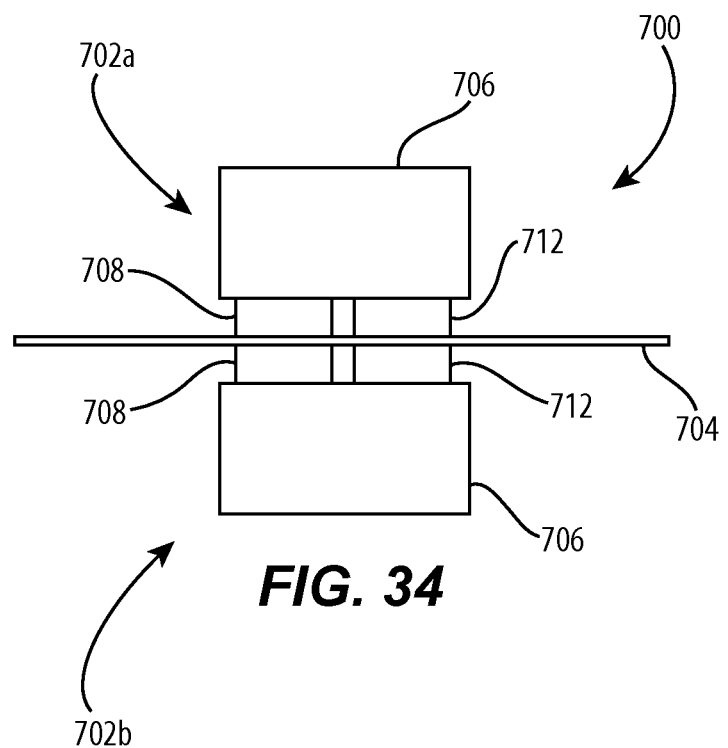

In the embodiments shown in FIGS. 30-32, the debris cleaning mechanism is separate from the driving and/or clamping mechanisms of the catheter insertion assembly or system. However, in other embodiments the debris cleaning mechanism is incorporated into the static gripper mechanism. FIG. 33 is a top plan view of a debris cleaning mechanism integrated into a static gripper mechanism in the open position. FIG. 34 is a top plan view of the debris cleaning mechanism of FIG. 33 in the closed or clamped position. With reference to FIGS. 33 and 34, the drying mechanism 700 may be substantially the same as the drying mechanisms 500,600, but in this example, the cleaning/drying clamps 702 may include the absorbent pads 708 and the gripper pads 712. The gripper pads 712 and the absorbent pads 708 may both be positioned on a front face of the cleaning clamps 702 and oriented to face the corresponding pads on the opposite cleaning clamp. That is, the absorbent pad 708 for the first cleaning clamp 702a is positioned across from the absorbent pad 708 of the second cleaning clamp 702b and likewise the gripper pad 712 for the first cleaning clamp 702a is positioned across from the gripper pad 712 for the second cleaning clamp 702b. In one embodiment, the absorbent pads 708 are positioned distal of the gripper pads 712, so that the guide wire 704 is cleaned as it exits the patient's body or catheter and before it reaches gripper pads 712. In some embodiments the absorbent pads 708 are spaced apart from the gripper pads 712 to define a gap between the two pads. However, in other embodiments, the absorbent pads 708 and the gripper pads 712 on each cleaning/drying clamp 702 are positioned adjacent to and touching one another.

With continued reference to FIGS. 33 and 34, the gripper pads 712 in this embodiment may be substantially the same as the other gripper pads disclosed herein. Additionally, the cleaning clamps may be driven by similar active drive mechanisms as disclosed herein, with the exception being that the cleaning clamps may also include brackets for holding the absorbent pads. Depending on the materials used for the absorbent pads 708 and the gripper pads 712 the thickness of each of the pads 708, 712 may be the same or may be varied. For example, in one embodiment, the absorbent pads 708 may be more easily deformed than the gripper pads 712 and in this example, the absorbent pads 708 may have a first thickness T1 and the gripper pads 712 may have a second thickness T2 where T2 is greater than T1. If the absorbent pads are on the same clamp as the dynamic gripper pad, T2 is used such that when the clamps are in the open position, the absorbent pads remain in contact with the wire such that they serve to clean/dry the wire in the return stroke while the dynamic gripper is open. Continuing with this example, as the absorbent pads 708 deform more readily and in the clamped position (see FIG. 34), the absorbent pads 708 deform to the same thickness as the dynamic gripper pads 712. However, in other embodiments, if the absorbent pads are on the same clamp as the static gripper pad, the static gripper pads 712 and the absorbent pads 708 may have the same thicknesses or the static gripper pads 712 may have a greater thickness as compared to the absorbent pads 708.

Operation of the drying mechanism 700 of FIGS. 33 and 34, will now be discussed in more detail. Generally, the operation of the drying mechanism 700 may be substantially the same as the drying mechanism 500 of FIGS. 30 and 31, however, as the cleaning clamps 702 are moved, the guide wire 704 is repositioned by the dynamic gripper pads 712. In particular, in the open position of the cleaning clamps as shown in FIG. 33, the static gripper pads (not shown in FIG. 33) secure the guide wire 704 to hold it in a desired position and the dynamic gripper pads 712 may be repositioned relative to the wire. For example, the entire cleaning clamp 702 may be repositioned relative to the guide wire 704 to move the guide wire 704 to a different location relative to the gripping surface of the gripper pads 712 and absorbent pads 708. Alternatively the pads 712 themselves may be moved relative to the pad holders 706 to reposition the guide wire 704.

With reference to FIG. 34, after the gripper pads 712 have been repositioned as desired, the debris cleaning mechanism 700 transitions to the clamped position. In the clamped position, the absorbent pads 708 and the gripper pads 712 are moved to clamp against the guide wire 704. As the absorbent pads 708 clamp against the guide wire, they act to absorb fluids from the guide wire 704, cleaning and drying the guide wire 704.

In the debris cleaning mechanism 700 of FIGS. 33 and 34, the absorbent pads 708 and/or the gripper pads 712 may be removable and replaceable. For example, the two sets of pads may be removed and replaced in a set. As another example, the pads may be individually replaceable. In this example, waste may be reduced since the absorbent pads may need to be replaced more frequently than the gripper pads and can be removed and replaced when needed, without requiring the gripper pads to be replaced as well.

Although in the embodiment shown in FIGS. 33 and 34 the absorbent pads 708 and the gripper pads 712 are shown as two separate components, in other embodiments, the absorbent pads 708 and the static gripping pads 712 may be integrated into a single component. For example, a first portion of an integrated absorbing and static gripping pad may have an absorbent material and a second portion of the pad may include a gripping material for gripping the guide wire. In another example, a single material may be sufficiently absorbent and with a sufficiently high coefficient of friction to grip the guide wire, while also removing fluids from the wire. Similarly, although the embodiment of FIGS. 33 and 34 have been discussed with respect to a single absorbent pad and a single gripping pad on each cleaning clamp 702, in other embodiments, the drying mechanism may include two or more of each pad on each clamp.

Figure 35:
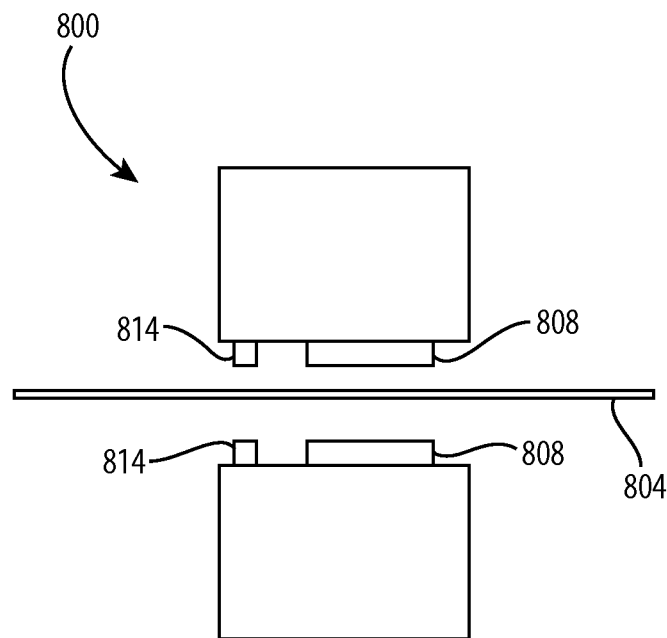
FIGS. 35 and 36 illustrate top plan views of a debris cleaning/drying mechanism in accordance with an alternative preferred embodiment.
Figure 36:
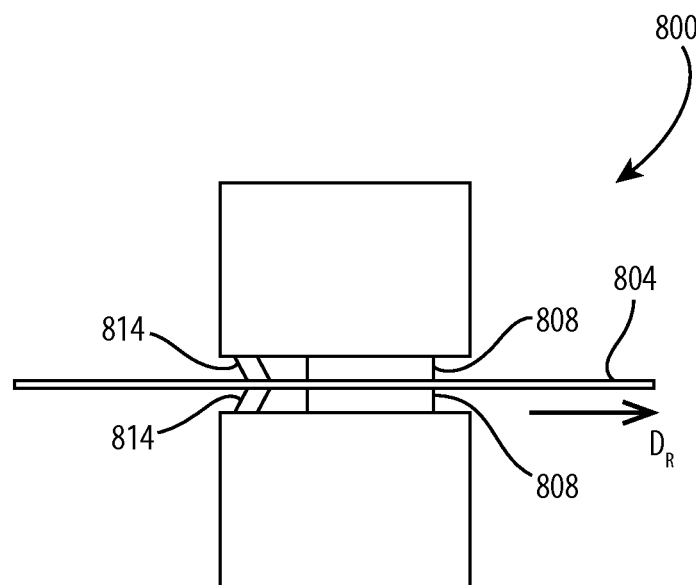

In addition to or alternatively to the absorbent pads, the drying mechanism may also include a wick or wiper. FIGS. 35 and 36 illustrate top plan views of a drying mechanism including both a wiper and an absorbent pad. With reference to FIGS. 35 and 36, the drying mechanism 800 of this embodiment may be substantially similar to the drying mechanism of FIGS. 30 and 31, but may also include a wiper 814. The wiper 814 may be positioned distal of the absorbent pad 808 so that as the guide wire 804 is retracted, the wiper 814 reaches the guide wire before the absorbent pad 808. In other words, in the retraction direction $D_R$, the wiper is positioned in front of the absorbent pad 808.

The wiper 814 may be substantially any type of flexible material, such as rubber, silicone, or the like. The wiper 814 wicks fluid and debris off of the guide wire 804. The wiper 814 can be used on its own, or as shown in FIGS. 35 and 36, may be used in combination with the absorbent pads. In examples where the wiper is used with the absorbent pads, wiper 814 helps to prolong the life of the absorbent pads as more of the fluids and debris are wiped off of the guide wire 804 before the guide wire 804 reaches the absorbent pad 808. This allows the absorbent pad 808 to absorb fewer fluids and debris, while also increasing the overall dryness of the guide wire 804 as two separate drying mechanisms are used. In other words, the wiper 814 may act as a squeegee to remove debris from the outer surface of the guide wire 804 which works in tandem with the absorbent pads to fully dry the guide wire.

With reference to FIG. 35, the wiper 814 may be sufficiently flexible so that in the clamped or closed position of the drying mechanism the wiper may deform as it presses against the guide wire 804. This characteristic allows the cleaning clamps to be clamp sufficiently close to the guide wire 804 and each other that the guide wire 804 engages with the wiper 814 to ensure that the guide wire 804 can move relative to the wiper when needed, but is also sufficiently engaged to allow fluids to be removed from its outer surface.

Figure 37:
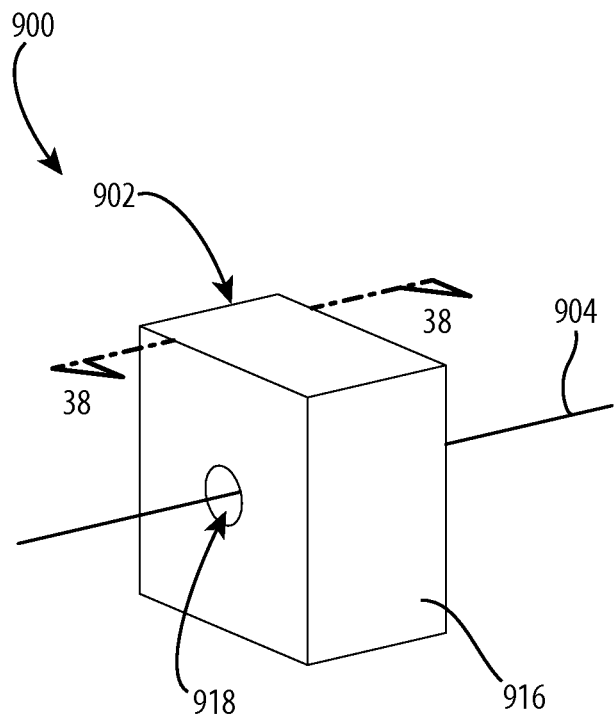
FIGS. 37 and 38 illustrate perspective and cross sectional views, respectively, of a debris cleaning/drying mechanism in accordance with an alternative preferred embodiment.
Figure 38:
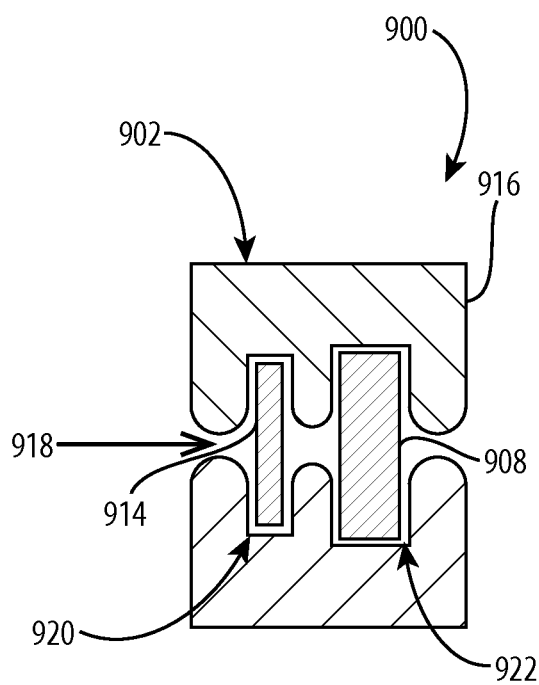

As briefly mentioned above, in some embodiments, the debris cleaning mechanism includes replaceable absorbent pads and/or wipers. FIG. 37 illustrates a perspective view of a debris cleaning mechanism with a replaceable cleaning clamp. FIG. 38 is a cross-section view of the debris cleaning mechanism of FIG. 37 taken along line 38-38 in FIG. 37. With reference to FIGS. 37 and 38, in this example, the debris cleaning mechanism 900 may include an enclosed cleaning clamp 902 housing one or more absorbent pads 908 and/or wipers 914. In particular, the cleaning clamp 902 includes a housing 916 having a wiper aperture 918 defined therethrough and having a lead-in inlet and an outlet on the front and back sides of the housing 916, respectively. The wire aperture extends through a central region of the housing and extends through both a wiper cavity 920 and a pad cavity 922 in the housing.

With reference to FIG. 38, the wiper cavity 920 and the pad cavity 922 are configured to support a wiper 914 and an absorbent pad 908, respectively. The wiper 914 and the absorbent pad 908 may be substantially the same as the absorbent pads and wipers shown in FIGS. 33 and 34, but are received within the housing 916. The absorbent pads 908 and wipers 914 may also include a wire aperture defined therethrough or may include two or more components compressed towards each other by the housing to define a small gap for the guide wire to extend through. In these configurations, the guide wire 904 is threaded through the lead-in inlet, into the wire aperture 918 of the housing, through a wire aperture of the wiper 914 and the absorbent pad 908 and then out the outlet to exit the housing 916. In other words, in this configuration, the guide wire 904 is axially loaded into the housing 916.

During operation, the housing 916 is positioned between the patient and the drive mechanism and the guide wire 904 is threaded into the housing 916 as described above. As the guide wire is moved or retracted by the drive mechanism, the wiper 914 acts to wick fluids and debris from the guide wire 904 and whatever fluids or debris remain on the wiper 914 are absorbed by the absorbent pad such that as the guide wire 904 exits the housing 916 the wire may be substantially dry or otherwise clean. During prolonged use, the absorbent pad 908 may become saturated and have to be replaced. In these instances, the guide wire 904 is removed from the housing 916 and the housing is replaced with a new, non-statured housing. The guide wire 904 is then threaded into the new housing 916 as described above and the drying/cleaning process can begin again as the drive mechanism is activated.

Figure 39:
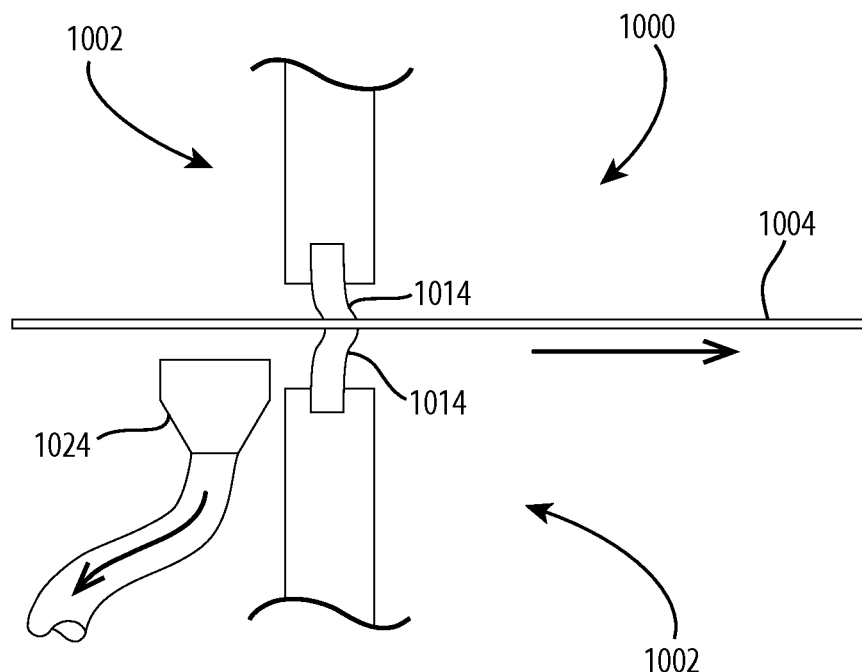
FIG. 39 illustrates a top plan view of a debris cleaning/drying mechanism in accordance with an alternative preferred embodiment.

In some embodiments, the debris cleaning mechanism may also include an air based drying or cleaning mechanism. For example, the debris cleaning mechanism may include a heating element, air blower or dryer, and/or a vacuum or suction device. FIG. 39 illustrates a side view of an example a debris cleaning mechanism including a suction device. With reference to FIG. 39, in this example, the cleaning clamps 1002 of the debris cleaning mechanism 1000 may include the wipers 1014 and optionally may include the absorbent pads (not shown in this embodiment). Additionally, with reference to FIG. 39, the debris cleaning mechanism includes a suction device 1024 positioned at the inlet end of the cleaning clamps 1002. The suction device 1024 activates a vacuum or other suctioning mechanism to pull fluids and debris off the guide wire 1004 prior to the guide wire 1004 reaching the wipers 1014. In these embodiments, the suction device 1024 helps to remove most of the fluid and debris prior to reaching the cleaning clamps 1002. This not only helps to ensure that more of the fluids and debris are removed from the guide wire 1004 so it is dry and less prone to slippage, but also helps to extend the life of the cleaning clamps 1002. For example, when the absorbent pads 1008 are used, the suction device 1024 reduces the amount of fluids that are absorbed by each of the pads 1008 by removing the fluids prior to reaching the pads so that the pads may be used for longer periods of time.

As briefly noted above, in addition to activating a suction mechanism to remove the fluid, the suctioning device may be replaced by a blow-drying device that blows air onto the guide wire 1004 to help remove the fluid and debris and/or evaporate the fluid and debris. Similarly, a heating element may be positioned at the entry to the cleaning clamps to evaporate the fluids and help to clean the wire. Also, the suctioning device, blowing device, and/or heating element may be used with or without the cleaning clamps including the absorbent pads and/or wipers. In other words, the drying mechanism 1000 may include just the suction mechanism, drying mechanism, and/or heating mechanism.

Figure 40:
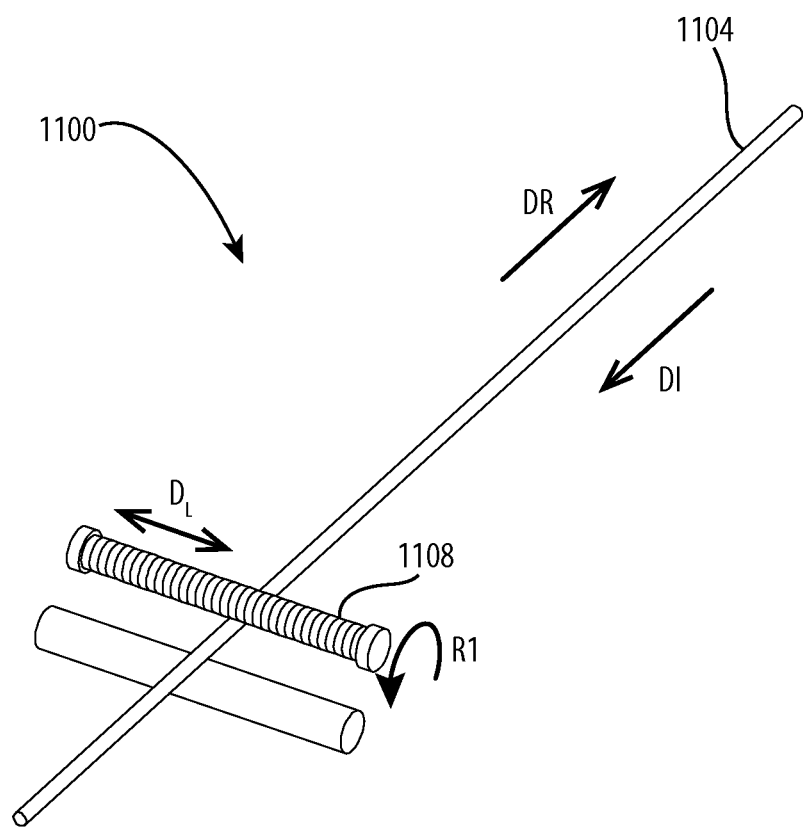
FIG. 40 illustrates a top plan view of a debris cleaning/drying mechanism in accordance with an alternative preferred embodiment.

In many of the embodiments of the debris cleaning mechanism described in FIGS. 30-39, the guide wire is typically moved relative to the absorbent pad. However, in some embodiments, the absorbent pads may also be moved relative to the guide wire to change the areas of the absorbent pad in contact with the guide wire, increasing absorption and helping to extend the life of the pad. FIG. 40 is a perspective view of an example of the debris cleaning mechanism including a movable absorbent pad. With reference to FIG. 40, in this example, the debris cleaning mechanism 1100 may include an absorbent pad that moves in a longitudinal direction $D_L$ and optionally in a rotational direction $R_1$ relative to the guide wire 1104. That is, the absorbent pad 1108 may be rotated and moved horizontally relative to the guide wire 1104 so that various areas on the outer surface of the absorbent pad 1108 are brought into contact with the guide wire 1104, so that the entire absorbent pad is exposed and able to absorb fluids, rather than only one section.

In one embodiment, the absorbent pad may be received into a bracket similar to the pad holder 606 of FIG. 32, which may move laterally across the guide wire 1104 and the pad 1108 may be a cylindrical shape and rotate due to the movement of the guide wire 1104 by the drive mechanism. In other embodiments, the absorbent pad 1108 may be connected to an axel or other support device that extends through a center of the pad 1108 or is otherwise configured to rotate the pad 1108 and also move the pad in the longitudinal direction $D_L$. As the absorbent pad becomes saturated or otherwise needs to be replaced, another pad can be inserted into the pad holders, or may be inserted coaxially to the first saturated pad.

It should be noted that any of the features of the drying mechanisms described in FIGS. 30-40 may be used with any of the other features of the other embodiments. For example, the wipers may be combined with the drying mechanism of FIG. 40. As another example, the absorbent pads may be used with the suction mechanism of FIG. 39, instead or in addition to the wipers. As such, the description of any particular implementation is meant as illustrative only and many other embodiments and implementations are envisioned.

Controlling Active Drive Systems
Synchronizing and Aligning Active Drive Motors

To optimize the continuous effective insertion of an elongate member with the mechanisms described above, the angular position of the insertion and grip motors' output shafts generally must be synchronized so the mechanism is inserting when the dynamic gripper is closed and the static grippers are open. Subsequently, it is necessary to have the dynamic gripper open when the insertion motor is moving backwards before the dynamic gripper re-clutches on the elongate member to move the elongate member forward again via the insertion motor. Without proper synchronization between the insertion and grip motors, however, insertion becomes less effective. For instance, if the dynamic gripper is closed when moving backwards or for even part of the backward stroke, then the elongate member would retract rather than insert. Hence, the efficiency of the mechanism is reduced with regards to the effective insertion rate.

Accordingly, precisely determining the location of a motor in the mechanisms range of motion is crucial for alignment of multiple motors and ultimately synchronization of the motors. It is important to determine the electrical current profile of the mechanism to ascertain distinctive characteristics, for example peaks and troughs, of the current profile. The distinctive characteristics may occur, for example, due to the presence of varying torque due to cams as the motor in the mechanism moves through their range of motion. The motors may be coupled to electrical current sensors, wherein the sensors may be in communication with a monitor including a processing system, for analyzing an electrical current profile of each motor.

The electrical current profile, and consequently the peaks and/or troughs representing distinctive characteristics, may be generated by driving each motor a full repetition through the motor's range of motion. Additionally or alternatively, each motor may be driven multiple repetitions to compensate for phase shifts of the current signal to yield multiple current profiles, for example to account for latency with the monitoring system. These electrical current profiles may then be averaged to compensate for any phase shifts and produce demonstrative current characteristics.

Figure 41:
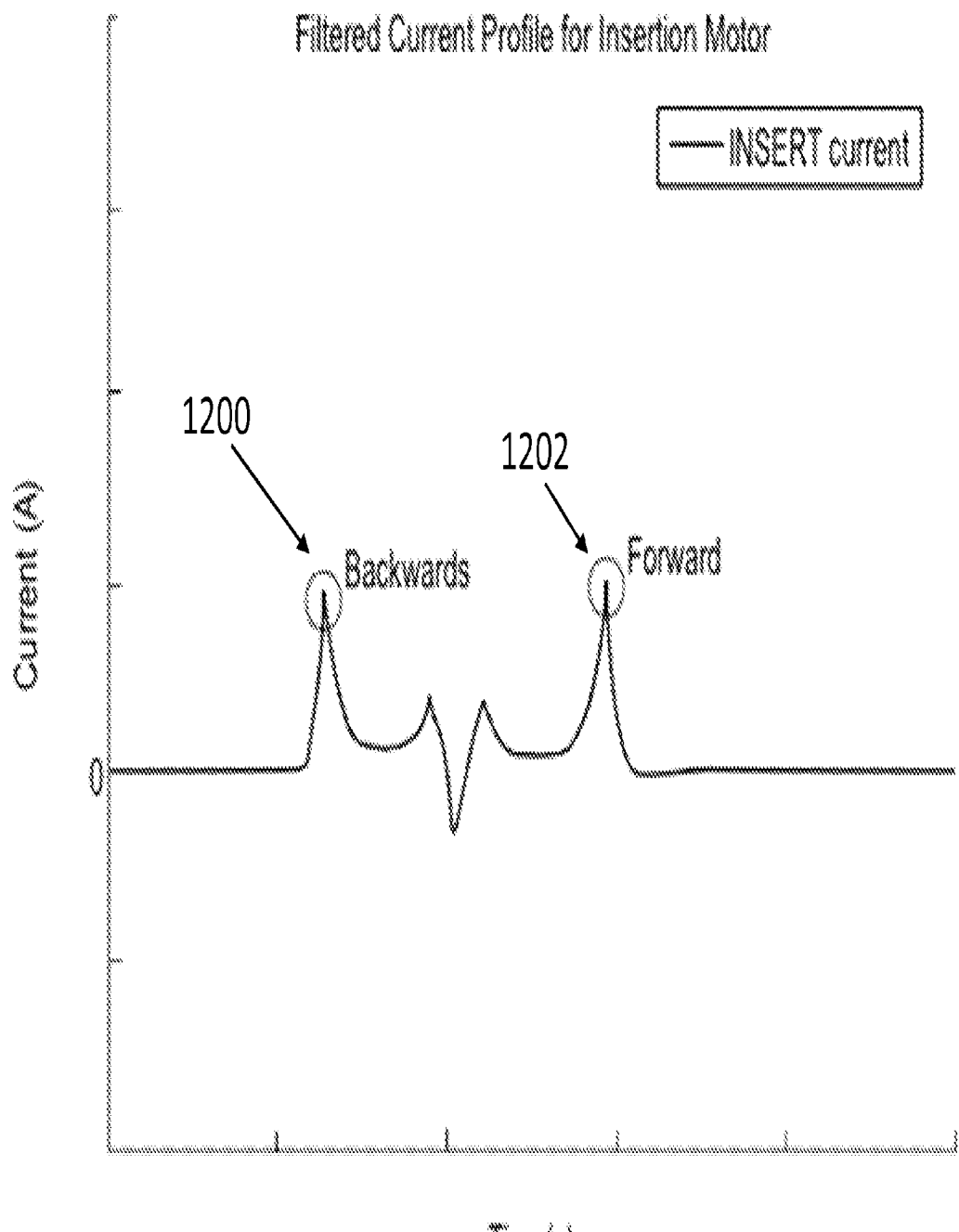
FIGS. 41 and 42 illustrate distinctive characteristics of the current profile of an insert motor and a grip motor, respectively, in accordance with a preferred embodiment.
Figure 42:
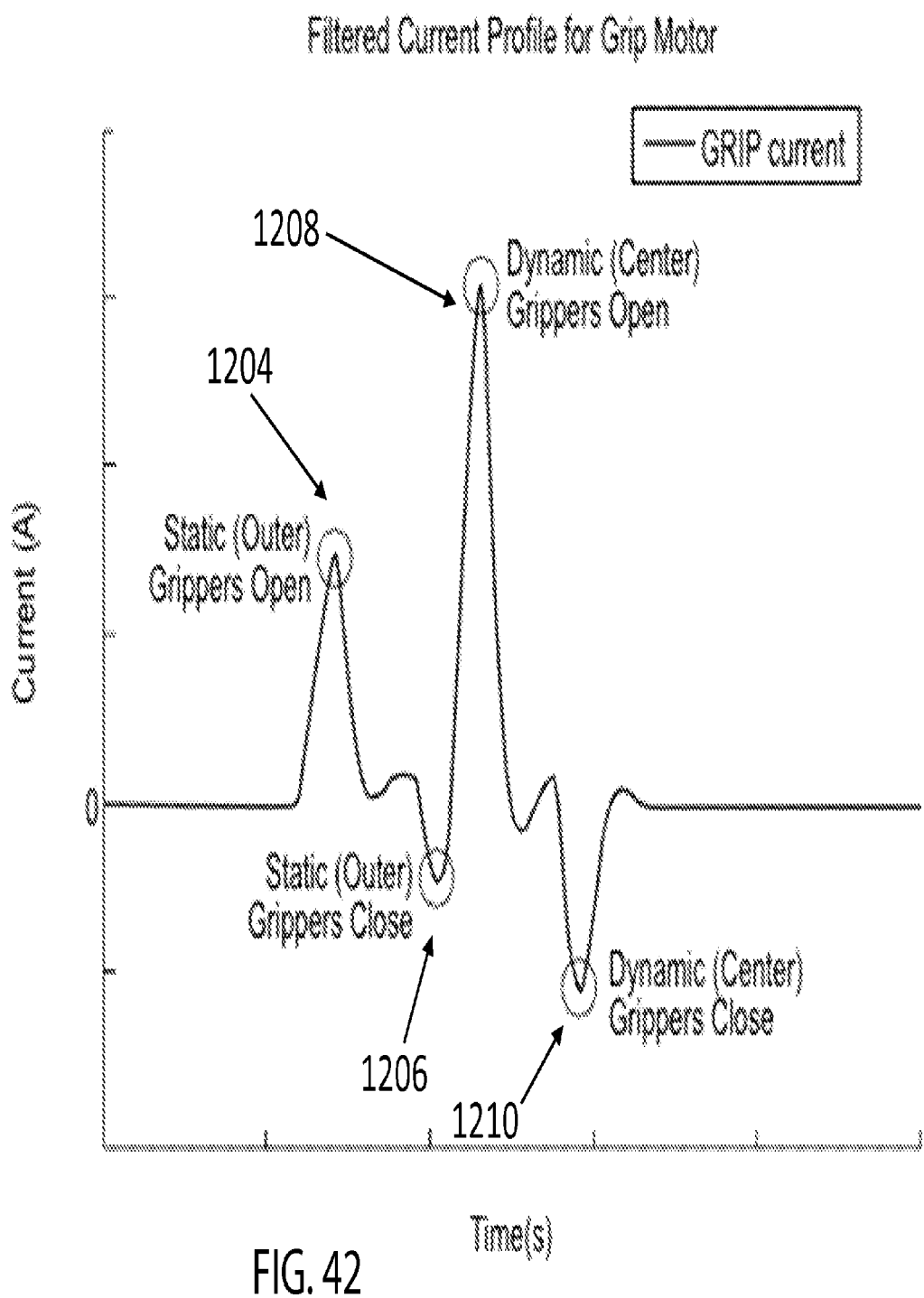

The distinctive characteristics of the current profile may correspond to particular actions or functions of the motor. For example, FIGS. 41 and 42 illustrate exemplary distinctive characteristics for the current profile of the insert and grip motors, respectively. In the example according to FIG. 41, the peaks in the current profile may represent the "forward" and "backward" strokes of the dynamic gripper (e.g., via the insert motor). For instance, the first peak 1200 in current may indicate the start of the backwards motion and the second peak 1202 may indicate the start of forward motion. In an alternative implementation, the first peak 1200 may represent clockwise rotation around an axis, whereas the second peak 1202 may indicate counterclockwise rotation. The action of the motor is inconsequential as the disclosure is not limited to any particular type of mechanism. For example, while some embodiments may be generally directed to rotational mechanisms or motors, other types such as translational mechanisms may also be employed.

For example, FIG. 42 illustrates distinctive characteristics indicated by both peaks and troughs. For instance, the first or intermediate peak 1204 in current may indicate that the static (or outer) grippers are opening while the first or intermediate trough 1206 may indicate the static grippers are closing. On the other hand, the current of the gripper motor may be at its maximum, for example at its highest peak 1208, when the gripper is opening and at its minimum or lowest trough 1210 when the dynamic gripper is closing.

The filtered electrical current profile may be used to locate or pinpoint where exactly in the range of motion each motor is in at a given time. The distinct characteristics of each motor's electrical current profile, for example the relevant peaks and/or troughs, may indicate the motor's position in response to a given motor's range of motion. Such current peaks and/or troughs or other characteristics may correspond to loading or unloading of an electrical drive system and associated electrical current(s). For instance, with reference to FIG. 41, the second peak may represent the commencement of motor insertion. If the exemplary mechanism includes a range of motion for the insert motor of 7 mm forwards and backwards, the electrical current profile according to FIG. 41 signifies that the insert motor begins moving backwards or retracts 7 mm at the first peak and commences moving forwards or inserts 7 mm at the second peak. Likewise, after analyzing the electrical current profile for the gripper motor according to FIG. 42, the start of the static and dynamic grippers clutching and un-clutching of the elongate member can be precisely determined. Accordingly, the distinctive characteristics correlating to motor actions of the insert and grip motors may be used to align the motors angular positions for the most effective insertion rate.

The distinctive characteristics of the insert motor may be coordinated with complementary distinctive characteristics of the gripper motor to optimize the efficiency of the mechanism (e.g., optimize maximum insertion rate). For example, for maximum effective insertion rate of the above mechanism, it is necessary to align the closing of the dynamic gripper with the forward motion of the insert motor. With reference to the electrical current profiles of the respective motors, the position of the insert motor when the current is at its maximum (e.g., the second peak 1202 according to FIG. 41) is aligned with the position of the gripper motor when the current is at the minimum (e.g., the lowest trough 1210 in FIG. 42). Coordinating the peaks and troughs of the electrical current profiles with corresponding positions of the motors ensures that the elongate member is ultimately driven by the mechanism monotonically.

To align the motors, the positional relationship of the motors as the motors progress through their range of motion in the mechanism needs to be calibrated. The positional relationship may depend on the mechanism used. For instance, the positional relationship for an active drive system may use a 1:1 relationship between the insert and grip motors. For proper alignment, an offset may be incorporated into the positional relationship determination, and added to the position of one of the motors. The offset may take into account the positional relationship between the motors for a given mechanism (e.g., 1:1 ratio, 2:1 ratio, 3:2 ratio, etc.). Thus, for example, if insert motor X had a peak current indicating insertion motion at 1 rad, and gripper motor Y had a minimum current indicating closing of dynamic gripper at 1.3 rad, then the calculated offset would be 0.3 radians. Accordingly, an equation used to calculate the position of motor Y in relationship to motor X is:

$$pos_y = pos_x + \text{offset}$$

The points at which the positional relationship between the two motors is measured may be any position in which a characteristic of the current profile for motor Y is aligned with a complementary characteristic in the current profile for motor X. For instance, the first peak of FIG. 42 indicating backwards movement of the insert motor may be aligned with the maximum current (e.g., the second peak) of FIG. 41 indicating the dynamic gripper is open.

Once the positional relationship is determined, the motors may be mechanically timed as they progress through a full cycle and repeat through their range of motion in the mechanism. That is, the mechanism is mechanically timed such that at the same motor speed the insertion movements of insert motor X and grip movements of gripper motor Y complement one another. Accordingly, for every repetition/revolution of the insert and grip motor of the active drive mechanism shown in FIGS. 2A-21, the complementary actions of each motor are coordinated as follows:

| Revolution | Insert Motor X | Grip Motor Y |
| --- | --- | --- |
| 0-¼ | Insert 7 mm | Dynamic Gripper Closed |
| ¼-½ | Wait | Dynamic and Static Gripper Switch State |
| ½-¾ | Retract 7 mm | Dynamic Gripper Open |
| ¾-1 | Wait | Dynamic and Static Gripper Switch State |

Figure 43A:
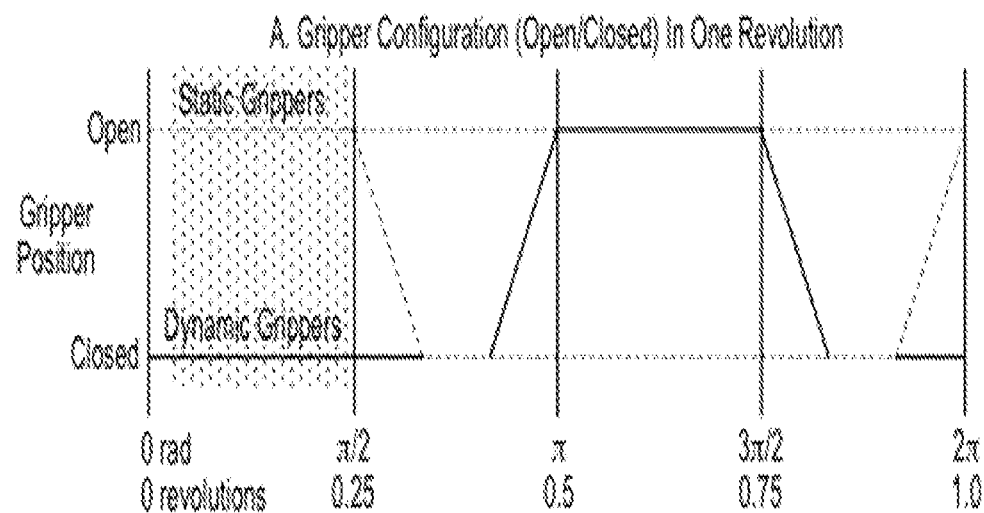
FIGS. 43A and 43B illustrate the respective positions of an insert motor and a gripper motor during one revolution or one full cycle/repetition in accordance with a preferred embodiment.
Figure 43B:
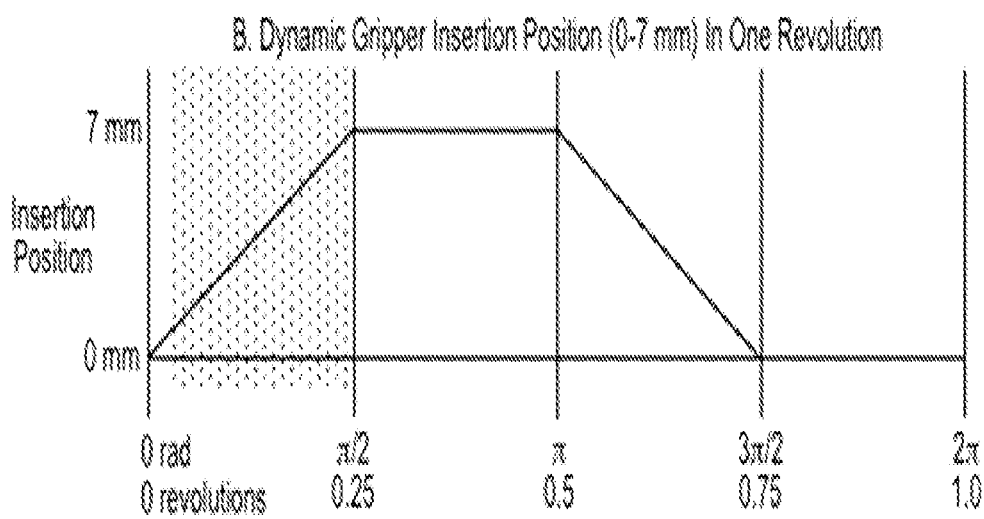

After alignment, motor X and motor Y may be driven at the same velocities, ensuring that motors will maintain their positional relationship. In the example above, insert motor X may be driven at the same velocity as grip motor Y such that motor Y will always be 0.3 rad ahead of motor X, thereby ensuring synchronization between the motors. This can be seen in FIGS. 43A and 43B, which provides a graphical representation of the above table. FIGS. 43A and 43B illustrate the insert and gripper motor positions during one revolution or one full cycle/repetition through the mechanism after alignment via the positional relationship equation above. That is, FIGS. 43A and 43B show the insert motor synchronized with the gripper motor after alignment using each motors filtered electrical current profile.

FIG. 43A illustrates the positions of the gripper motor while FIG. 43B illustrates the movement of the insert motor as they progress through their range of motion per revolution after the motors have been mechanically timed (e.g., after synchronization). For the first quarter revolution, the dynamic grippers are closed while the static grippers are open when the insert motor is moving forward or inserting. For the second quarter revolution, the dynamic and static grippers switch positions (e.g., dynamic grippers open and static grippers close) while the insert motor stays idle (e.g., neither inserts nor retracts). The third quarter revolution of the motors includes the static grippers closed and the dynamic grippers open as the insert motor moves backwards or retracts. For the final quarter revolution, the dynamic and static grippers switch states (e.g., dynamic gripper closes and static gripper opens) and the insert motor waits and is idle. Thus, upon one full revolution, the insert and grip motors are back in the original position ready to re-clutch and insert the elongate member.

Figure 44:
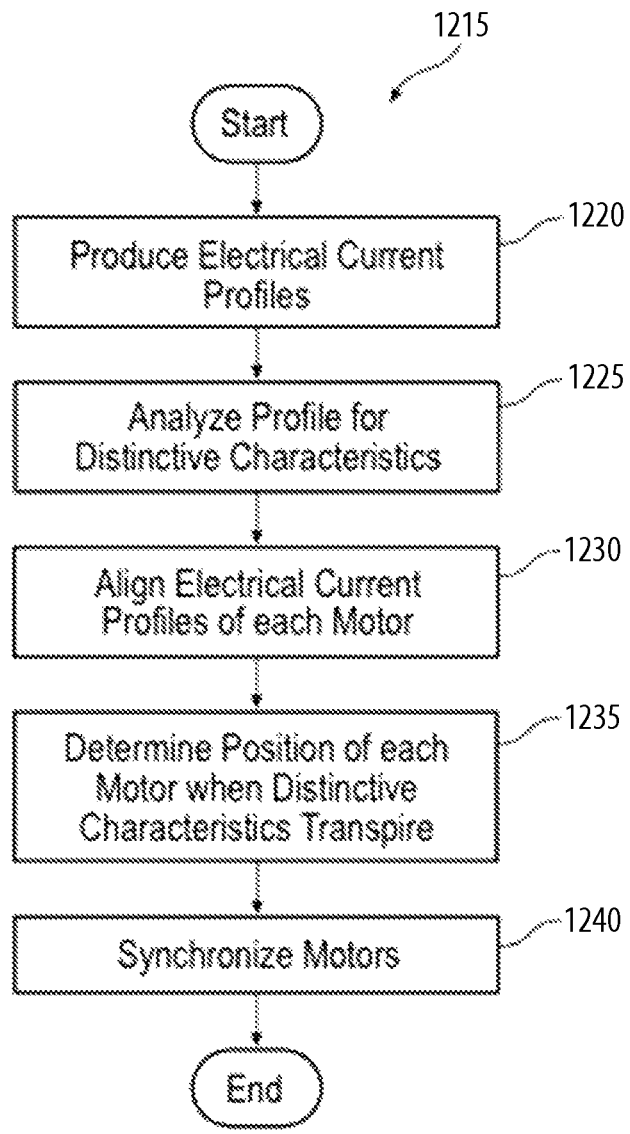
FIG. 44 illustrates a process for aligning and synchronizing objects, such as motors, based on electrical current profiles and in accordance with a preferred embodiment.

FIG. 44 illustrates an exemplary process 1215 for aligning and synchronizing objects, such as motors, based on electrical current profiles. The process 1215 may begin at block 1220, where the electrical current profile for each motor in the mechanism is produced. The electrical current profiles may be generated by driving each motor one full revolution or repetition as its current is filtered and tracked, for example via electrical current sensors. Additionally, the motors may be driven multiple repetitions to generate a plurality of symmetric electrical current profiles, and taking the average current profile to compensate for any phase shifts of the current signal. Once the electrical current profile is produced, the process may proceed to block 1225.

At block 1225, the electrical current profile for each motor is analyzed for relevant peaks and/or troughs (e.g., analyzed for distinct characteristics). For example, the electrical current profile may be communicated to a monitor for study and analysis. The filtered electrical current may then be analyzed to determine the distinct characteristics of the profile. For instance, with reference to FIG. 42, the gripper motor may produce two peaks and two troughs per repetition. These distinct characteristics may then be associated with motor actions. For example, by monitoring the gripper motor as it progresses through its range of motion, it may be determined that the current is at its maximum when the dynamic grippers open, the current has a smaller distinctive peak when the static gripper is open, and the current is at its minimum when the dynamic gripper closes. The same analysis and association may take place with all the motors in the mechanism, for example associating the insert motion when the insert motor has a maximum electrical current. The process may then proceed to block 1230.

At block 1230, the electrical current profiles of each motor in the mechanism are aligned with one another. The alignment of each motor may depend on the mechanism design. In the above example, to optimize the effective insertion rate of the peristaltic active drive mechanism, the closing of the dynamic gripper of the gripper motor needs to be aligned with the forward (or backward if retracting the elongate member from the patient) stroke of the insert motor. In terms of the electrical current profiles of each motor, the insert motor when the current is at its maximum needs to be aligned with the gripper motor when its current is at its minimum (for maximum effective insertion or forward stroke). The process next proceeds to block 1235.

At block 1235, the position at which point in each motor's range of motion is determined for the distinctive characteristics of the electrical current profiles. These determined positions are then used to coordinate the gripper and insert motor such that the current profile characteristics of the insert motor are aligned with complementary current profile characteristics of the gripper motor. For instance, by monitoring the motors as they progress through the range of motion it may be determined that the insert motor has its peak current at 1 rad while the gripper motors has its minimum current at 1.3 rad. Accordingly, the offset may be calculated to determine the positional relationship of the motors for proper alignment. That is, the equation used to calculate the position of motor Y in relationship to motor X is:

$$pos_y = pos_x + offset$$

Thus, if insert motor is X and gripper motor is Y, the offset would be 0.3 radians (1.3=1+offset). After alignment, motor X and motor Y are driven at the same velocities, and motor Y will always be 0.3 rad ahead of motor X. This is true for the mechanism described above, as the mechanism used a 1:1 relationship between the insert and grip motors. However, the equation holds true regardless of the mechanism positional relationship (e.g., 2:1, 3:1, 3:2, etc.). Upon determining the positional relationship, the process may proceed to block 1240.

At block 1240, the motors may be synchronized to one another such that correlative motor actions complement one another. That is, the mechanism may be mechanically timed such that at the same motor speed, the insertion and grip movements are synchronized with each other. Referring to the above example, this means that the dynamic gripper is closed when the insert motor is moving forward (or backwards depending if insertion or retraction is the goal), and the static grippers are closed with the dynamic grippers open when the insert motor is moving backwards to reset. The final synchronized mechanism is illustrated in FIGS. 43A and 43B. The information obtained in analyzing, aligning, and synchronizing the motors via the electrical current profiles may be stored into a database for future replication. Accordingly, once the motors are aligned and synchronized for the first time, the insert and grip actions of the mechanism will be synchronized so that the effective insertion/retraction will always be monotonic thereafter.

Variable Stroke Length of Active Drive Motors

Figure 45:
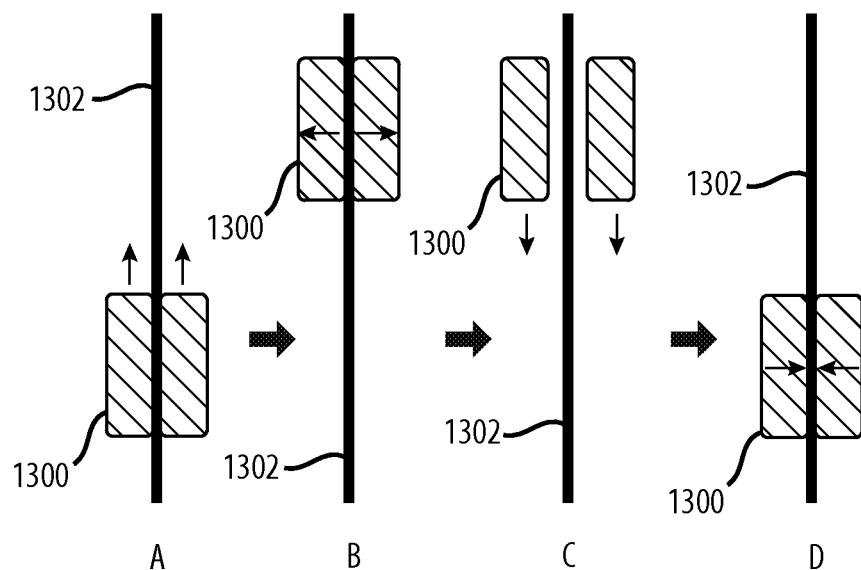
FIGS. 45 and 46 illustrate longer and shorter stroke lengths during periods of lower and higher insertion forces, respectively, in accordance with a preferred embodiment.
Figure 46:
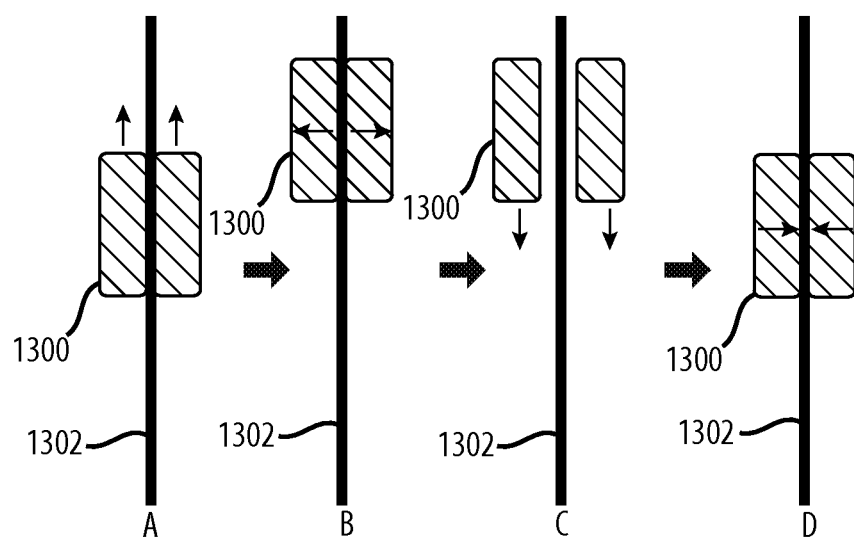

In some embodiments, an active drive system may include dynamic grippers that are configured to vary their stroke length during insertion of an elongate member. As shown in FIGS. 45-46, dynamic gripper 1300 may be configured to vary its stroke length during insertion of an elongate member 1302. Varying the insertion stroke length on dynamic gripper 1300 may optimize speed while simultaneously reducing or preventing buckling. At higher insertion forces, short strokes may prevent buckling of elongate member 1302, and at low insertion forces, longer stroke lengths may lead to faster insertion speeds. Retraction may be performed with a longer stroke for increased speed. Using dynamic grippers 1300 with variable stroke lengths may reduce or eliminate extra anti-buckling devices and may increase insertion speeds and usability.

Variable insertion stroke length may be achieved with any mechanism that uses a peristaltic motion, for example the active drive systems described in FIGS. 11-21. The peristaltic motion may include advancing elongate member 1302 from a retracted position to an extended position with dynamic grippers 1300 (shown as step A), releasing elongate member 1302 with outward transverse movement of dynamic grippers 1300 (shown as step B), retracting dynamic grippers 1300 from the extended position to the retracted position (shown as step C), and re-gripping elongate member 1302 by inward transverse movement of dynamic grippers 1300 (shown as step D).

FIG. 45 illustrates a longer insertion stroke length during periods of lower insertion forces. In this mode, dynamic grippers 1300 may return to a fully retracted position before re-gripping and advancing elongate member 1302. By utilizing this mode, the dynamic grippers 1300 may operate at a lower frequency and insert elongate member 1302 at higher speeds. Also, elongate member 1302 may achieve a higher advancement rate, because the inward spring forces on dynamic grippers 1300 are overcome less frequently and less time may be spent accelerating and decelerating dynamic grippers 1300. When returning to the fully retracted position, it may be desirable to retract dynamic grippers 1300 as fast as possible with a longer stroke length to accomplish higher speeds for better usability.

Alternatively, FIG. 46 illustrates a shorter insertion stroke length during periods of higher insertion forces. For example, dynamic grippers 1300 may return to an intermediary retracted position before re-gripping and advancing elongate member 1302. By utilizing this mode, buckling of the elongate member may be reduced or avoided with a lower advancement rate. Reducing the insertion stroke length to the intermediary retracted position may reduce anti-buckling equipment, cost, setup time, and potential damage to elongate member 1302.

Stroke length may vary based on insertion forces and therefore it may be useful to detect insertion forces or predict buckling in order to optimize the stroke length. Force sensors may measure insertion forces, for example, to help anticipate and detect buckling. Test data on a variety of elongate members with varying characteristics may determine the force thresholds used to determine the buckling forces. Characteristics may include the diameter, stiffness, or material of elongate member 1302.

The system may recognize, using force sensors, when the insertion forces on elongate member 1302 reach upper and lower force thresholds. The upper force threshold (i.e. for a buckling condition) and lower force threshold (i.e. for a baseline condition) may be derived from empirical data and specified given the particular type of elongate member 1302 and the current unsupported length or stroke length.

When the insertion forces on elongate member 1302 reach the specified higher force threshold, the system may detect or indicate to the operator and/or operator workstation that buckling may potentially occur and the stroke length may be automatically or manually shortened in real-time to reduce or avoid potential buckling of elongate member 1302. Alternatively, when insertion forces reach a lower force threshold, the stroke length may be lengthened in real-time to increase insertion speed. Force sensors may be utilized to change the stroke length of dynamic grippers 1300 to optimize speed and buckling reduction in elongate member 1302.

Figure 47:
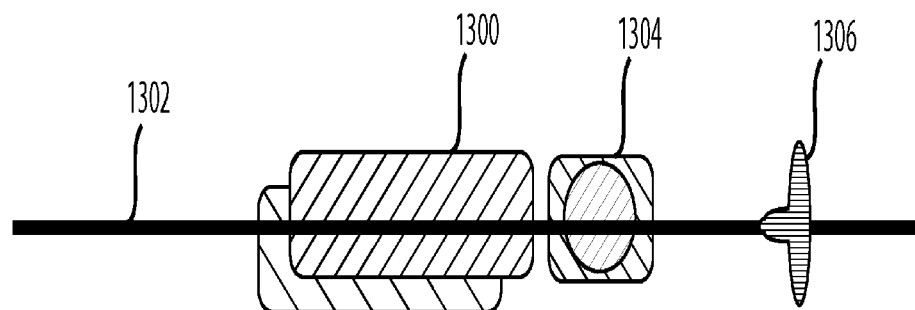
FIGS. 47 and 48 illustrate the use of optical sensors to confirm if an elongate member is in a baseline condition or in a buckling condition in accordance with a preferred embodiment.
Figure 48:
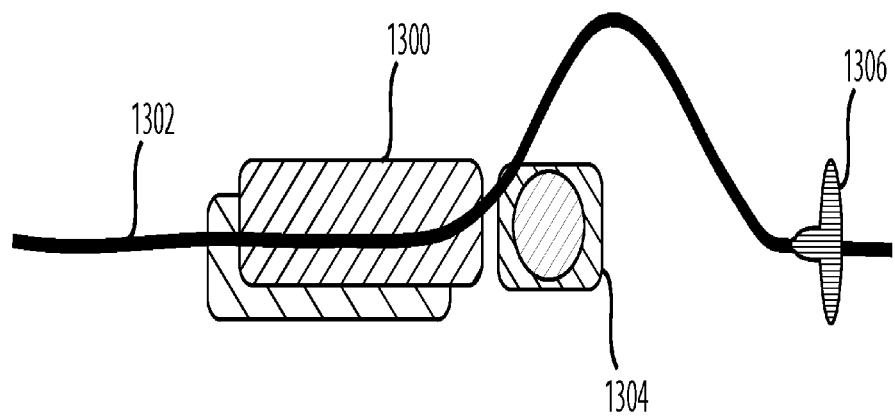

Optical sensor 1304 may be utilized to confirm if elongate member 1302 is in a baseline condition, as shown in FIG. 47, or a buckling condition, as shown in FIG. 48. An elongate member may be inserted through valve 1306, for example a hemostatic valve. Optical sensor 1304 may detect if elongate member 1302 is inside or outside its field of view. The system may detect or indicate to the operator and/or operator workstation that buckling has occurred. Multiple optical sensors 1304 may be oriented in a vertical row perpendicular to elongate member 1302 to determine the severity of buckling or in a horizontal row along elongate member 1302 to detect the location or length of buckling. By having optical sensors 1304 oriented in rows, the area of detection for buckling increases and the height or length of the buckling may be determined. The higher or longer the buckling, the more severely the buckling will impede insertion. Optical sensors 1304 may also be utilized to adjust the stroke length of dynamic grippers 1300.

In some embodiments, optical sensors 1304 may be used in conjunction with force sensors. Using force models to set the upper and lower force thresholds, real-time force data may be compared to the force models to determine when buckling may occur. By comparing real-time data with model data, the system may detect or predict a buckling condition to the operator and/or operator workstation. Upon prediction of a buckling condition, the stroke length of grippers 1300 may be automatically adjusted or manually adjusted by controls on the operator workstation to prevent buckling. Alternatively, upon a prediction of buckling, dynamic grippers 1300 may be re-clutched forward to shorten the stroke length thereby reducing the stroke length and the insertion speed of elongate member 1302. If the system cannot predict buckling in time and take precautionary measures as described above, and if buckling actually occurs, then the operator workstation may indicate a warning to the user that buckling has occurred, so the user may take corrective actions such as checking elongate member 1302 for damage or kinks. Any combination of force sensors, optical sensors 1304, and empirical models may be utilized to re-clutch dynamic grippers 1300, for example, to reduce the stroke length to help prevent buckling of and damage to elongate member 1302.

Dynamic grippers 1300 may also re-clutch elongate member 1302 when switching between retraction and insertion modes. A transition from retraction to insertion could constitute a forward re-clutch of dynamic grippers 1300 to revert to a longer stroke length during retraction. For this transition, the possibility of buckling should be determined as described above and the insertion stroke length should be adjusted appropriately.

Figure 49:
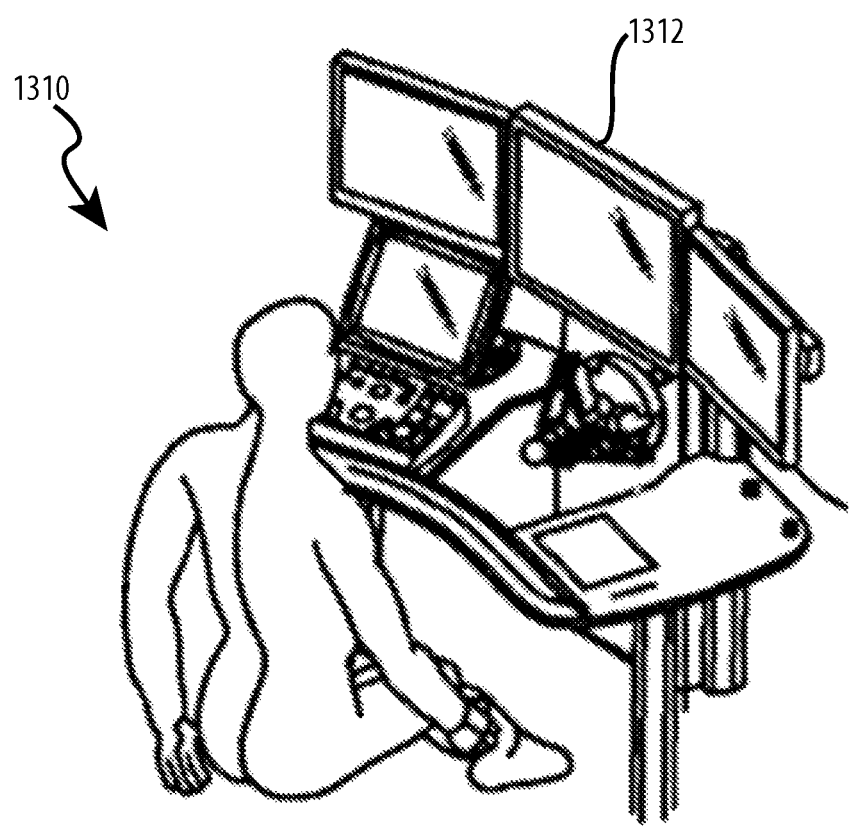
FIG. 49 illustrates the use of a real-time imaging device to detect and prevent buckling of an elongate member in accordance with a preferred embodiment.

Due to the variability in elongate members 1302, the characteristics of each type of elongate member 1302 may be helpful in determining the force thresholds for buckling detection and prevention. The configuration of the system may depend on the type of elongate member 1302. The type of elongate member 1302 may be specified by user input, automatically determined by a sensor, or a combination thereof. An optical sensor, for example, may determine the diameter of elongate member 1302 and the user may input material characteristics. Material characteristics may include material and coating types, for example presence of a hydrophilic coating. With the information on the type of elongate member 1302, the system may automatically or the user may manually specify the force thresholds for the particular type of elongate member 1302. With reference to FIG. 49, additional instruments may assist with the detection and prevention of buckling. The system 1310 may include a real-time imaging device 1312, for example fluoroscopy. With an imaging device 1312, the user can see when they are inserting in an area likely to require higher insertion forces, for example, due to tortuous anatomy or anatomical obstacles. The user may use visual feedback from the imaging device 1312 to determine insertion forces. The user may vary a haptic input to vary the stroke length of dynamic grippers 1300. The user would have to deduce the amount of relative force being applied to the elongate member based on visual feedback and adjust the stroke length accordingly.

The system 1310 may also include a haptic device that mimics user motion and provides tactile feedback to the user. The haptic device may mimic the motions of and forces applied by the user. The haptic device may directly translate the user's motion to vary the stroke length to an adjustment in stroke length by dynamic gripper 1300.

Managing Elongate Member Slip

During use of the active drive systems described above, it is important to accurately position the elongate member in the patient and to retain the elongate member at that position until a desired task is accomplished. However, elongate members are preferably designed and manufactured to facilitate insertion into the patient without undue resistance, and elongate members may slip, migrate, or otherwise move with respect to the patient so that the tip of the elongate member moves away from the desired position. Thus, there exists a need to predict and reduce slip of an elongate member.

Figure 50A:
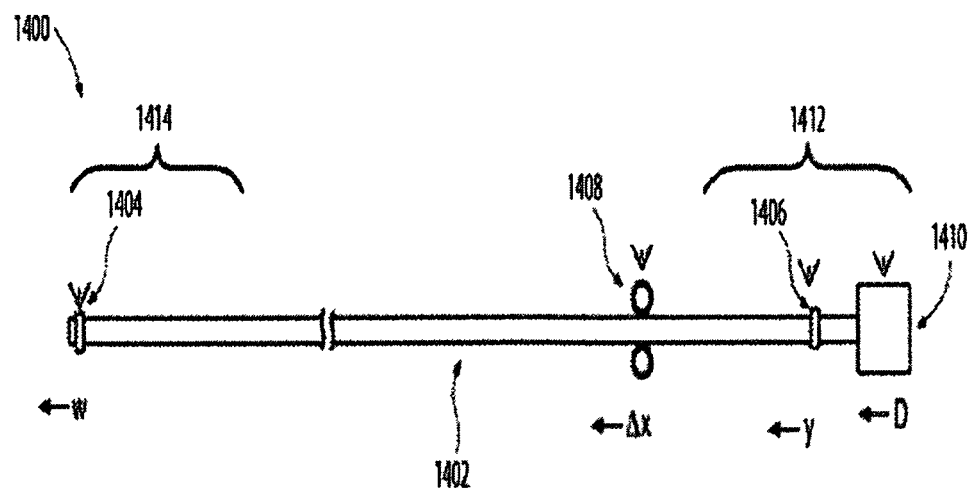
FIGS. 50A and 50B illustrate a slip detection system in accordance with a preferred embodiment.

FIG. 50A illustrates one embodiment of a catheter assembly 1400 comprising a slip detection system including one or more sensors for detecting slip of an elongate member. As shown in FIG. 50A, the catheter assembly 1400 may include an elongate member 1402, a first sensor 1404, and a second sensor 1406. As further described below, a drive mechanism 1408 and splayer 1410 may be provided for driving insertion/retraction of the elongate member 1402, and steering the elongate member 1402, respectively. The elongate member 1402 may be of any size, and may have a proximal portion 1412 and a distal portion 1414. The first sensor 1404 is located adjacent the distal portion 1414 of the elongate member 1402 and may be configured to measure a displacement $\Delta Y$ of the distal portion 1414 of the elongate member

1402. The second sensor 1406 is located adjacent the proximal portion 1412 of the elongate member 1402 and may be configured to measure a displacement ΔW of the proximal portion 1412 of the elongate member 1402.

The drive mechanism 1408 may be configured to translate the elongate member 1402 along a commanded insertion distance ΔX. Any drive mechanism may be employed to command translational and/or rotational motion of the elongate member 1402, including but not limited to grippers, rollers, or the like as described above.

In some embodiments, the first sensor and/or the second sensor may be optical sensors or roller sensors (i.e., contact sensors), for example. More specifically, optical sensors may be used to read a translational position of the elongate member 1402, for example the proximal portion 1412 (represented as Y in the Figures) and/or the distal portion 1414 (represented as W in the Figures). Optical sensors may advantageously allow placement of the sensors outside a sterile barrier enclosing the elongate member 1402. In some embodiments, a contact sensor may include a roller or wheel in contact with the elongate member 1402 or portions thereof, and may measure a displacement or translational motion of the elongate member 1402 by passively rolling in response to motion of the elongate member 1402. In contrast to optical sensors, a contact sensor may require placement within the sterile field that includes the elongate member 1402, since it generally remains in contact with the elongate member 1402 during operation.

In some embodiments, any number of additional sensors may be at any location along the elongate member 1402 and/or on the drive mechanism 1408 for measuring any additional conditions of the elongate member 1402 that may be desired. For example, the drive mechanism 1408 and/or splayer 1410 may measure an insertion force applied to the elongate member, an insertion speed of the elongate member 1402, or a grip force applied to the elongate member 1402 by the drive mechanism 1408. Alternatively or additionally, separate sensors (not shown) may be provided for detecting insertion force applied to the elongate member 1402 or any portion thereof.

Figure 51:
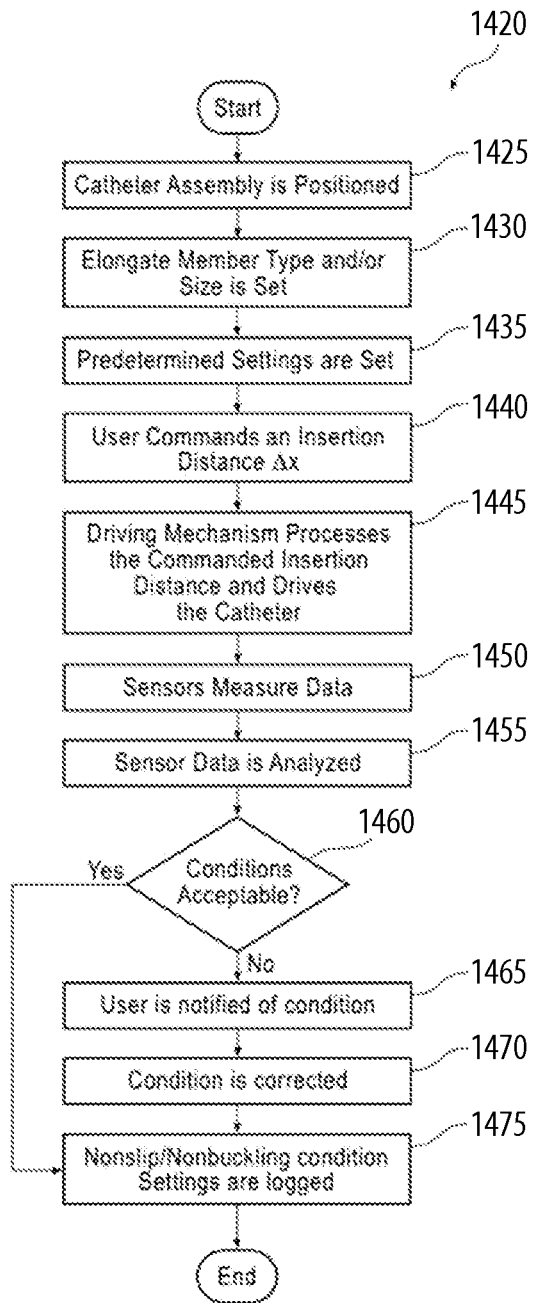
FIG. 51 illustrates a process for slip and buckling detection and correction in accordance with a preferred embodiment.

FIG. 51 illustrates an exemplary process 1420 for slip and buckling detection and correction. Process 1420 may begin at block 1425 where a user may position or set up a catheter assembly 1400. More specifically, as described above an elongate member 1402 having a proximal portion 1412 and a distal portion 1414 may be provided. Additionally, a first sensor 1404 configured to measure a proximal displacement ΔY of the elongate member 1402, a second sensor 1406 configured to measure a distal displacement ΔW of the elongate member 1402 and a drive mechanism 1408 configured to translate the elongate member 1402 along a commanded insertion distance ΔX may be provided.

Proceeding to block 1430, the user may set or input a type and/or size of the elongate member 1402 into the system. For example, a diameter of the elongate member 1402 or material associated with the elongate member 1402 may be input. As will be described further below, these inputs may be used to determine a slip and/or buckling condition of the elongate member 1402. Process 1420 may then proceed to block 1435.

At block 1435, a predetermined initial setting(s) for the drive mechanism 1408 may be set or input by the user or may be automatically loaded by the system based on a logged value, for example from a previous use or test of the elongate member 1402. The predetermined initial settings may include: an initial grip force (IGF), a minimum grip force, a maximum grip force, a minimum insertion force, and a maximum insertion force.

Proceeding to block 1440, the user may command an insertion distance ΔX for the elongate member 1402.

At block 1445, the drive mechanism 1408 may process the commanded insertion distance ΔX to drive the elongate member 1402 according to the commanded insertion distance ΔX.

At block 1450, data may be measured by one or more of the sensors. The first sensor 1404 may measure a proximal displacement ΔY of the elongate member 1402, and the second sensor 1406 may measure a distal displacement ΔW of the elongate member 1402. In addition, any of the sensors may also measure insertion force, and/or insertion speed of the elongate member 1402 and/or grip force of the drive mechanism 1408.

At block 1455, the sensor data may be analyzed or received, for example by an application configured to determine a buckling and/or slip condition of the elongate member 1402. For example, as described further below, one embodiment of a process for analyzing sensor data may include analyzing translational or displacement data from the first and second sensors 1404, 1406.

In one example, the commanded insertion distance ΔX, the proximal displacement ΔY and the distal displacement ΔW are all compared to determine a buckling and/or slip condition associated with the elongate member 1402. For example, proceeding to block 1460, a slip and/or buckling condition associated with the elongate member 1402 may be determined or detected using the sensor data discussed above in block 1455.

For example, if the commanded insertion distance sent to the drive mechanism 1408, the measured proximal displacement ΔY, and the measured distal displacement ΔW are all equal, then no slip or buckling condition is detected. More specifically, when the commanded insertion distance ΔX and displacements ΔY and ΔW of both the proximal and distal portions of the elongate member 1402, respectively are equal, then the elongate member 1402 will generally not have buckled. The lack of buckling is demonstrated by the equal displacement of the proximal portion 1412 and distal portion 1414, in this exemplary illustration. Moreover, the elongate member 1402 will also not have slipped with respect to the drive mechanism 1408 when the commanded distance ΔX provided to the drive mechanism 1408 is equal to both of the proximal and distal portion displacements ΔY and ΔW. More specifically, since the displacement of the elongate member 1402 is equal to the commanded movement distance ΔX, no slip between the drive mechanism 1408 and the elongate member 1402 is apparent.

On the other hand, if discrepancies exist between the displacement data measured by the first and second sensors 1404, 1406 and/or the commanded insertion distance ΔX, the differences between the sensor data and commanded distance may indicate the presence of a buckling and/or slip condition in the elongate member 1402.

Figure 50B:
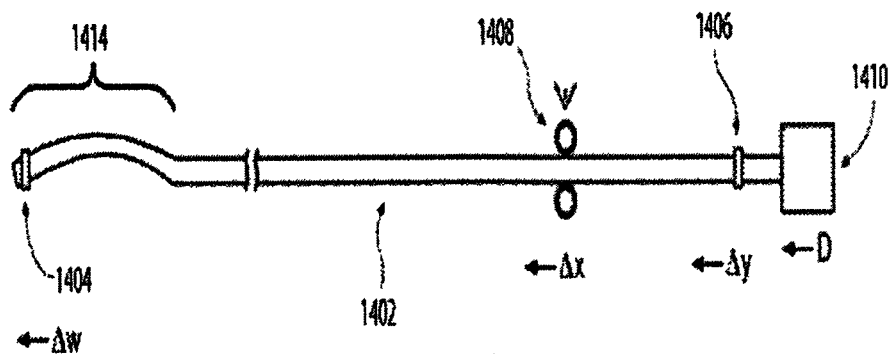

For example, if the proximal displacement ΔY is not equal to the distal displacement ΔW, as shown in FIG. 50B, this may indicate that the elongate member 1402 has buckled at some point in between the first and second sensors 1404, 1406. In one embodiment, buckling may be evidenced by a greater displacement ΔY of the proximal portion 1412 of the elongate member 1402 compared with the displacement ΔW of the distal portion 1414 of the elongate member 1402.

Additionally, if the commanded insertion distance ΔX does not equal the proximal displacement ΔY, this may indicate that the proximal portion 1412 of the elongate member 1402 has slipped with respect to the drive mechanism 1408 which is imparting insertion motion to the elongate member 1402, and accordingly a slip condition is detected.

Proceeding to block 1465, a notification of the slip and/or buckling condition(s) may be provided, for example to the user. In some embodiments, a visual or audible notification may be provided. Alternatively or in addition, haptic feedback may be provided via a control interface (not shown) of the elongate member 1402. Any notification may be of various intensities and frequencies and may include any color light, flashing light, sound, visual indicator, or text-based message on a display. Process 1420 may then proceed to block 1470.

At block 1470, the system may take corrective action with respect to any condition(s) detected in block 1465. Corrective action may be taken automatically by the system and/or drive mechanism 1408, for example without intervention by the user, or corrective action may be taken directly by the user to correct the condition, for example upon observing one of the above-mentioned indicators provided at block 1465. Upon correction of the condition(s), the drive mechanism 1408 may then continue to drive the elongate member 1402 for the remainder of the commanded distance X.

Corrective action may not be needed if, for example, there is no slip or buckling detected in the elongate member 1402, and a grip force or insertion force is at a satisfactory value. In cases where no slip or buckling condition is detected and the grip and insertion forces are satisfactory, process 1420 may proceed to block 1475.

On the other hand, if a slip or buckling condition is detected, inputs to the elongate member 1402 may be adjusted to provide a correction of the detected condition.

For example, if a slip or a partial slip condition is detected, the drive mechanism 1408 may adjust a grip force on the elongate member 1402 by increasing a grip force of the drive mechanism 1408 upon the elongate member 1402. In some embodiments, grip force may be increased until the slip condition is no longer detected, for example the commanded insertion distance $\Delta X$ is equal to the measured proximal displacement $\Delta Y$, including any corrections for reduced translation during the previously detected slip condition. Once the measured proximal displacement $\Delta Y$ is equal to the commanded insertion distance $\Delta X$ over a period of time, the slip condition is no longer present for that period of time. Process 1420 may proceed to block 1475.

In another example, if a buckling condition is detected, drive mechanism 1408 may drive the elongate member 1402 in order to correct the buckling condition, for example by slowing or even reversing insertion movement of the elongate member 1402. More specifically, buckling of the elongate member 1402 may be corrected by moving the proximal portion 1412 of the elongate member 1402 such that it is retracted away from the patient insertion site, decreasing a difference between the displacement of the proximal portion 1412 $\Delta Y$ until it is equal or substantially equal to the displacement of the distal portion 1414 $\Delta W$.

In some embodiment, other corrections may be provided by the system and/or drive assembly 1400. For example, a grip force being applied to the elongate member 1402 may be compared to a predetermined grip force range that is desired for the elongate member 1402. If the grip force is within the predetermined grip force range, then no correction need be made and the process 1420 may proceed to block 1475. On the other hand, if a grip force is below a minimum grip force recommended for the elongate member 1402, the grip force applied by the drive mechanism 1408 may be increased until the grip force is above the minimum grip force. On the other hand, if the grip force is greater than a maximum grip force desired for the elongate member 1402, the grip force may be decreased until it is below the maximum grip force. If a grip force is too high or too low, system may provide a notification, for example to the user, of the specific grip force issue. Grip force may be generally constantly analyzed to ensure the grip force remains within the predetermined grip force range.

In some embodiments, insertion force of the elongate member 1402 may be analyzed and corrected as needed. More specifically, an insertion force applied to the elongate member 1402, for example as measured by the drive mechanism 1408, may be compared to a predetermined insertion force range that is desired for the particular elongate member 1402. If the insertion force is within the predetermined insertion force range, then there is no insertion force issue and the process 1420 may proceed to block 1475.

On the other hand, if the insertion force is less than a minimum predetermined insertion force setting, this may indicate that the elongate member 1402 is not being inserted at an appropriate speed. Accordingly, an insertion speed of the elongate member 1402 applied by the drive mechanism 1408 may be increased.

If the insertion force is greater than a maximum predetermined insertion force setting, the insertion force may be adjusted, for example by decreasing an insertion speed of the elongate member 1402 or by ceasing insertion motion of the elongate member 1402. Alternatively or additionally, if the insertion force is too high, the drive mechanism 1408 may automatically adjust a grip force on the elongate member 1402. For example, by reducing a grip force on the elongate member 1402, insertion speed may be reduced by allowing some amount of slip between the elongate member 1402 and the drive mechanism 1408 to occur. Moreover, the system may provide a notification of the specific insertion force issue. The process 1420 may generally continuously analyze the insertion force to ensure insertion force is within the predetermined insertion force range or is corrected.

The above-noted corrections for slip and buckling conditions, as well as corrections to grip force and insertion force may be carried out automatically by the drive mechanism 1408, for example without requiring intervention by the user. Alternatively, corrections may be applied manually by the user, for example in response to notification(s) being provided by the system of the relevant condition(s).

Sensor data may also be used to allow the system and/or drive mechanism 1408 to "learn" appropriate insertion speed, force, and grip settings for a given elongate member 1402. For example, proceeding to block 1475, a measured grip force (or any other settings) associated with non-slip, non-buckling or otherwise satisfactory conditions for a given elongate member 1402 may be logged as the appropriate default setting for the particular elongate member 1402. Additionally, any conditions resulting in non-desirable conditions such as excessive slip, buckling, or deviations in grip force or insertion force outside desired parameters may be logged to avoid or reduce such conditions in future procedures. The settings may be used in subsequent procedures using elongate member 1402, as described above in blocks 1475 through 1470, in order to provide guidance regarding appropriate settings for the elongate member 1402 and any corrections made to the operating parameters described above. Moreover, as ideal settings may vary amongst different elongate members 1402 having different size diameters or types, the logging and memory of previous procedures and conditions resulting from various operating parameters may allow the system and/or drive mechanism 1408 to generally learn or modify desired operating parameters continuously for a number of different elongate members 1402, thereby reducing the occurrence of conditions such as slip or buckling in future procedures. The system may thereby determine appropriate default settings for a number of different elongate members 1402 having different configurations, diameters, sizes, coatings, types, and/or any other feature. Accordingly, in subsequent procedures the system may automatically load the default settings, for example grip force, based on the logged grip force. Process 1420 may then terminate.

Figure 52:
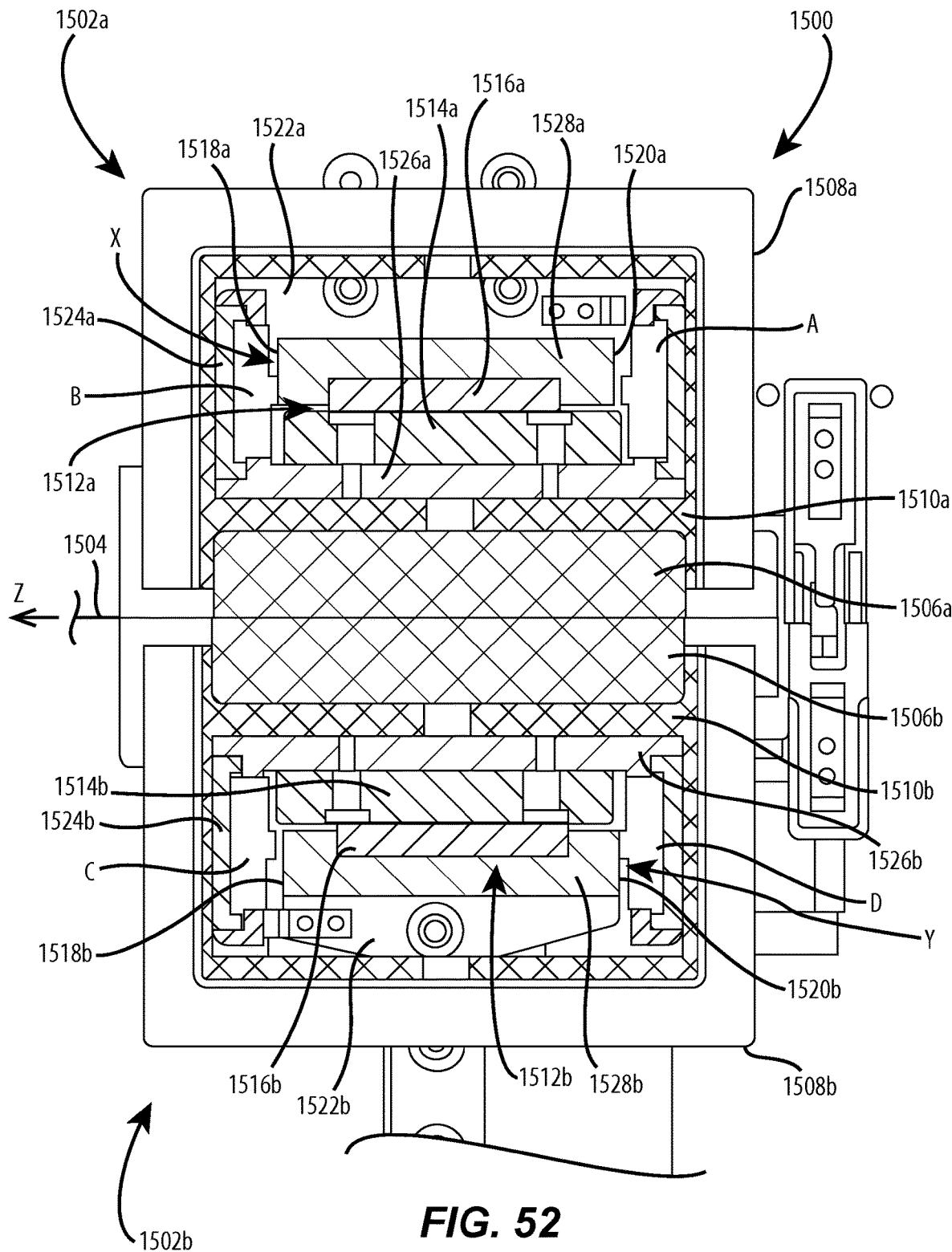
FIGS. 52 and 53 illustrate cross sectional and perspective views, respectively, of a slip detection system in accordance with an alternative preferred embodiment.
Figure 53:
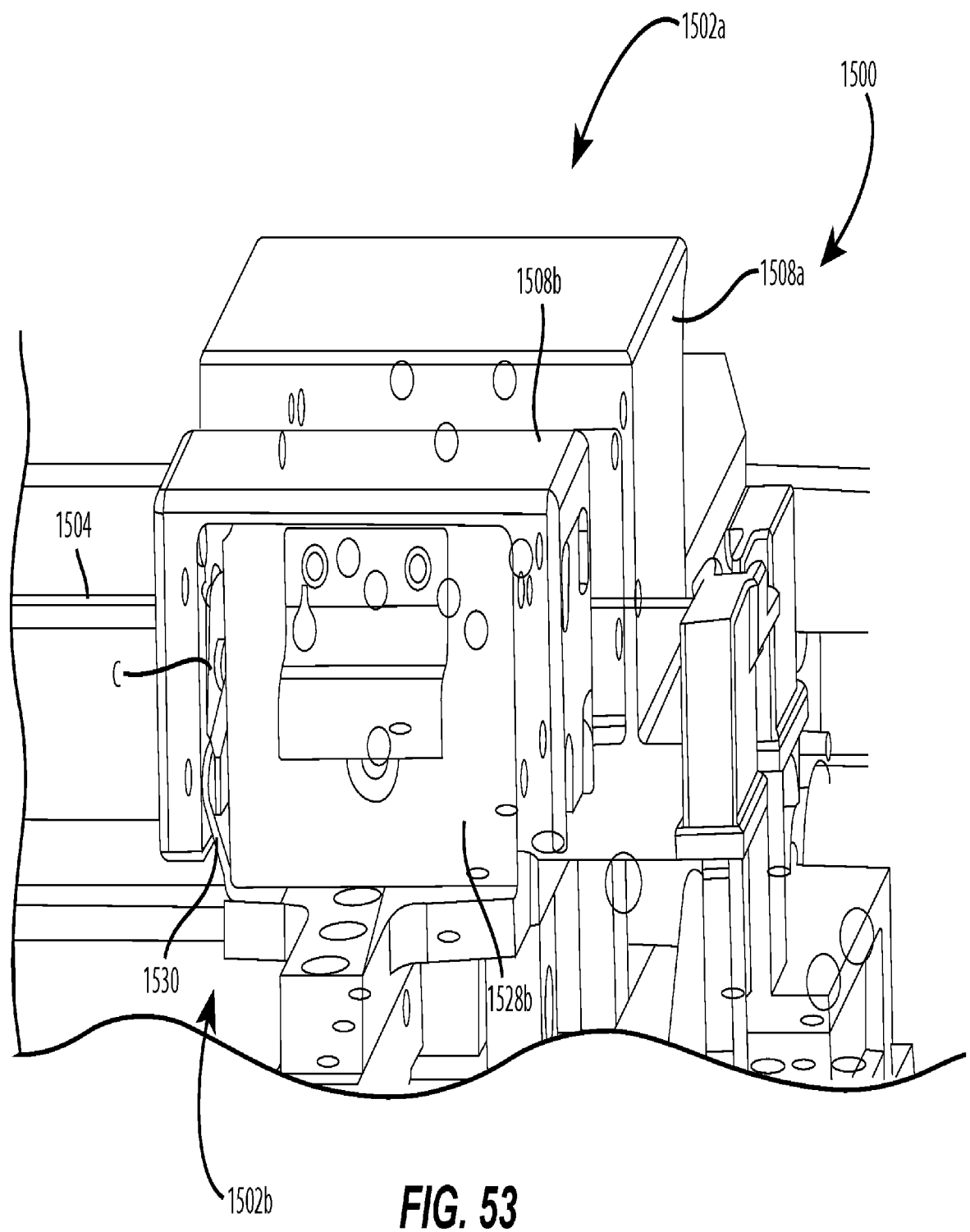

Alternatively, in some embodiments, a sensor for slip detection may include one or more force sensors, force-sensing resistors, force-pads, pressure sensors, load cells, displacement sensors, distance sensors, proximity sensors, optical distance sensors, magnetic sensors, optical encoders, or mechanical switches. FIGS. 52 and 53 illustrate a robotic catheter assembly 1500 having an active drive device with two component devices 1502a, 1502b thereof, and an elongate member 1504 disposed between the devices 1502a, 1502b. The active drive device 1502a, 1502b may be configured to drive the elongate member 1504 in an axial direction A for insertion or retraction of the elongate member. The first and second devices 1502a, 1502b of the active drive device may each generally include similar components. For example, the respective devices may include a gripper comprising pads 1506a, 1506b (otherwise referred to as a "surface") for receiving the elongate member 1504 secured in a housing 1508a, 1508b defining an interior. The pad surfaces 1506a, 1506b may engage the elongate member 1504 via friction between the surface of the pad 1506a, 1506b and the surface of the elongate member 1504. The housing 1508a, 1508b may include a sterile barrier 1510a, 1510b configured to protect the interior of the housing 1508a, 1508b, and any components disposed therein, from contaminants in the external environment. Within the housing 1508a, 1508b of each device 1502a, 1502b there may have a linear guide 1512a, 1512b including a guide rail 1514a, 1514b and a guide block 1516a, 1516b axially slidable relative to the respective guide rail 1514a, 1514b. The linear guide 1512a, 1512b (e.g., the guide rail 1514a, 1514b and guide block 1516a, 1516b) have a distal end 1518a, 1518b and a proximal end 1520a, 1520b. The first and second devices 1502a, 1502b may be coupled to a drive system or mechanism 1522a, 1522b operable to provide the axial motion to insert and/or retract the elongate member 1504, as discussed in further detail below. Accordingly, the pads 1506a, 1506b are axially slidable relative to the drive system mechanism 1522a, 1522b.

The first device 1502a may include a sensor A associated with the proximal end 1520a and a sensor B associated with the distal end 1518a. Likewise, the second device 1502b may include a sensor D associated with the proximal end 1520b and a sensor C associated with the distal end 1518b. Sensors A, B, C and D may include a force sensing device configured to measure a force applied. Additionally or alternatively, the sensors A, B, C, D may include a displacement or distance sensor configured to measure the displacement of one or both of the pads 1506a, 1506b relative to the respective drive mechanism 1522a, 1522b. According to another variation, the sensors A, B, C, D may include any sensing component configured to detect a change in relation between the pads 1506a, 1506b and the drive mechanism 1522a, 1522b, including but not limited to proximity sensors, optical distance sensors, magnetic sensors, optical encoders, mechanical switches, etc. The sensors A, B, C, D may communicate with the workstation, electronics rack and/or electronics box via an interface (not shown). The interface(s) may be configured to transmit data from the sensors A, B, C, D to the workstation, electronics rack, and/or electronics box. The interface(s) may be one-directional such that data may only be transmitted in one direction. Additionally, the interface(s) may be bi-directional, both receiving and transmitting data between the sensors A, B, C, D and the workstation, electronics rack, and/or electronics box.

The respective sensors A, B, C, D may be accommodated within the housing 1508a, 1508b which may secure the pads 1506a, 1506b. The housing 1508a, 1508b may include a single component or may include a plurality of components. For instance, the housing 1508a, 1508b may include caps 1524a, 1524b adjacent to the sensors A, B, C, D and an internal shell 1526a, 1526b for additional protection from the surrounding environment. The caps 1524a, 1524b may be removed to access the sensors without having to also remove the internal shell 1526a, 1526b. The housing 1508a, 1508b may secure the sensor B and C in place at the distal end 1518a, 1518b and secure the sensors A and D in place at the proximal end 1520a, 1520b.

In the following discussion, reference to the housing 1508a, 1508b may be synonymous with the housing 1508a, 1508b, caps 1524a, 1524b and internal shell 1526a, 1526b. The first and second device 1502a, 1502b may include an axial clearance X between at least one of the distal ends 1518a, 1518b and the respective sensor B, C and/or between at least one of the proximal ends 1520a, 1520b and sensors A, D. According to a non-limiting example, the respective clearances X, X may comprise a few millimeters or less, e.g., 0.1 mm to 5 mm. The magnitude of the clearances X, X may depend at least in part on the manufacturing tolerances associated with the assembly 1500 components.

In order to translate the pads 1506a, 1506b axially, the drive mechanism 1522a, 1522b may actuate one or both of the devices 1502a, 1502b via a drive post 1528a, 1528b. The guide rail 1514a, 1514b of the linear guide 1512a, 1512b may be coupled, fastened, fused, or otherwise adhered to the housing 1508a, 1508b, whereas the guide block 1516a, 1516b may be attached to the drive post 1528a, 1528b, which in turn may be connected to the drive mechanism 1522a, 1522b. As such, the guide rail 1514a, 1514b may be in slidable communication with the guide block 1516a, 1516b. Accordingly, the guide rail 1514a, 1514b and associated housing 1508a, 1508b may be axially slidable relative to guide block 1516a, 1516b and associated drive post 1528a, 1528b. Therefore, according to one implementation, the pad 1506a, 1506b, housing 1508a, 1508b, guide rail 1514a, 1514b and associated sensors A, B, C, D may be axially slidable relative to the guide block 1516a, 1516b and drive post 1528a, 1528b.

According to another example, the pads 1506a, 1506b and associated sensors A, B, C, D may be axially slidable relative to the housing 1508a, 1508b, which may be coupled to the guide block 1516a, 1516b and drive post 1528a, 1528b. That is, the housing 1508a, 1508b may be coupled to the drive mechanism 1522a, 1522b such that the pads 1506a, 1506b are axially slidable relative to the housing 1508a, 1508b. The overall principle operation of the devices 1502a, 1502b remains constant regardless of the implementation, and therefore for purposes of expedience will be described with respect to the housing 1508a, 1508b and pad 1506a, 1506b being axially slidable relative to the drive mechanism 1522a and 1522b. However, a skilled artisan would understand that the same principles apply equally to an axially slidable housing 1508a, 1508b relative to the pad 1506a, 1506b. In other words, slippage may be detected in response to the relative axial movement of the pads 1506a, 1506b with respect to the drive mechanism 1522a, 1522b, for example via the housing 1508a, 1508b and/or the drive post 1528a, 1528b.

Additionally, the devices 1502a, 1502b may include a bias member 1530, as shown in FIG. 53, operatively attached to the pads 1506a, 1506b. The bias member 1530 may include a spring or other mechanism configured to establish a clearance X, X associated with each pad 1506a, 1506b. Additionally or alternatively, the clearance X, X may be established at least in part due to tolerances associated with the components of each device 1502a, 1502b. The bias members 1530 may be configured to enable the guide blocks 1516a, 1516b and drive posts 1528a, 1528b and/or housings 1508a, 1508b to slide axially relative to the pads 1506a, 1506b. The respective bias members 1530 may be connected to the respective guide block/drive post and sensors, the respective guide block/drive post and housings, or any combination thereof. According to one implementation, each device 1502a, 1502b may include at least one bias member 1530 associated with one end of the pads 1506a, 1506b, for example via the respective linear guides 1512a, 1512b. For instance, each device 1502a, 1502b may include one bias member 1530 disposed on opposite ends of the guide block 1516a, 1516b and drive post 1528a, 1528b. That is, the first device 1502a may include a bias member 1530 associated with the end of the pad 1506a proximal to the axial direction, while the second device 1502b may include a bias member 1530 associated with an end of the pad 1506b distal to the axial direction Z, or vice versa. However, it is contemplated that the respective bias members 1530 may also be disposed on the same side of the pads 1506a, 1506b (e.g., both arranged on an end distal or proximal to the axial direction A). Pursuant to an example, the first and second device 1502a, 1502b may include inversely correlated clearances X, X on opposite ends of the respective linear guide 1512a, 1512b. For instance, before advancement or initiation of the drive mechanism 1522a, 1522b, the drive post 1528a and/or housing 1508a of the first device 1502a may be in a distal position and therefore have a proximal clearance X. On the other hand, the drive post 1528b and/or housing 1508b of the second device 1502b may be in a proximal position and therefore have a distal clearance X. Consequently, converse sensors A and C or B and D of first and second devices 1502a, 1502b, respectively, may detect the force of the respective bias member 1530 depending on the placement of said bias members 1530 within the device 1502a, 1502b. The biasing force of the bias member 1530 may be less than the driving force of the drive mechanism 1522a, 1522b. On the other hand, the biasing force may be greater than the resisting force of friction between the pads 1506a, 1506b and the elongate member 1504.

According to another example, each sensor A, B, C, and D may be associated with a bias member 1530. The bias members 1530 may be configured to center the linear guide 1512a, 1512b with respect to the housing 1508a, 1508b, or vice versa, when the respective device 1502a, 1502b is inactive. Therefore, the respective linear guides 1512a, 1512b may include an equidistant axial clearance X between the distal end 1518a, 1518b and sensors B, C, and between the proximal end 1520a, 1520b and sensors A, D.

During normal driving conditions, the drive mechanism 1522a, 1522b may be configured to alternate driving each respective device 1502a, 1502b such that one device is actively advancing the elongate member 1504 and the other is passively translating along with the elongate member 1504. Additionally or alternatively, the drive mechanism 1522a, 1522b may designate either the first or second device 1502a, 1502b as the active device and the other as the passive device. This may be done by monitoring the initial force on both devices and designating the device with the higher force as the active device and designating the device with the lower force as the passive device. During insertion or retraction, a driving motion or force is provided by the guide block 1516a and/or 1516b and drive post 1528a and/or 1528b, via the drive mechanism 1522a and/or 1522b, as the guide block 1516a and/or 1516b and drive post 1528a and/or 1528b abuts or otherwise communicates with the sensors A, B, C, D and housing 1508a, 1508b.

According to one implementation, the bias member 1530 may exert a force to displace the guide block 1516a, 1516b and drive post 1528a, 1528b to the distal position or proximal position to provide a clearance X on the opposite end thereof. For example, as illustrated in FIG. 52, the first device 1502a may include a bias member 1530 on the proximal end 1520a thereby displacing the guide block 1516a and drive post 1528a distally creating clearance X. The second device 1502b may include a bias member 1530 on the distal end 1520b thereby displacing the guide block 1516b and drive post 1528b proximally creating clearance X. However, a skilled artisan would understand that the placement of the bias member 1530 is discretionary, and the same principles apply with no bias member or with bias members 1530 in alternative positions. As just one example, the bias member 1530 in the first device 1502a may be arranged between the housing 1508a, guide block 1516a, and drive post 1528a distally relative to the axial direction Z, thereby axially moving the housing 1508a proximally and creating a proximal clearance X. If there are no bias members, a skilled artisan would understand that the standard tolerances during build and assembly of the parts will ensure that one device will take more of the load. Therefore, the passive device does not imply that the device is totally passive and is applying no load during advancement of the elongate member. Instead, the term passive device is used to refer to the device that has the lower force.

The respective sensors A, B, C, D may be configured to detect or measure various types of data. For instance, the sensors may be configured to detect data including a load or an advancement force $F_{ADV}$ (e.g., insertion force or retraction force) exerted via the drive post 1528a, 1528b, the housing 1508a, 1508b, and/or pads 1506a, 1506b. That is, the sensors A, B, C and/or D may be operable to detect an increase of force on the pads 1506a, 1506b and thereby detect slippage of the elongate member 1504 relative to the pad 1506a, 1506b. Additionally, data may include a bias force exerted via the bias member $F_{BIAS}$. Additionally or alternatively, the sensors A, B, C, D may be configured to detect or measure the displacement of the guide block 1516a, 1516b and drive post 1528a, 1528b relative to the respective housings 1508a, 1508b. For instance, the sensors B, C may be configured to measure a displacement $\Delta X$ of the distal end 1518a, 1518b, and the sensors A, D may be configured to measure a displacement $\Delta Y$ of the proximal end 1520a, 1520b. The sensors A, B, C and D may communicate the data to the workstation, for example, to detect slip and/or determine the likelihood of slip in response to the data received.

According to one example, the elongate member 1504 may be advanced through the active driving of the second device 1502b and the passive translation of the first device 1502a, or vice versa. That is, the second device 1502b may advance the elongate member 1504 via friction between the pad 1506b and the elongate member 1504. On the other hand, the first device 1502a may passively translate with the elongate member 1504 via friction between the elongate member 1504 and respective pad 1506a of the first device 1502a. As such, the second device 1502b may be operable to advance the elongate member 1504, while the first device 1502a may be operable to detect slippage of the elongate member 1504. A skilled artisan will appreciate, in light of this disclosure, that the exemplary description is not limited to the described implementations. Rather, the disclosure encompasses modifications or variations of the disclosed examples. For instance, while the disclosure describes a distal clearance X in the active drive device 1502b, a skilled artisan will appreciate that this arrangement may be adjusted and within the guidance of the disclosure.

During operation in direction Z, the axial force of insertion may be provided by the first device 1502a via the drive mechanism 1522a. As illustrated in FIGS. 52 and 53, the second device 1502b (e.g. passive) may include a clearance X at the distal end 1518b during advancement in direction Z in normal condition. The clearance X of the second device 1502b may be initiated via a bias member 1530, for example. The second device 1502b may passively advance in direction Z with the elongate member 1504 keeping clearance X during normal condition.

Accordingly, the measured data, e.g., total force ($F_{TOT}$), during exemplary operational normal conditions may include: sensor A ($F_A$) showing force of approximately zero (F=~0), sensor D ($F_D$) may show a force equal to force of bias member ($F_{BIAS}$); sensor B ($F_B$) may show a force of advancement ($F_{ADV}$) plus the force of bias member 1530 (F=$F_{BIAS}$), and second sensor C ($F_C$) of second device 1502b approximately zero force (F=~O)). That is, the measured parameters include: $F_A$=~0; $F_D$=$F_{BIAS}$; $F_C$=~0; $F_B$=$F_{ADV}$+$F_{BIAS}$. Additionally or alternatively, the data may take into account the proximity of the respective clearance X, X via the distance between the sensors and the associated ends of the linear guides 1512. For instance, during normal advancement conditions the clearance X between sensor A and proximal end 1520a of the first device 1502a may correspond to the clearance X between sensor C and distal end 1518b of the second device 1502b.

If, however, slippage occurs, the reaction force of elongate member 1504 may be in the direction opposite the advancement direction Z. The pad 1506b of the passive second device 1502b in this example may correspondingly move in a direction opposite direction Z with the elongate member 1504, e.g., the housing 1508b and guide block 1516b and pad 1506b may slide axially relative to the drive mechanism 1522b. Consequently, the clearance X between distal end 1518b and sensor C decreases, and sensor C may register a force and/or a change in displacement ΔX of the distal end 1518b. The detection of force or change in ΔX by the sensor C of the second device 1502b may indicate slip conditions. Additionally or alternatively, if the drive mechanism was moving the wire in the opposite direction, opposite direction Z, the clearance X in the first device 1502a may decrease as the guide block 1516a and pad 1506a translate towards the proximal position 1520a, which may likewise indicate slip conditions. According to one implementation, the change of displacement ΔX and ΔY between the normal and slip conditions, e.g., the difference of the clearance X, may be taken into account to estimate the actual position of the elongate member 1504.

In response to detecting slip conditions, measures may be taken to warn the operator, mitigate the slip hazard, and/or account for the slip to correct the slip condition and, in some circumstances, continue driving the elongate member 1504, as will be discussed below. Once the initial slip occurrence is detected, therefore, the first device 1502a (e.g., passive device pursuant to the above example) may drive the elongate member 1504 in conjunction with the second device 1502b. Accordingly, the system 1500 may achieve more advancing force than if the system 1500 were to stop or freeze after the initial slip detection/occurrence.

Figure 54:
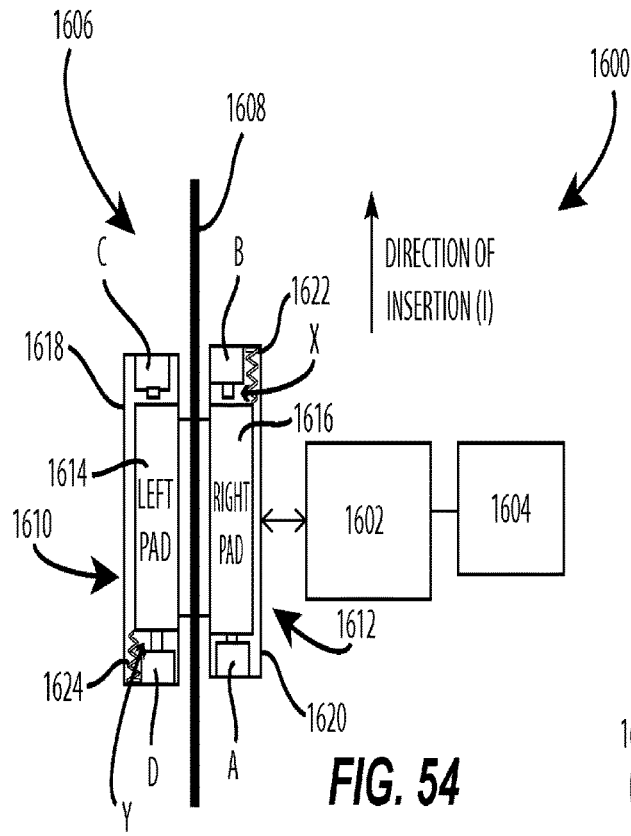
FIGS. 54 and 55 illustrate a slip detection system in accordance with an alternative preferred embodiment.
Figure 55:
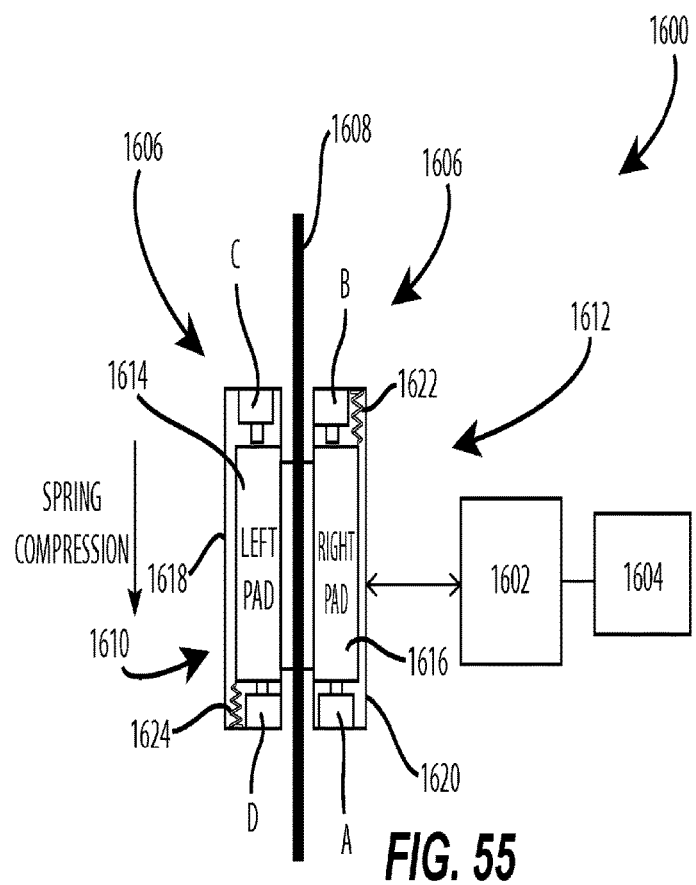

FIGS. 54 and 55 illustrate a system 1600 for detecting and correcting slip of a device relative to an elongate member. The system 1600 may be associated with catheter assembly 1500 discussed above, but a 2-dimension representation is shown to simplify the explanation of the functionality of the slip mechanism. That is, the system 1600 may represent the functionality behind actions of the robotic catheter assembly 1500. Additionally or alternatively, the system 1600 may be utilized separate from the components of the catheter assembly 1500.

Referring to FIGS. 54 and 55, the system 1600 may include a computing device having a processor 1602 having a memory 1602a in communication with a catheter assembly or drive apparatus 1606 (hereinafter referred to as a catheter assembly 1606). The processor 1602 may be separate from, or included with, at least one of the workstation, electronics rack and/or bedside electronics box. The processor 1602 may include modules (not shown) representing the functionality relating to processing sensor inputs and rendering commands or outputs to the catheter assembly to mitigate, correct, and avoid hazardous slip conditions. The processor 1602 may be configured to interact with and update the memory 1602a in response to inputs received from the catheter assembly 1606 (e.g., via sensors) and/or inputs received from the user interface (e.g., via manual inputs from the operator).

The components of the catheter assembly 1606 are illustrated schematically in FIGS. 54 and 55, for purposes of illustrating certain embodiments of the system 1600. According to one example, the catheter assembly 1606 may include an elongate member 1608 disposed between a first device 1610 and a second device 1612 configured to move in an axial direction relative to the elongate member 1608. The first device 1610 may include a first pad or surface 1614 engaging the elongate member 1608 and the second device 1612 may include a second pad or surface 1616 engaging the elongate member 1608. According to this implementation, a force sensor, load cell or other mechanism to detect a force is associated with each side of the respective pads 1616, 1614. As such, the assembly 1606 may include sensors A, B, C, and D similar to A, B, C, and D shown earlier. The first device 1610 and second device 1612 may be fixed to a housing 1618, 1620. As a result of tolerances associated with coupling the sensors between respective pads 1616, 1614 and the first and second device 1610, 1612, the first pad 1614 and associated sensors may not measure a force equal to the second pad 1616 and associated sensors. In one embodiment, the pad with the smallest clearance between the pad, sensor and housing may become the driving pad, and the other pad may measure a lower force relative to the driving pad. The force sensor associated with the other, non-driving pad may not measure the entire force of the elongate member 1608. Rather, the non-driving pad moves forward due to friction between the pads and the elongate member. Assuming device 1612 has the smallest clearance X, the catheter assembly 1606 may translate the elongate member 1608 during normal operation in a direction of insertion I via actively driving device 1612 and 1610 and the pad 1616 associated with device 1612, whereas the opposite pad 1614 (associated with device 1610) passively translates in the insertion direction I via friction between the pad 1616, 1614 and elongate member 1608.

Further, each device 1612, 1610 may include a bias member 1622, 1624 arranged on an opposite end of the pad 1616, 1614 relative to each other (e.g., the first device 1610 may include a distal bias member 1624 relative to the direction of insertion I, whereas the second device 1612 may include a proximal bias member 1622). According to one example, the bias members 1622 and/or 1624 may be a variable force bias member, for example the biasing force $F_{BIAS}$ of each biasing member 1622, 1624 may be adjustable. The respective bias members 1622, 1624 may be coupled to an end of the pad 1616, 1614 and an associated housing of the device 1612, 1610. Additionally or alternatively, the bias members 1622, 1624 may be coupled to the sensor A, B, C, D and the pad 1616, 1614. Before insertion, bias member 1622 may push second pad 1616 proximally leaving a distal clearance X, and bias member 1624 may push first pad 1614 distally leaving a proximal clearance Y. Consequently, before insertion, sensors A and C may measure an equal and opposite force F of the bias member $F_{BIAS}$, while sensors B and D may show little or no force, e.g., $F_A=F_{BIAS}$; $F_B=0$; $F_C=F_{BIAS}$; $F_D=0$.

According to one example as illustrated in FIG. 54, when driving the elongate member 1608 in the insertion direction I before slip occurs, the first pad 1614 is actively driving the elongate member 1608 while the second pad 1616 passively moves in the insertion direction I due to friction. During insertion, sensor C may be providing (or detecting) the insertion force $F_{INSERT}$ (e.g., causing a force reading), and sensor A may still detect $F_{BIAS}$, while sensors B and D measure little or no force. Accordingly, for instance during insertion without slip, $F_B=0$; $F_A=F_{BIAS}$; $F_C=F_{INSERT}+F_{BIAS}$; $F_D=0$. According to one example, $F_{BIAS}$ may be greater than the friction in the liner guide supporting the pad 1614 and 1616 to ensure the pads are located in contact with sensor C and A, respectively. However, $F_{BIAS}$ may be less than the insertion force under normal use or operation to ensure movement of pad 1614 if slippage occurs. According to one example, the distal clearance X is greater than the elasticity of the mechanism under the insertion forces experienced such that sensor B does not come in contact with pad 1616 during non-slip insertion. That is to say, during insertion without slippage, the second pad 1616 substantially maintains the clearance X.

The elongate member 1608 exerts a reaction force $F_{REACT}$ back to the pad 1614, opposite the direction of insertion I. Accordingly, while the second pad 1616 is moving with the elongate member 1608 in direction I, $F_{REACT}$ from the elongate member 1608 resists the first pad 1614 in the direction opposite insertion I. If the elongate member 1608 slips, the second pad 1616 may follow the elongate member 1608 in a direction opposite insertion I due to the slip and sensor B may see an increase in force. For example, the aggregate force includes: $F_C=F_{INSERT}+F_{BIAS}$; $F_A=0$; $F_D=0$; $F_B=F_{INSERT}-F_{BIAS}$.

After the initial slip is detected, the system 1600 may autonomously detect and counter or mitigate the slippage of the elongate member 1608 relative to the pad 1616 and/or 1614 in order to continue insertion after slip is detected. Additionally or alternatively, the system 1600 via the controller 1602 may output an alert to warn the user that slip has been detected and/or mitigated. Further, the controller 1602 may freeze out or stop insertion if the detected slip is greater than a tolerance or threshold amount (e.g., the clearance Y of sensor D and/or X of sensor B has entirely bottomed out).

According to one example, the mitigation after slip detection may involve pad 1614 and 1616 opening to release the elongate member 1608 and then immediately closing again. This may reset the slip detection mechanism and potentially allow motion to continue.

According to one example, the drive system may be designed with the capability to increase the clamp force of the pads on the elongate member. When slip is detected, the slip detection mechanism may be reset as explained above and the clamp force may be increased on the pads and then insertion of the elongate member may continue According to another example, when slip is detected, the slip detection mechanism may be reset as explained above and then the speed of insertion may be reduced potentially reducing the likelihood of further slip and then insertion of the elongate member may continue According to a further example, the bias force $F_{BIAS}$ may be increased once the point of slip has been detected. As described earlier, the $F_{BIAS}$ should be less than $F_{INSERT}$ or $F_{SLIP}$ to ensure movement of the passive pad when slip occurs. Therefore, $F_{BIAS}$ will usually start out with a low force until a point of slip is detected. Once the $F_{SLIP}$ is known, $F_{BIAS}$ may be increased using variable force bias member, for example an adjustable spring force (not shown). This allows the slip detection mechanism to be reset and motion to continue. Accordingly, the adjusted biasing force $F_{BIAS}$ may establish a new threshold from which slip is detected.

According to one implementation, the processor 1602 may be configured to execute instructions, e.g., as stored on the memory 1602a, to estimate slip force, determine various slip conditions representing the likelihood that slippage will occur, and/or control the catheter assembly 1606 during slip conditions. The processor 1602 may use similarities and symmetries inherent in the sensors A, B, C, and D to determine slippage, mitigate the issue and instruct the operator accordingly.

Per the system 1600 discussed above, since sensor C may directly measure the force applied to the elongate member 1608 by the driving of pad 1614, the force at the moment that slip is detected becomes a measured or estimated force of slip (e.g., $F_{SLIP}=F_C$ at moment of slip) for pad 1614 on the member 1608. That is to say, at the time of slip, if sensor C reads 2N of force, $F_{SLIP}=2N$, and the processor 1602 may assign a slip tolerance accordingly. As such, using both pads 1616, 1614 to drive the elongate member 1608 should be able to achieve approximately 4N of force without slip, as both first and second pads 1616, 1614 include similar characteristics. The processor 1602 may likewise associate a slip threshold with $F_{TOT}$, for example $2F_{SLIP}$, representing a maximum detected measurement until a high probability of slippage is determined, assuming a uniform friction force along the entire length of the elongate member and the pad. Additionally, the system 1600 may use more than one data set to determine the appropriate force variables, thereby adding to the accuracy of estimating the slip. For instance, the processor 1602 via the sensors A, B, C, D may measure each time initial slip occurs and average or filter the values. According to some implementations, the values may vary depending on the elongate member 1608. As such, the system 1600 includes the ability to continue driving the elongate member 1608 after the initial slip is detected, thereby allowing the system 1600 to achieve more insertion force (and elongate member 1608 displacement) than if the system 1600 were to stop or freeze upon the initial slip occurrence.

According to this example, the processor 1602 may be configured to detect slip conditions representing a likelihood of slip at the moment in response to the relationship between the total drive force $F_{TOT}$ relative to the slip tolerance $F_{SLIP}$ and the slip threshold $2F_{SLIP}$. For instance, using $F_{TOT}$, measured via the sum of forces measured at sensors C and B ($F_C$ and $F_B$, respectively), the processor 1602 may determine a slip probability or likelihood based on inputs received from the sensors A, B, C, and/or D. Accordingly, the processor 1602 may be operable to control the catheter assembly 1606 following the initial slip detection (e.g., continue driving the elongate member 1608 after the initial slip occurrence) in a few exemplary situations:

In a first condition ("Condition I"), the processor 1602 may determine slip is improbable. According to one exemplary approach, Condition I may be present when the equation $F_{TOT}=F_C+F_B<F_{SLIP}$ is true. In this instance, slip is improbable and may not occur. $F_B$ may show little force, e.g., $F_{BIAS}$, but in certain transition periods force measurements may slightly spike. The processor 1602 may be configured to detect and ultimately ignore such force spikes, for example by including a determined force measurement tolerance. In response to detecting forces satisfying the algorithm of Condition I, the processor 1602 may determine Condition I applies and continue driving the elongate member 1608.

In a second condition ("Condition II"), the processor 1602 may determine slip is unlikely. According to one example, Condition II may be determined when the equation $F_{SLIP}<F_{TOT}<2F_{SLIP}$, is true. More specifically, both first and second pads 1616, 1614 may be pushing on the elongate member 1608 at less force than the slip threshold, e.g., $2F_{SLIP}$. However, the processor 1602 may trigger Condition II as slip is still possible especially as $F_{TOT}$ increases towards the threshold $2F_{SLIP}$. That is, the closer $F_{TOT}$ is to $2F_{SLIP}$, the more likely slippage will occur. In Condition II, the catheter assembly 1606 should be able to drive the elongate member 1608 without slippage of pads 1614 or 1616. However, as $F_{TOT}$ increases towards $2F_{SLIP}$, the processor 1602 may output an alert or warning message to the user interface or an indication could be shown that there is a potential for slip, but driving the elongate member 1608 may still continue. Additionally or alternatively, when $F_{TOT}$ approaches the threshold, e.g., $2F_{SLIP}$ in this example, the processor 1602 may freeze or stop the catheter assembly 1606 altogether.

In a third condition ("Condition III"), the processor 1602 may determine slip is likely, and driving the elongate member 1608 should be stalled, halted, or otherwise stopped as slip is likely to occur. In one exemplary illustration, Condition III may be present when the equation $F_{TOT} \geq 2F_{SLIP}$ (and consequently $F_{TOT}>F_{SLIP}$), is true. In response to detecting Condition III, suspension or freezing elongate member 1608 driving may be warranted unless elongate member 1608 slip does not pose a safety hazard. Accordingly, the probability of slippage may be determined based on whether or not the $F_{TOT}$ falls within a predetermined reference point (e.g., Condition I, II, or III). In this scenario, Condition III, constant friction is assumed. However, in some instances, friction may be variable, for example, when the wire contains wet sections.

Additionally or alternatively, the processor may be configured to generate a slip score, which indicates the probability or likelihood that slip will occur in a progressive manner (e.g., on a scale of 0 to 1, with 0 representing unlikely slip and 1 representing highly likely slip, for example). The processor 1602 may receive input from the sensors A, B, C, and/or D representing force data, and determine the total driving force in response to the sensor input, for example via aggregating the detected force, taking the product, summation, average, non-linear algorithms such as fuzzy logic, etc. The processor 1602 may be configured to generate a slip score in response to the determined total driving force, and in reference to defined reference points which may be stored and/or programed into the memory 1604 (e.g., slip threshold, slip tolerance, a baseline or predetermined value associated with normal/typical driving conditions, etc.). The processor 1602 may combine or otherwise analyze the sensor inputs received and compare the data with a reference point to generate a slip condition. The higher the generated slip score, for example, the more likely slip is to occur. Additionally or alternatively, the processor 1602 may be configured to associate the slip score to slip conditions I, II, or III, and control the catheter assembly 1606 in a corresponding way. The processor 1602 may likewise be configured to associate the slip score with an output command to mitigate any hazardous slip issue. For instance, a slip score of X may be associated with continued insertion, a slip score of Y may be associated with a warning output to the user interface, and a slip score of Z may be associated with freezing the catheter assembly 1606.

In response to detecting a possible slip condition, a warning or alert may be output to the workstation. For instance, a simple warning, for example, may be presented as a status message on the display or acoustically. Graphical indicators such as those overlaying a fluoroscopic image of the elongate member 1608 may blink, change colors, or otherwise draw attention to the fact that slip is detected and/or likely. Each detected condition may likewise include a separate indicator, e.g., green, yellow and red flashing indicators for Conditions I, II, and III, respectively. Similarly, haptic cues, such as vibrating the controller, may likewise be utilized.

The direction of advancement of the elongate member 1608 may also impact how the system 1600 may react to slip. For example, if the elongate member 1608 is being retracted from the patient, there may be fewer safety risks involved and hence the system may allow motion to continue. On the other hand, if the system 1600 is being used for insertion, then there may be more safety risks and, and accordingly a more cautious approach may be chosen by the system 1600, as described above.

Additionally or alternatively, the processor 1602 may be configured to compare electrical current profiles associated with the respective force sensors to detect slip and/or determining whether the differences between measured applied forces deviate or exceed a predetermined tolerance.

Figure 56A:
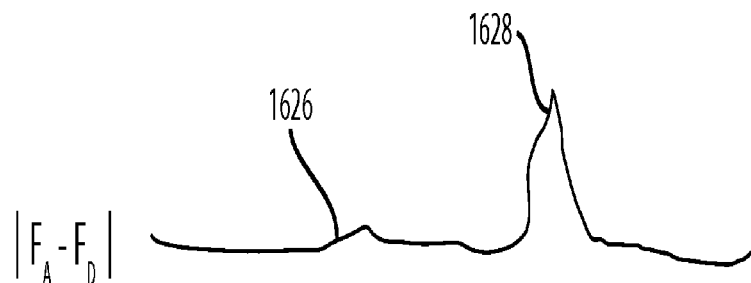
FIGS. 56A and 56B illustrate distinctive characteristics of the current profile of sensors during conditions without slip and with slip in accordance with a preferred embodiment.

For instance, the system 1600 may be configured to detect slippage based on the known correlation between sensors A and D. That is, the processor 1602 may be configured to recognize the symmetries, correlation or proportionality between corresponding sensors A, B, C, D. According to one implementation, for two sensors on the same side of the first and second pad 1614, 1616 (e.g., sensors A and D), the sum of the measured values may equal the total insertion force $F_{INSERT}$ (e.g., $F_A+F_D=F_{INSERT}$). If the first and second pads 1614, 1616 are engaged with the elongate member 1608 without slipping, the motions of the pads 1614, 1616 and elongate member 1608 may result in similar changes in measured force for both sensors A and D ($F_A$ and $F_D$). Stated alternatively, the difference between the forces of sensors A and D, $|F_A-F_D|$, may result in relatively stable readings during normal operation (e.g., without slip). As illustrated in FIG. 56A, the stable section 1626 of the graph may indicate conditions without slip. If the difference between $F_A$ and $F_D$ includes a change above a predefined tolerance, for example section 1628, this change in force difference may indicate slip. Comparing the correlation of $|F_A-F_D|$ may be used additionally or alternatively to the equations for determining Conditions I, II, and III. This lack of correlation between the two forces, e.g., $F_A$ and $F_D$, may be detected via various techniques, including using a threshold, filtering, or other numerical technique.

Figure 56B:
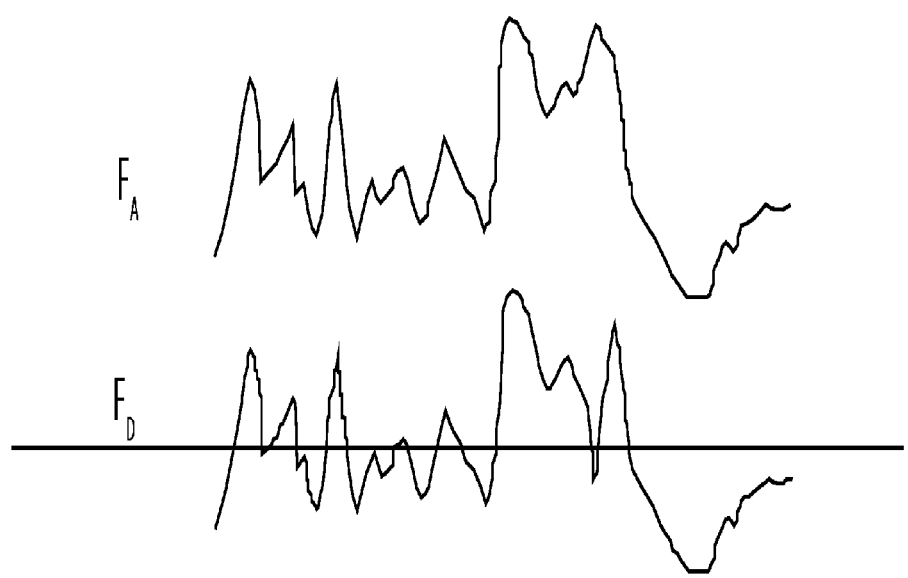

Additionally or alternatively, the system 1600 may be configured with pattern recognition functionality and therefore detect and analyze electrical current profile patterns of various sensors A, B, C, and/or D. For instance, the processor 1602 may be configured to detect anomalies or other abnormalities that may be effecting the sensors A, B, C and D, and therefore provide a check for the catheter assembly 1606 components. In the exemplary system 1600, with the use of four sensors A, B, C, D, at any given time, two sensors should be seeing similar or correlated force patterns due to symmetry of the system 1600. For instance, before slip occurs, sensors A and B may measure opposite force patterns, as with sensors C and D. As illustrated in FIG. 56B, however, when slip has occurred, sensors A and D may measure similar patterns. Corresponding to the increase of $F_D$, $F_C$ may decrease in a symmetrical way. With these predetermined tolerances stored in the memory 1604, for instance, the processor 1602 may detect anomalies in sensor data and therefore pinpoint sensors not behaving as expected, which may ultimately lead to larger system or mechanical issues. In other words, analyzing the expected force patterns (e.g., electrical current profile, force measurement readings, etc.) for each sensor in comparison to each other and checking for anomalies that could ensure the sensors A, B, C, D and pads 1614, 1616 are working properly. Additionally or alternatively, utilizing force pattern detection and/or subtraction of forces from sensors on the same pad (e.g., A-B or C-D) allows the system 1600 to account for noise, temperature drift, hysteresis, etc. of the sensors. Similarly, signal filtering may be employed to enhance the force pattern detection and recognition.

Figure 57:
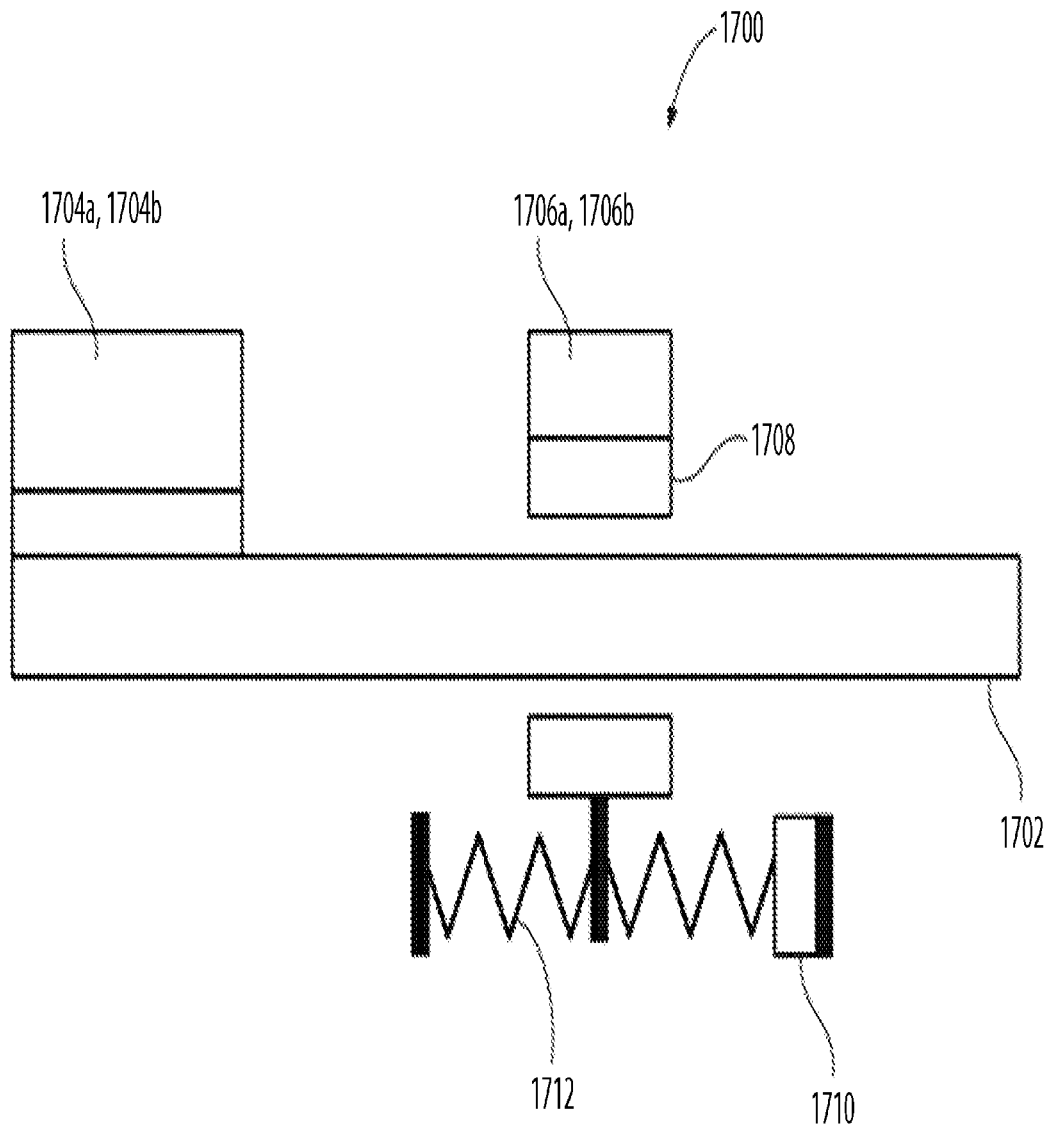
FIGS. 57 and 58 illustrate a slip detection system in accordance with an alternative preferred embodiment.
Figure 58:
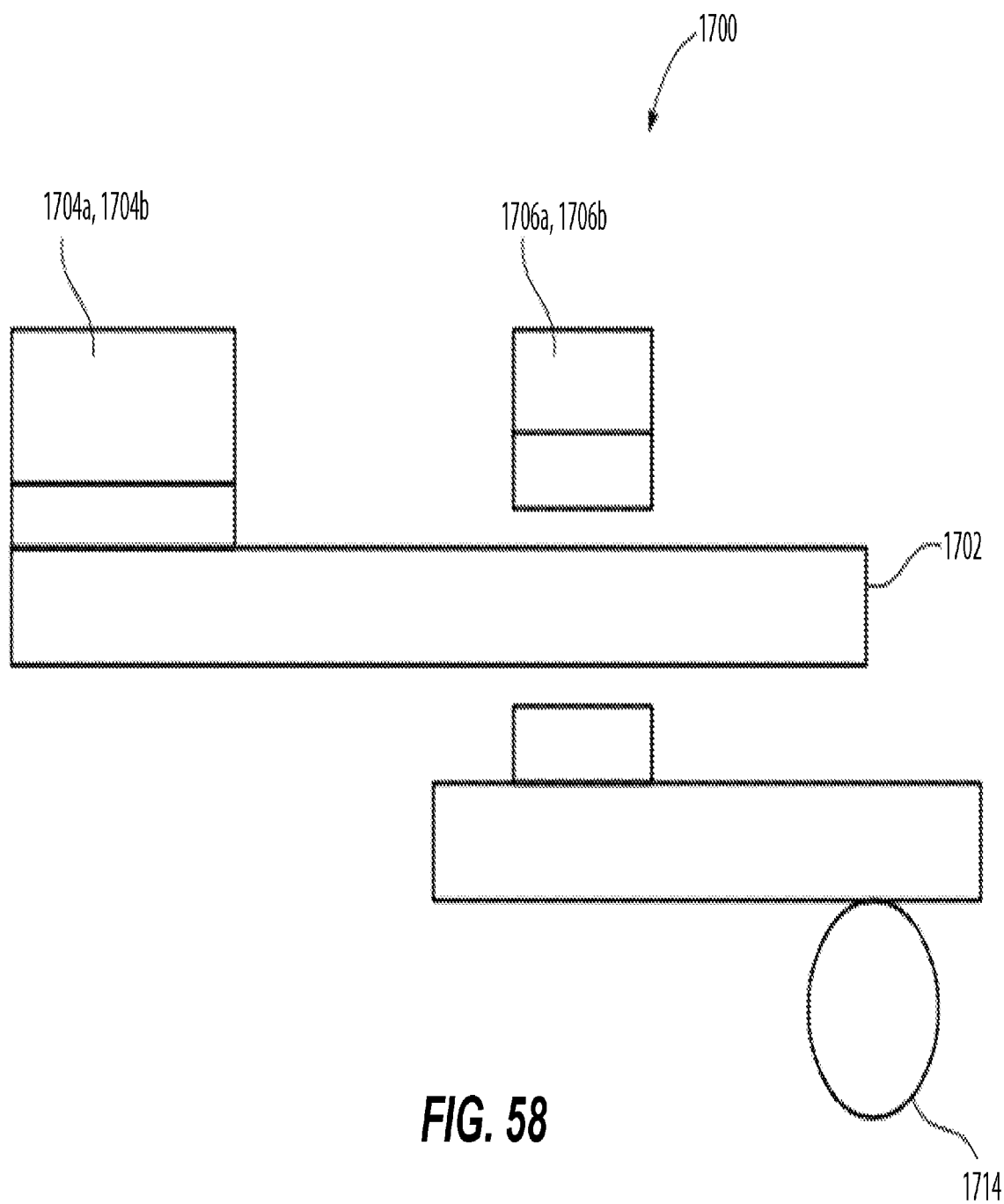

FIGS. 57 and 58 illustrate an alternative embodiment of a slip detection system including a force gauge, linear encoder, or linear potentiometer for measuring a slip condition of an elongate member. As shown in FIGS. 27 and 28, a dynamic gripper 1700 may include a gripper arm 1702 configured to move in the axial direction and rotational direction. The pair of opposing pads 1704*a*, 1704*b*, referred to hereinafter as dynamic pads, may be fixed to the gripper arm 1702. As explained above, the dynamic pads 1704*a*, 1704*b* may be configured to engage the elongate member to enable the dynamic gripper 1700 to grip the elongate member. The dynamic gripper 1700 may also include a pair of passive pads 1706*a*, 1706*b* also configured to engage the elongate member when the dynamic gripper 1700 grips the elongate member. The passive pads 1706*a*, 1706*b* may be slidably connected to the gripper arm 1702 via a linear bearing 1708, such as a sleeve bearing carriage or a plastic carriage. This may allow the passive pads 1706*a*, 1706*b* to be able to engage the elongate member at substantially the same time as the dynamic pads 1704*a*, 1704*b* and to rotate with the dynamic pads 1704*a*, 1704*b*, yet move in the axial direction along the gripper arm 1702 independent of the dynamic pads 1704*a*, 1704*b* and the gripper arm 1702. The dynamic pads 1704*a*, 1704*b* and the passive pads 1706*a*, 1706*b* may each have a defined range of motion, for example a maximum distance they can travel in the axial direction, where the range of motion of the dynamic pads 1704*a*, 1704*b* is the same as that of the dynamic gripper 1700 described above.

While FIGS. 57 and 58 depict the passive pads 1706*a*, 1706*b* as being positioned behind the dynamic pads 1704*a*, 1704*b* relative to the direction of axial movement during insertion, it should be appreciated that the passive pads 1706*a*, 1706*b* alternatively may be positioned in front of the dynamic pads 1704*a*, 1704*b*.

In some embodiments, the dynamic gripper 1700 may further include a measurement device 1710 configured to measure the distance traveled in the axial direction by the passive pads 1706*a*, 1706*b*. The measurement device 1710 may be, but is not limited to, a force gauge, as explained in more detail below, a linear encoder, or a linear potentiometer. Because the passive pads 1706*a*, 1706*b* move in the axial direction independently of the dynamic pads 1704*a*, 1704*b* and the gripper arm 1702 as explained above, the measured distance may or may not be the same as the distance the gripper arm 1702 may be commanded to move (i.e., the commanded distance). If the measured distance is less than the commanded distance, this indicates that the dynamic pads 1704*a*, 1704*b* may not be properly engaged with the elongate member and as such, that there may be slip. In such an event, the drive apparatus may be configured to generate an alarm or other alert signal to notify an operator of the system of the slippage. The operator may then stop the movement of the dynamic gripper 1700 such that the operator may re-grip the elongate member, and/or open the belts and dry the mechanism. The alarm may alternatively be generated by a computer (not shown) of the system in communication with the drive apparatus. Alternatively or in addition to the generating of the alarm, the drive apparatus may automatically stop the movement in the axial direction and/or mechanically compensate for the slippage, for example, by automatically increasing the grip force of the dynamic gripper 1700 on the elongate member such that no user input may be required.

In one embodiment, as shown in FIG. 57, a spring 1712 may be operatively attached to the passive pads 1706*a*, 1706*b* or to the linear bearing 1708. The spring 1712 may be fixed at least one end. The spring 1712 generally may be configured to enable the passive pads 1706*a*, 1706*b* to move in the axial direction with the elongate member when the dynamic gripper 1700 is gripping the elongate member and the gripper arm 1702 is moving in the axial direction, and to return the passive pads 1706*a*, 1706*b* to an original axial position when the dynamic gripper 1700 releases the elongate member. To achieve this, the spring constant of the spring 1712 should be low enough to not hinder the axial movement of the elongate member, yet have enough stiffness to return the passive pads 1706*a*, 1706*b* to center against the sources of friction in the system. Furthermore, the range of motion of the passive pads 1706*a*, 1706*b* may be approximately twice the range of motion of the dynamic pads 1704*a*, 1704*b*.

Where the measurement device 1710 is a force gauge, as mentioned above, it may be attached to a fixed end of the spring 1712. The force gauge may be configured to measure an applied force on the spring 1712 when the passive pads 1706*a*, 1706*b* are moving axially with the elongate member. The measured force may then be used to calculate the axial distance traveled by the passive pads 1706*a*, 1706*b* by a processor (not shown). The processor may be part of the drive apparatus or may be a computer in communication with the drive apparatus and/or the measurement device 1710.

In an alternative embodiment, as shown in FIG. 58, a motor 1714, such as a servo motor, may be operatively attached to the passive pads 1706a, 1706b or to the linear bearing 1708 in lieu of the spring 1712. The motor 1714 may be attached to the passive pads 1706a, 1706b via any device configured to translate the rotational movement provided by the motor 1714 into linear movement, such as a rack and pinion. The motor 1714 may be configured to enable the passive pads 1706a, 1706b to move in the axial direction with the elongate member when the motor 1714 is not activated, and to return the passive pads 1706a, 1706b to an original axial position when the dynamic gripper 1700 releases the elongate member and the motor 1714 is activated. To achieve this, the motor 1714 generally may have low gearing attached to the axis. In this approach, the dynamic pads 1704a, 1704b and the passive pads 1706a, 1706b may have approximately the same range of motion.

In some embodiments, the passive pads 1706a, 1706b may be instrumented with a load cell configured to measure the force on the insertion axis. Then, the passive pads 1706a, 1706b may be served to mirror the movement of the dynamic pads 1704a, 1704b to save range of motion. A control loop may be wrapped around the load cell, a motor operatively connected to the dynamic pads 1704a, 1704b, and a rotary encoder mounted on the motor. The motor could be small and highly geared, and the rotary encoder may be configured to take position measurements. This approach may allow for flexibility in the control of the dynamic pads 1704a, 1704b as they may essentially "float" similar to haptic devices that remove the effect of friction, thereby enabling the dynamic pads 1704a, 1704b to follow the wire motion easily. Furthermore, the passive pads 1706a, 1706b may be floating in front of or behind the dynamic pads 1704a, 1704b. When the dynamic pads 1704a, 1704b and the passive pads 1706a, 1706b engage the elongate member, the dynamic pads may be driven by the motor and the only force on the passive pads may be the motion of the elongate member.

Figure 59:
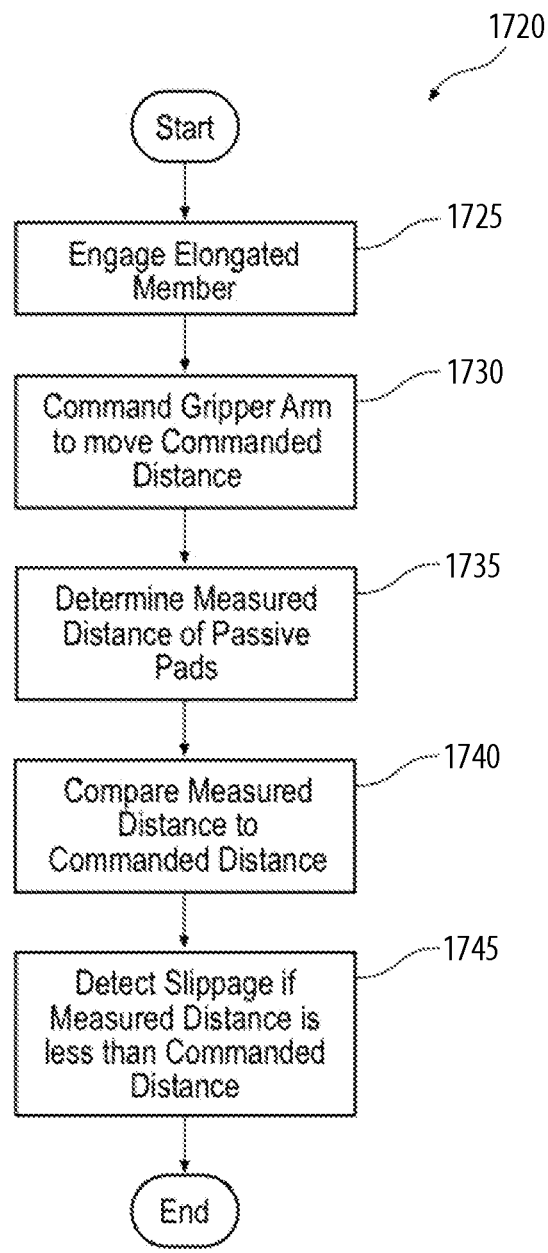
FIG. 59 illustrates a process for detecting slip in accordance with a preferred embodiment.

Referring now to FIG. 59, a method 1720 for detecting slip of a grip on the elongate member by the dynamic gripper 1700 is shown. Method 1720 begins at block 1725 in which the pair of dynamic pads 1704a, 1704b and the pair of passive pads 1706a, 1706b engage the elongate member such that the dynamic gripper 1700 grips the elongate member. At block 1730, the gripper arm 1702 is commanded to move a commanded distance in the axial direction. Because the dynamic pads 1704a, 1704b are attached to the gripper arm 1702, as explained above, and are engaged with the elongate member, the elongate member moves in the axial direction with the gripper arm 1702. Furthermore, because the passive pads 1706a, 1706b are also engaged with the elongate member, the passive pads 1706a, 1706b also move in the axial direction with the elongate member. At block 1735, the measurement device 1710 determines a measured distance of the passive pads 1706a, 1706b in the axial direction. As explained above, the measurement device 1710 may include, but is not limited to, any one of or combination of a force gauge, a linear encoder, and a linear potentiometer. At block 1740, the measured distance is compared with the commanded distance. At block 1745, slip between the dynamic pads 1704a, 1704b and the elongate member is detected if the measured distance is less than the commanded distance. Method 1720 may end after block 1745.

However, after detecting slip, method 1720 further may include generating an alarm or other alert signal to notify the operator of the system of the slip condition. As explained above, the operator may then stop the movement of the drive apparatus such that the operator may realign the elongate member, and/or open the belts and dry the mechanism. In addition to or in lieu of the generating of the alarm, method 1720 may include automatically stopping the movement in the axial direction and/or mechanically compensating for the slippage, for example, by automatically increasing the grip force such that no user input may be required.

Prior to ending, method 1720 may also include releasing the grip by the dynamic pads 1704a, 1704b and the passive pads 1706a, 1706b. This may first require a static gripper, as described above, to grip the elongate member such that the position of the elongate member is not compromised. This may be necessary if the dynamic gripper 1700 has reached the end of its range of motion, but has not yet traveled the entire commanded distance. While the static gripper is gripping the elongate member, the dynamic gripper 1700, and therefore the dynamic pads 1704a, 1704b, may be reset to the start of its range of motion. In addition, the passive pads 1706a, 1706b likewise may automatically return to their original axial position. As explained above, this may be accomplished by the spring 1712, the motor 1714, or any other similar device or apparatus.

Figure 60:
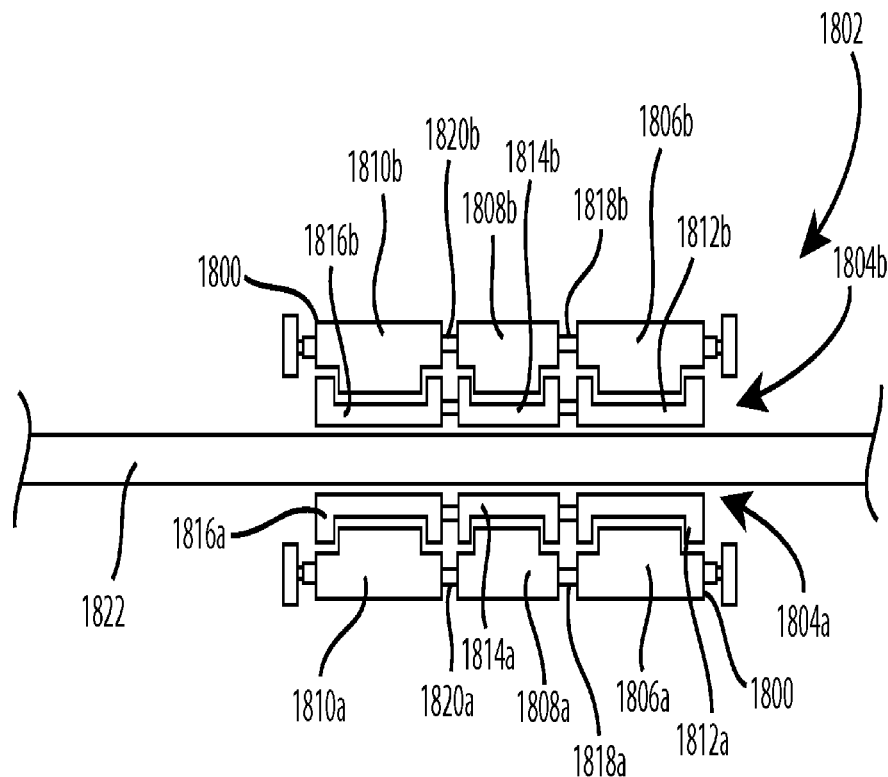
FIGS. 60-62 illustrate a slip detection system in accordance with an alternative preferred embodiment.

FIG. 60 illustrates an alternative embodiment of a slip detection system including one or more strain gauges for detecting and managing a slip condition. The slip detection system described below may be employed with any pad/gripper active drive mechanism described above. For example, clamp 1800 may be incorporated into a dynamic gripper, as described above. Accordingly, a dynamic gripper may include clamp 1800, which generally interfaces directly with the elongate member and facilitates gripping of the elongate member. Alternatively, a gripper may comprise clamp 1800, and may include one or more segments flexibly coupled together and interposed by strain gauges. Dynamic gripper 1802 may comprise a clamp 1800 having a pair of opposing pads 1804a, 1804b, respectively.

As shown in FIG. 60, clamp 1800 may comprise a first set of clamp segments 1806a, 1808a, 1810a opposing a second set of clamp segments 1806b, 1808b, 1810b, respectively. Each set of clamp segments may be configured for axial motion, for example in the direction of the arrow shown in FIG. 60, with respect to the other set of clamp segments.

Pads 1804a and 1804b may each comprise a plurality of first pad segments 1812a, 1814a, 1816a and second pad segments 1812b, 1814b, 1816b, respectively. Each pad 1804a, 1804b may have any number of segments, for example two, three (as shown), or more. Each of the pad segments may be configured to move axially with respect to the other pad segments included in the same set. For example, a pad segment may move axially with respect to an adjacent pad segment in response to different friction conditions between the different pad segments with respect to an elongate member such as a catheter.

First clamp segments 1806a, 1808a, 1810a and second clamp segments 1806b, 1808b, 1810b may each be interposed by first strain gauges 1818a, 1818b and second strain gauges 1820a, 1820b, respectively, that are each configured to provide a strain signal. The first strain gauges 1818a, 1818b and second strain gauges 1820a, 1820b may alternatively be interposed between first pad segments 1812a, 1814a, 1816a and second pad segments 1812b, 1814b, 1816b, respectively. Although the first strain gauges 1818a, 1818b may be separated from the pad segments 1812, 1814,

1816, mounting first stain gauges 1818*a*, 1818*b* between the clamp segments 1806, 1808, 1810 may allow for more precise measurement of relative movement between the pad segments 1812, 1814, 1816.

Further, in some embodiments, the pad segments 1812, 1814, 1816 may be removable from the clamp segments 1806, 1808, 1810, and/or may be incorporated into a sterile barrier (e.g. sterile drape) allowing the clamp segments 1806, 1808, 1810 to remain outside a sterile environment and potentially reducing costs. For example, a drive system as described above, may be positioned under a sterile drape, such that the drive system remains outside of the sterile field. In some embodiments, pad segments 1812, 1814, 1816 may be positioned in the sterile field on the clamp segments 1806, 1808, 1810 covered by the sterile drape, such that the sterile drape provides an interface between the pads and clamps. In some embodiments, pad segments 1812, 1814, 1816 and clamp segments 1806, 1808, 1810 may be positioned in the sterile field, such that the pad segments and clamp segments are replaced after each use. Further, the elongate member may be positioned within the sterile field and not covered by the sterile drape, such that the sterile drape is positioned on the drive system in a configuration that allows unrestricted movement of the elongate member. Moreover, the sterile drape may be positioned between the pad segments 1812, 1814, 1816 and any other portion of the drive system (e.g., sensors and clamp segments 1806, 1808, 1810), for example, to insulate the sterile field from any non-sterile portions of drive system. In addition, any portions of drive system (e.g., the sterile drape and pad segments 1812, 1814, 1816) may include a sterilizable or disposable material, may be packaged in a substantially sterile condition, and/or may be configured for single patient use. Adjacent clamp and pad segments may each be interposed by a gap to help isolate each strain signal. Axial motion between adjacent clamp and pad segments may be measured by the interposed strain gauge to determine if the elongate member 1822 is slipping with respect to the adjacent clamp and pad segments during insertion or retraction.

First strain gauges 1818*a*, 1818*b* and second strain gauges 1820*a*, 1820*b* may be configured to collect strain data including the differences in axial force, along the elongate member 1822, to determine when dynamic gripper 1802 is beginning to slip with respect to elongate member 1822. Strain data may be used to determine when to stop the dynamic gripper 1802 from driving the elongate member 1822. System may notify the user to service dynamic gripper 1802, for example, by drying the pads 1804*a* and 1804*b*. Alternatively, system may automatically adjust dynamic gripper 1802 to reduce slip, for example, by increasing the transverse force applied to grip the elongate member 1822.

First pad segments 1812*a*, 1814*a*, 1816*a* and second pad segments 1812*b*, 1814*b*, and 1816*b* may allow dynamic gripper 1802 to compress and expand axially. By attaching first strain gauges 1818*a*, 1818*b* and second strain gauges 1820*a*, 1820*b*, the strain data may indicate whether each of pad segments 1812*a*, 1814*a*, 1816*a*, 1812*b*, 1814*b*, and 1816*b* is slipping or substantially maintaining the transverse force on elongate member 1822. Any or all of pad segments 1812*a*, 1814*a*, 1816*a*, 1812*b*, 1814*b*, and 1816*b* may have similar or different sizes, shapes, materials, or gripping forces, for example, to increase the difference in grip between the adjacent pads. Each set of pad segments may be configured to compress or expand in an axial direction relative to each other. Also, each set of pad segments may be configured to resist deflection in the transverse direction, perpendicular to the length of elongate member 1822, and rotation about the longitudinal axis of elongate member 1822.

The embodiments herein may provide a more robust design than using force sensors that measure the overall pad force alone. A strain signal of strain data between two or more adjacent pads may have less noise, for example, because one pad may slip before another pad. This difference may be further increased by varying the material or transverse force on the pad segments to ensure one pad segment slips before another pad segment.

To better interpret the behavior of elongate member 1822 in light of the strain data, it may be beneficial to differentiate strain signals reflecting a slipping signal indicating slip of elongate member 1822 from a gripping signal indicating normal grip with respect to elongate member 1822. To assist with this, different materials may be utilized for selected pad segments. If the material of one pad segment has a higher friction coefficient, that pad segment may maintain grip relative to elongate member 1822 better and facilitate a more reliable slip signal than a pad segment with a lower friction coefficient material. The materials for each pad segment may be selected for the desired performance under a given condition. For example, one material may be better for imparting rotational movement of the elongate member 1822, particularly where relative vertical motion between opposing pads is used to impart rotational movement, while another material may be better for insertion or axial movement. Alternatively, a dampener such as a spring may be utilized on one or more of the pad segments to reduce the grip, thereby differentiating the strain signals for those pad segments.

Dynamic grippers 1802 may also include one or more sensors, for example piezoelectric sensors, to increase the accuracy and robustness of slip detection. The piezoelectric sensor may provide a signal in response to a pressure change relative to pads 1804*a*, 1804*b*, for example, due to vibration from slip. One or more piezoelectric sensors may be embedded into or mounted on pads 1804*a*, 1804*b*, clamp 1800, or any other segment attached to the pads or clamp. As an example, the piezoelectric sensors may be mounted on each clamp 1800 and in contact with either or both of pads 1804*a*, 1804*b*. Clamp 1800 may be etched to have a groove in a middle portion of clamp 1800 to receive the piezoelectric sensor, for example, to limit the grip force experienced by the piezoelectric sensor. An output of the piezoelectric sensor may be utilized in conjunction with the strain data to detect slips in the elongate member 1822 relative to grippers 1802.

For example, the piezoelectric sensor may include a polyvinylidene fluoride film (referred to as "PVDF film"). PVDF film is a relatively flexible, thin film capable of detecting strain velocity including relatively small changes in strain. This type of sensor produces a voltage output based on strain velocity to detect a slip condition based on a threshold output voltage indicating incipient slip. In addition, two or more pad segments may allow detection of slip propagation based on their relative motion. For example, a slip detected at a leading pad may indicate impending slip on a trailing pad. Using this information, the grip force could be dynamically adjusted to reduce or prevent the slip on the trailing pad from occurring, for example, by reducing the insertion speed to retain control of elongate member 1822. In addition, embodiments may include ridges to make signal detection more reliable.

Figure 61:
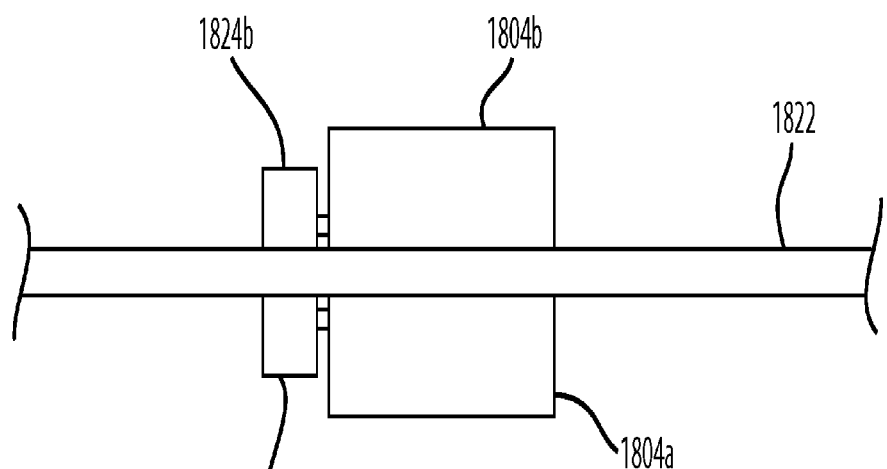

As shown in FIG. 61, dynamic gripper 1802 may include a set of opposing pads 1824*a*, 1824*b* that may be independently operable with respect to opposing pads 1804*a*, 1804*b*. Pads 1824*a*, 1824*b* may be a different size (e.g. smaller) with a different (e.g. higher) friction coefficient relative to pads 1804*a*, 1804*b*. Pads 1824*a*, 1824*b* may be configured to independently detect axial or rotational slip with respect to elongate member 1822. Alternatively, pads 1824*a*, 1824*b* may be segments of pads 1804*a*, 1804*b*, respectively. Strain gauges may be positioned between each of pads 1824*a*, 1804*a* and pads 1824*b*, 1804*b*. Some embodiments may also include a separate mount that detects forces.

Figure 62:
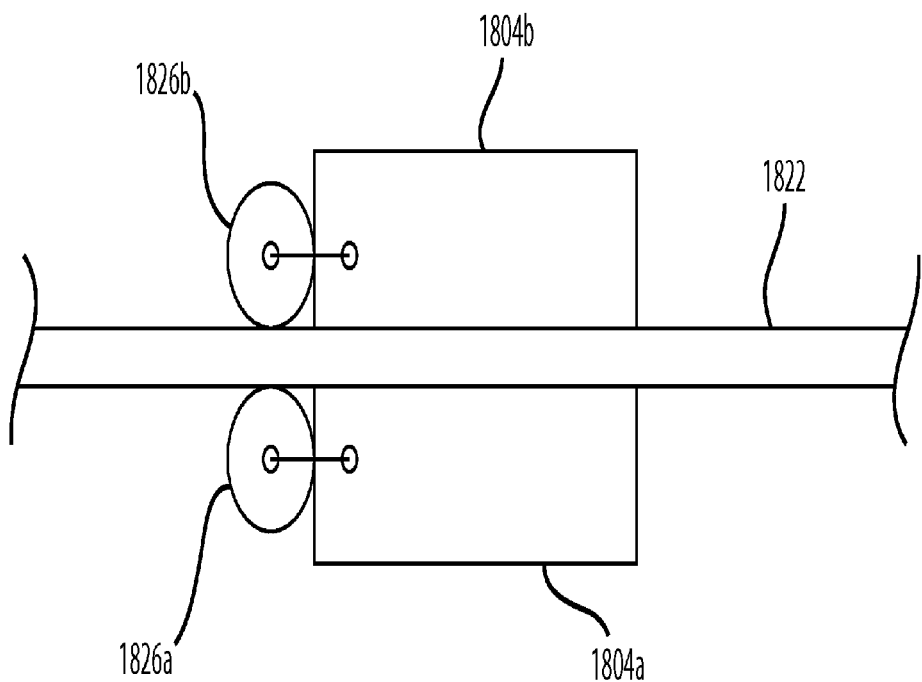

In some embodiments, as shown in FIG. 62, idler wheels 1826*a*, 1826*b* may be connected to pads 1804*a*, 1804*b*, for example for optical slip detection. Idler wheels 1826*a*, 1826*b* may have a surface material with a larger friction coefficient, for example, to detect slip in the axial direction. Idler wheels 1826*a*, 1826*b* may each include a roller with an encoder that may be coupled to pads 1804*a*, 1804*b*, respectively. While pads 1804*a*, 1804*b* move with respect to elongate member 1822, idler wheels 1826*a*, 1826*b* may roll along elongate member 1822 to measure axial movement with respect to elongate member 1822. Alternatively, idler wheels 1826, 1826*b* may each include a holonomic wheel, for example, including rollers mounted on the circumference of each wheel at an angle approximately perpendicular to the rotational axis of each wheel to simultaneously measure axial and rotational movement with respect to elongate member 1822.

In some embodiments, a slip detection system is incorporated into the active drive systems disclosed herein. The slip detection system tracks the motion or movement of the guide wire without utilizing or extracting substantial amounts of energy from movement of the guide wire. Additionally, as will be discussed in more detail below, the slip detection system is configured so that data related to the position of the guide wire and its movement is transferred wirelessly to a tracking assembly, allowing a more sterile environment for tracking the guide wire as the encoding device may be hermetically sealed with the active drive mechanisms.

In one embodiment, the slip detection system includes an encoder assembly and a tracking assembly in wireless communication with the encoder assembly. The encoder assembly includes an idler wheel, a tracking wheel, one or more tracking features connected to or defined by the tracking wheel, a tracking sensor, and a transmitting device. The idle wheel and the tracking wheel are rotatable wheels driven by movement of the guide wire and typically have a low coefficient of friction and require little energy from the guide wire in order to be rotated.

The tracking features are connected to the tracking wheel and are selected based on the type of characteristics sensed by the tracking sensor. For example, in one embodiment, the tracking sensor is an optical sensor and the tracking features form optically distinguishable elements on the tracking wheel (e.g., painted elements, reflective elements, apertures, or the like). As another example, the tracking sensor may be a magnetic sensor (such as a Hall effect sensor) and the tracking features may be specifically polarized magnetic elements. The tracking features and the tracking sensor are selected such that little or no mechanical contact is required between the sensing element and the tracking wheel. This allows the encoding assembly to track the guide wire without the guide wire transmitting some mechanical energy (e.g., torque) to the encoding assembly, increasing the efficiency of the drive assembly for the guide wire and also helping to reduce the risk of slippage.

The transmitting device is in communication with the tracking sensor and receives tracking data corresponding to the position of the guide wire from the tracking sensor. The transmitting device then transmits the data to the tracking assembly. Examples of the transmitting device include a radio wave transmitter (e.g., Bluetooth, WiFi, or the like), an acoustic transmitter such as a piezo electrical transducer, an optical transmitter, an inductive coupling, or the like.

The tracking assembly is in wireless communication with the encoder assembly. The tracking assembly includes a computing device and a receiver. The receiver is in wireless communication with the transmitter and is selected based on the type of data transmission used by the transmitter. For example, in instances where the transmitter is a radio wave transmitter, the receiver is a radio wave receiver. The receiver is configured to receive data from the transmitter of the encoder assembly and provides the data to the computing device. The computing device receives data from the receiver, optionally decodes the data, and analyzes the data to determine whether slippage has occurred, is likely to occur based on movement of the guide wire, and may provide an alert such as an alarm, notification, or the like, to a doctor or system operator regarding the state of the guide wire.

In operation, as the guide wire is driven, such as by one of the active drive mechanisms disclosed herein, the guide wire rotates the tracking wheel and/or idler wheel. As the tracking wheel is rotated, the tracking sensor detects changes in position or movement of the tracking features on the tracking wheel. The position or guide wire data is transmitted from the tracking sensor to the transmitter which then wirelessly transmits the data to the receiving device of the tracking assembly. The receiving device provides the tracking data to the computing device, which in turn determines whether a slip has occurred, the location of the guide wire, and/or other positional related information for the guide wire.

Figure 63:
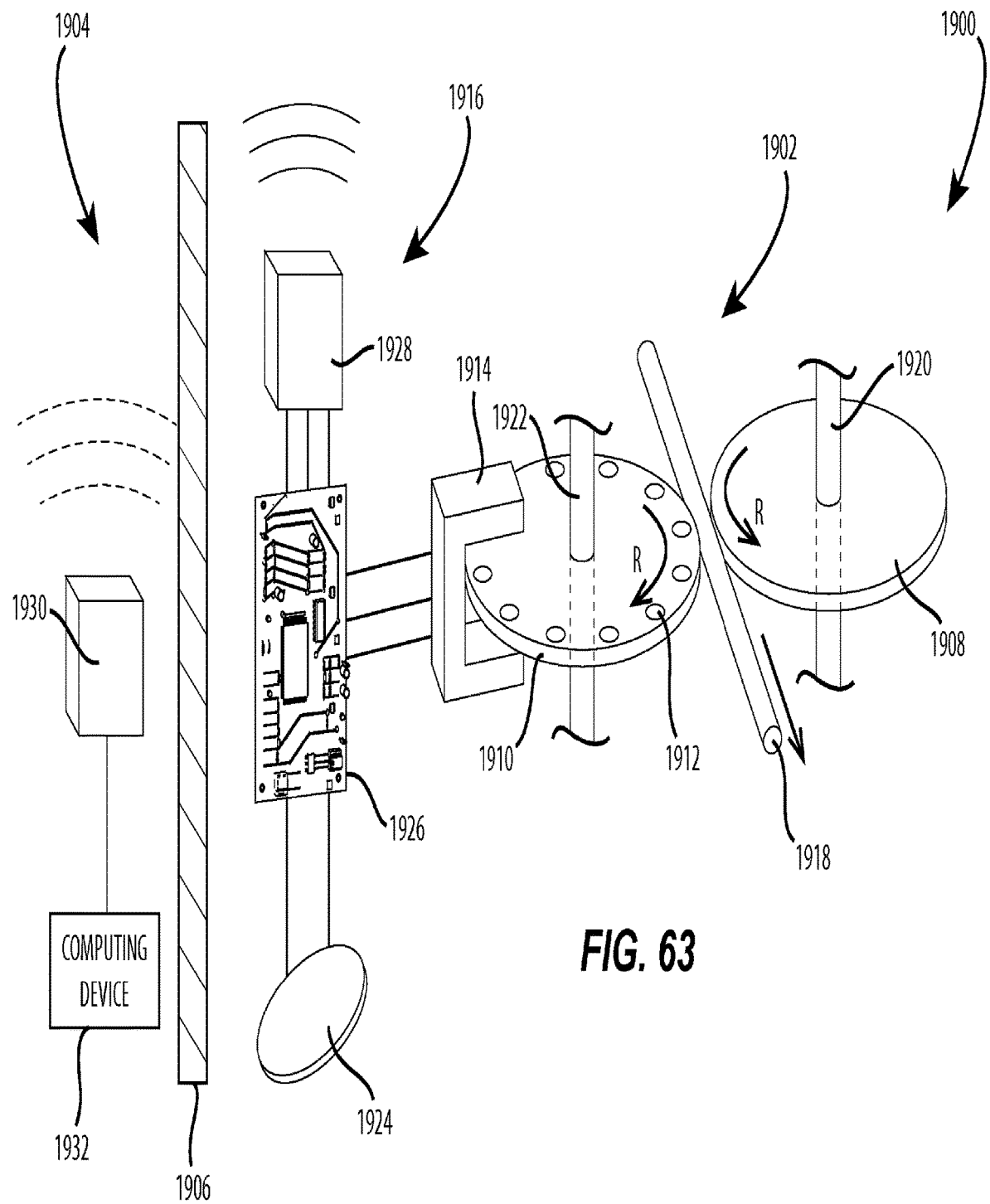
FIG. 63 illustrates a perspective view of a slip detection system in accordance with an alternative preferred embodiment.

Turning back now to the figures, the slip detection assembly will now be discussed in more detail. FIG. 63 is a perspective view of an example of the slip detection assembly. With reference to FIG. 63, the slip detection assembly 1900 includes an encoding assembly 1902 and a tracking assembly 1904, each will be discussed in turn below.

The encoding assembly 1902 is typically housed within a sterile compartment for the active drive system. For example, the encoding assembly 1902 may be housed within a compartment enclosing the gripper pads and other features of the drive system. As shown in FIG. 63, the encoding assembly 1902 may be separated from the tracking assembly 1904 by a barrier wall 1906, where the wall is typically formed as part of a housing for the drive assembly. The encoding assembly 1902 includes an idler wheel 1908, a tracking wheel 1910, one or more tracking features 1912, a tracking sensor 1914, and a communications module 1916.

The tracking wheel 1910 and the idler wheel 1908 are both round shaped discs and may have a minimal thickness. The outer edge of both the wheels 1908, 1910 is configured to engage the guide wire 1918 and rotate as the guide wire 1918 is moved. The idler wheel 1908 and the tracking wheel 1910 may be each supported on an axle 1920, 1922 or shaft and are configured to rotate in a rotation direction R. In many embodiments, the axle 1920, 1922 for each wheel 1908, 1910 is stationary and the two wheels 1908, 1910 rotate about the axle. In other embodiments, the axle 1920, 1922 for each wheel 1908, 1910 or for one of the wheels 1908, 1910 rotates and may be driven by a motor other source to power the wheels independently of the guide wire.

The tracking features 1912 are defined on or connected to the tracking wheel 1910. For example, the tracking features 1912 may be painted, attached by adhesive, formed via molding, punched out, or attached in many other manners. The configuration and characteristics of the tracking features 1912 are selected so as to be detectable by the tracking sensor 1914. For example, the tracking features 1912 may be differently colored regions on the tracking wheel 1910, magnetic elements, holes or other formations in the tracking wheel, or the like. As one specific example, the tracking wheel 1910 may be transparent and the tracking features may be black lines on the top surface of the tracking wheel 1910. As another example, the tracking wheel 1910 may be opaque and the tracking features 1912 may be tracking apertures defined through the tracking wheel 1910. The tracking features 1912 are varied based on the material, color, texture, or the like, of the tracking wheel 1910 so that the tracking features 1912 can be easily detectable by the tracking sensor 1914, as will be discussed in more detail below.

The tracking sensor 1914 is substantially any type of sensor that can detect changes in location or position of the tracking features 1912 without touching, physically engaging, or mechanically connecting to the tracking wheel 1910 and/or tracking features 1912. In particular, the tracking sensor 1914 may be in communication, either optically, magnetically, acoustically, or the like, with the tracking wheel 1910. In some examples the tracking sensor 1914 is an optical sensor (e.g., light sensor), magnetic sensor (e.g., Hall Effect sensor), and/or an acoustic sensor (e.g., microphone), or the like. As shown in FIG. 63, in one embodiment, the tracking sensor 1914 is shaped as a C-bracket and is in optical communication with both a top and bottom surface of the tracking wheel 1910.

The communication module 1916 is in communication with the tracking sensor 1914 and may include a power source 1924, a circuit board 1926, and a transmitting device 1928. The power source 1924 provides power to the various components of the encoder assembly and may be any component able to provide energy to one or more components. For example, the power source 1924 may be a battery, capacitor, a wireless power transmission mechanism, or a wired power connection.

The circuit board 1926 is in communication with the tracking sensor 1914 and the transmitting device 1928. The circuit board 1926 typically includes the electrical components required for operation of the encoding device. For example, the circuit board 1926 may include one or more processing elements, memory components, and/or other computing components desired.

The transmitting device 1928 is in communication with the processing element or other components on the circuit board 1926 and optionally may be connected to the circuit board. The transmitting device 1928 is substantially any type of data transmission component, such as, but not limited to, a radio wave transmitter, an acoustic transmitter (e.g., piezo electrical transducer, ultrasonic transmitter), optical transmitter, inductive coupling, or the like. The transmitting device 1928 is configured to wirelessly transmit data from the encoding assembly 1902 to the tracking assembly.

The tracking sensor 1914 is in electrical communication with the communications module 1916 so that data can be transmitted from the tracking sensor 1914 to the transmitting device 1928 and so that power, if needed, can be transmitted from the power source 1924 to the tracking sensor 1914.

Each of the components of the encoder assembly 1902, including the tracking sensor 1914, tracking wheel 1910, and communications module 1916 are housed within a sterile environment such that they are separated from the outer environment and the tracking assembly 1904 by the barrier wall.

With continued reference to FIG. 63, the tracking assembly 1904 will now be discussed in more detail. The tracking assembly 1904 includes a receiving device 1930 and optionally a computing device 1932. The receiving device 1930 is in communication with the transmitting device 1928 and is configured to receive data wirelessly from the transmitting device 1928. For example, the receiving device 1930 may be a radio wave receiver, an optical receiver, a microphone or other sound sensor, or the like, as should be appreciated, the receiving device 1930 may be modified to match the data transmission method of the transmitting device 1928.

The computing device 1932 may be substantially any type of computer or other computing element, such as, but not limited to, a laptop computer, server, desktop computer, mobile computing device, tablet computer, microcontroller, digital signal processor, or the like. The computing device 1932 is configured to receive data from the receiver 1930 and determine location and tracking information for the guide wire to determine if slippage has occurred.

Assembly and operation of the slip detection system 1900 will now be discussed in more detail. With reference to FIG. 63, the idler wheel 1908 and the tracking wheel 1910 are each connected to their respective axles 1920, 1922 and positioned adjacent to each other. The two wheels 1908, 1910 may be spaced apart by a distance gap that is substantially the same width as the diameter of the guide wire 1918. The guide wire 1918 is then threaded between the two wheels 1908, 910 so that it is in contact with a portion of the outer edge of each wheel 1908, 1910.

The tracking sensor 1914 is then positioned to be in communication with the tracking wheel 1910. For example, as shown in FIG. 63, the tracking sensor 1914 is positioned so that the tracking wheel 1910 is received between a top and bottom bracket of the tracking sensor 1914 allowing the tracking sensor 1914 to be in optical communication and/or magnetic communication with the tracking wheel. The configuration of the tracking sensor 1914 depends on the type of characteristics to be sensed. For example, the tracking sensor 1914 may be positioned to view one side or surface of the tracking wheel 1910, which may be varied based on the surface including the tracking features.

As discussed above, after the encoding assembly 1902 is arranged or connected together, the assembly may be positioned within a housing or other enclosure. The enclosure forms the barrier wall 1906 and may be hermetically sealed or otherwise define a sterile environment. With continued reference to FIG. 63, the tracking assembly 1904 is positioned on the non-sterile side of the barrier wall 1906 and is arranged to provide communication between the transmitting device 1928 and the receiving device 1930 through the barrier wall 1906 without distributing or disrupting the sterile environment.

Operation of the slip detection system 1900 will now be discussed in more detail. As the guide wire 1918 is inserted and/or retracted by the drive assembly, the guide wire 1918 exerts a force on the outer edges of the idler wheel 1908 and the tracking wheel 1910. This force causes the two wheels 1908, 1910 to rotate in the rotation direction R. In some embodiments, the idler wheel 1908 and the tracking wheel 1910 may rotate in opposite directions from each other, i.e., clockwise and counter clockwise, respectively. The rotation direction may be determined by the orientation of the guide wire 1918 relative to the wheel. As noted above, in some embodiments, one or both of the idler wheel 1908 or tracking wheel 1910 may be driven by a source other than the guide wire. For example, one or both of the wheels may assist in retracting/inserting the guide wire.

As the tracking wheel 1910 rotates with movement of the guide wire 1918, the tracking features 1912 move correspondingly. As the tracking features 1912 are connected to the tracking wheel 1910, they will rotate with the tracking wheel 1910 and vary their location relative to the tracking sensor 1914. As the tracking features 1912 move or change position relative to the tracking sensor 1914, the tracking sensor 1914 detects the change in position of the tracking features 1912. For example, each tracking feature may correspond to a particular location on the tracking wheel 1910 so as the tracking sensor 1914 detects a particular tracking feature 1912 the orientation of the tracking wheel 1910 relative to the sensing location can be determined. As another example, the tracking sensor 1914 can detect the number of tracking features 1912 and the rate they are passing by or through the sensor 1914 and this information can be used to determine data related to the guide wire. In other words, the data corresponding to the tracking features 1912 detected by the tracking sensor 1914 is the guide wire data as it provides information related to the movement characteristics of the guide wire.

As the tracking sensor 1914 detects the change in position and/or speed of the tracking wheel 1910 via the tracking features 1912, the tracking sensor 1914 provides the guide wire data to the circuit board 1926 which then provides the guide wire data to the transmitting device 1928. The transmitting device 1928 then transmits the guide wire data wirelessly through the barrier wall to the tracking assembly 1904. The receiving device 1930 of the tracking assembly 1904 receives the data and optionally may transmit the data to the computing device 1932. The computing device 1932 analyzes the guide wire data and may provide an output (e.g., alert, stopping the drive assembly, notification, or the like). For example, if the computing device determines that the guide wire 1918 is moving slower than desired, has not moved as far as desired, or another deviation from a predetermined threshold, the computing device 1932 will determine that a slip has occurred and provide the desired output. In other words, the receiving device 1930 and/or computing device 1932 act to decode the guide wire data and analyze the guide wire data to determine if a slip or other event has occurred.

Using the slip detection system 1900 of FIG. 63, the location, movement, speed, and other characteristics of the guide wire 1918 can be detected during a procedure, such as insertion or retraction. The slip detection system 1900 can be configured to provide alerts or other outputs in response to a deviation from a desired function. This helps to alert doctors and other health care workers substantially instantaneously when a slip occurs, allowing the slip to be mitigated as soon as possible. Additionally, because the slip detection system 1900 uses an encoder assembly 1902 that consumes very little energy from the guide wire 1918, operation of the drive assembly is not substantially affected by the slip detection features, as compared to conventional tracking techniques that use substantial amounts of torque to activate the encoder. Finally, because the slip detection system 1900 transmits the guide wire data wirelessly, the tracking assembly 1904 can be located outside of the sterile location or housing, allowing the encoding assembly to be to hermetically encapsulated for sterilization purposes, where the decoding and other computing intensive functions can be done outside the sterilized environment.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the systems and one or more portions of the processor, controller, or workstation. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A drive system for an elongate member comprising:
a first surface engaged with the elongate member;
a second surface engaged with the elongate member;
a plurality of sensors configured to indicate differences between a translational displacement of a distal portion of the elongate member and a translational displacement of a proximal portion of the elongate member; and
a computing device in communication with the plurality of sensors, the computing device configured to detect a slip occurrence of the elongate member based at least on data from the plurality of sensors.

2. The system of claim 1, wherein the plurality of sensors includes at least one sensor configured to measure a force applied to the elongate member.

3. The system of claim 1, wherein the computing device is further configured to adjust a grip force of either of the first surface or the second surface on the elongate member in response to a detection of a slip occurrence.

4. The system of claim 1, wherein the computing device is configured to adjust a grip force of either of the first surface or the second surface on the elongate member based on a comparison of an applied grip force to a predetermined grip force range of either the first surface or the second surface.

5. The system of claim 1, further comprising a first housing portion for the first surface and a second housing portion for the second surface.

6. The system of claim 5, further comprising a linear guide that extends between the first housing portion and the second housing portion.

7. The system of claim 1, wherein the first surface is part of a first roller and the second surface is part of a second roller.

8. The system of claim 7, wherein the first roller is associated with a first set of rotational mechanisms and the second roller is associated with a second set of rotational mechanisms.

9. The system of claim 8, wherein the first set of rotational mechanisms comprises a first set of geared teeth and the second set of rotational mechanisms comprises a second set of geared teeth, wherein the first set of geared teeth and the second set of geared teeth are meshingly engaged.

10. The system of claim 1, wherein the first surface and/or the second surface are padded surfaces.

11. The system of claim 1, wherein the first surface and/or the second surface comprise a polymer.

12. The system of claim 11, wherein the first surface and/or second surface is deformable.

13. The system of claim 1, wherein the first surface and/or the second surface comprise treading.

14. The system of claim 1, further comprising an encoder assembly, wherein the encoder assembly is housed within a compartment that houses the first surface and the second surface.

15. A drive system for an elongate member comprising:
a first surface engaged with the elongate member;
a second surface engaged with the elongate member;
a plurality of displacement sensors, the plurality of displacement sensors being configured to sense displacement of different longitudinal regions of the elongate member; and
a computing device in communication with the plurality of displacement sensors, the computing device configured to detect discrepancies between displacements of said different longitudinal regions of the elongate member to thereby detect a slip occurrence of the elongate member.

16. The drive system of claim 15, wherein the first surface and/or second surface comprise treading.

17. The drive system of claim 16, wherein the first surface and/or second surface is deformable.

18. The drive system of claim 15, wherein the first surface is part of a first roller and the second surface is part of a second roller.

19. The drive system of claim 15, further comprising an encoder assembly housed in a compartment that houses the first surface and the second surface.

20. A drive system for an elongate member comprising:
a drive assembly operable to drive translation of the elongate member;
a first sensor configured to indicate a translational displacement of a distal portion of the elongate member;
a second sensor configured to indicate a translational displacement of a proximal portion of the elongate member; and
a computing device configured to detect a slip or buckling occurrence of the elongate member based at least on a discrepancy between a translational displacement indicated by the first sensor and a translational displacement indicated by the second sensor.

* * * * *